United States Patent
Eastman et al.

(10) Patent No.: US 10,189,816 B2
(45) Date of Patent: Jan. 29, 2019

(54) SUBSTITUTED PYRIDINES AS INHIBITORS OF HUMAN IMMUNODEFICIENCY VIRUS REPLICATION

(71) Applicant: ViiV Healthcare UK (No.5) Limited, Brentford, Middlesex (GB)

(72) Inventors: Kyle J. Eastman, Wallingford, CT (US); John F. Kadow, Wallingford, CT (US); Kyle E. Parcella, Wallingford, CT (US); B. Narasimhulu Naidu, Wallingford, CT (US); Tao Wang, Wallingford, CT (US); Zhiwei Yin, Wallingford, CT (US); Zhongxing Zhang, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/749,176

(22) PCT Filed: Aug. 10, 2016

(86) PCT No.: PCT/IB2016/054832
§ 371 (c)(1),
(2) Date: Jan. 31, 2018

(87) PCT Pub. No.: WO2017/025917
PCT Pub. Date: Feb. 16, 2017

(65) Prior Publication Data
US 2018/0230129 A1    Aug. 16, 2018

Related U.S. Application Data

(60) Provisional application No. 62/203,791, filed on Aug. 11, 2015.

(51) Int. Cl.
*A61K 31/444* (2006.01)
*C07D 401/02* (2006.01)
*C07D 401/14* (2006.01)
*C07D 401/04* (2006.01)
*A61P 31/18* (2006.01)
*A61K 31/5365* (2006.01)

(52) U.S. Cl.
CPC .......... *C07D 401/14* (2013.01); *A61K 31/444* (2013.01); *A61P 31/18* (2018.01); *C07D 401/04* (2013.01); *A61K 31/5365* (2013.01); *A61K 2300/00* (2013.01)

(58) Field of Classification Search
CPC ............................ A61K 31/444; C07D 401/02
USPC ........................................ 514/340; 546/268.1
See application file for complete search history.

(56) References Cited

FOREIGN PATENT DOCUMENTS

| WO | WO 2010/130034 A1 | 11/2010 |
|----|-------------------|---------|
| WO | WO 2015/126726 A1 | 8/2015  |
| WO | WO 2015/127003 A1 | 8/2015  |

OTHER PUBLICATIONS

R. DiSanto. "Inhibiting the HIV Integration Process: Past, Present, and the Future". Journal of Medicinal Chemistry, 57(3): 539-566 (Feb. 13, 2014).

*Primary Examiner* — Douglas M Willis
(74) *Attorney, Agent, or Firm* — Robert H. Brink; Kathryn A. Lutomski; Edward R. Gimmi

(57) ABSTRACT

Disclosed are compounds of Formula (I), including pharmaceutically acceptable salts, pharmaceutical compositions comprising the compounds, methods for making the compounds and their use in inhibiting HIV integrase and treating those infected with HIV or AIDS. In the compounds of formula (I), $R^1$ is selected from hydrogen, alkyl, or cycloalkyl; $R^2$ is selected from tetrahydroisoquinolinyl and is substituted with 1 $R^6$ substituent and also with 0-3 halo or alkyl substituents; $R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy; $R^4$ is selected from alkyl or haloalkyl; $R^5$ is alkyl; $R^6$ is selected from $Ar^1$, $(Ar^1)$alkyl, (chromanyl)alkyl, cyanocycloalkyl or (dihydrobenzodioxinyl)alkyl; and $Ar^1$ is phenyl substituted with 0-5 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl.

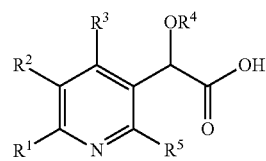

8 Claims, No Drawings

SUBSTITUTED PYRIDINES AS INHIBITORS OF HUMAN IMMUNODEFICIENCY VIRUS REPLICATION

CROSS REFERENCE TO RELATED INVENTION

This application is a § 371 of International Application No. PCT/IB2016/054832, filed 10 August 2016, which claims the benefit of U.S. Provisional Application No. 62/203,791, filed 11 Aug. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

In addition, the invention provides methods for inhibiting HIV integrase.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to, indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —$(CH_2)_n$Ph with n=1-5, —$CH(CH_3)$Ph, —$CH(Ph)_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)_n$—$R^Z$ or —CH$(CH_3)$—$(R^Z)$ where n=1-5 and that $R^Z$ is chosen from benzimidazole, imidazole, indazole, isooxazole, phenylpyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

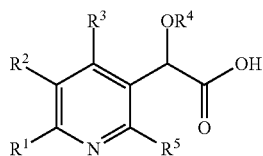

wherein:
$R^1$ is selected from hydrogen, alkyl, or cycloalkyl;
$R^2$ is selected from tetrahydroisoquinolinyl and is substituted with 1 $R^6$ substituent and also with 0-3 halo or alkyl substituents;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl;
$R^6$ is selected from $Ar^1$, $(Ar^1)$alkyl, (chromanyl)alkyl, cyanocycloalkyl or (dihydrobenzodioxinyl)alkyl; and
$Ar^1$ is phenyl substituted with 0-5 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl;
or a pharmaceutically acceptable salt thereof.

In an aspect of the invention, $R^2$ is tetrahydroisoquinolinyl substituted with 1 $R^6$ substituent.

In an aspect of the invention, $R^3$ is piperidinyl substituted with 0-3 substituents selected from cyano, halo, alkyl, haloalkyl, alkoxy, and haloalkoxy.

In an aspect of the invention, $R^6$ is $(Ar^1)$alkyl.

In an aspect of the invention, $R^6$ is $Ar^1$, (chromanyl)alkyl, (dihydrobenzodioxinyl)alkyl, or cyanocycloalkyl.

In an aspect of the invention, $Ar^1$ is phenyl substituted with 0-3 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl.

In an aspect of the invention, there is provided a compound of Formula I:

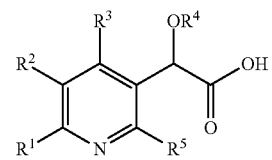

wherein:
$R^1$ is selected from hydrogen, alkyl, or cycloalkyl;
$R^2$ is selected from tetrahydroisoquinolinyl and is substituted with 1 $R^6$ substituent and also with 0-3 halo or alkyl substituents;
$R^3$ is piperidinyl substituted with 0-3 substituents selected from cyano, halo, alkyl, haloalkyl, alkoxy, and haloalkoxy;
$R^4$ is selected from alkyl or haloalkyl;
$R^5$ is alkyl;
$R^6$ is selected from $Ar^1$, $(Ar^1)$alkyl, (chromanyl)alkyl, cyanocycloalkyl or (dihydrobenzodioxinyl)alkyl; and
$Ar^1$ is phenyl substituted with 0-5 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl;
or a pharmaceutically acceptable salt thereof.

In an aspect of the invention, there is provided a compound of Formula I:

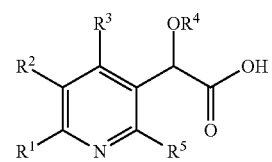

wherein:
$R^1$ is selected from hydrogen, alkyl, or cycloalkyl;
$R^2$ is selected from tetrahydroisoquinolinyl and is substituted with 1 $R^6$ substituent and also with 0-3 halo or alkyl substituents;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl;
$R^6$ is $(Ar^1)$alkyl; and
$Ar^1$ is phenyl substituted with 0-5 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl;
or a pharmaceutically acceptable salt thereof.

In an aspect of the invention, there is provided a compound of Formula I:

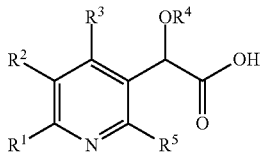

wherein:
R¹ is selected from hydrogen, alkyl, or cycloalkyl;
R² is selected from tetrahydroisoquinolinyl and is substituted with 1 R⁶ substituent and also with 0-3 halo or alkyl substituents;
R³ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
R⁴ is selected from alkyl or haloalkyl;
R⁵ is alkyl;
R⁶ is selected from Ar¹, (chromanyl)alkyl, (dihydrobenzodioxinyl)alkyl, or cyanocycloalkyl; and
Ar¹ is phenyl substituted with 0-5 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl;
or a pharmaceutically acceptable salt thereof.

In an aspect of the invention, there is provided a compound of Formula I:

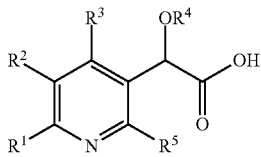

wherein:
R¹ is selected from hydrogen, alkyl, or cycloalkyl;
R² is selected from tetrahydroisoquinolinyl and is substituted with 1 R⁶ substituent and also with 0-3 halo or alkyl substituents;
R³ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
R⁴ is selected from alkyl or haloalkyl;
R⁵ is alkyl;
R⁶ is selected from Ar¹, (Ar¹)alkyl, (chromanyl)alkyl, cyanocycloalkyl or (dihydrobenzodioxinyl)alkyl; and
Ar¹ is phenyl substituted with 0-3 substituents selected from cyano, halo, alkyl, cycloalkyl, haloalkyl, hydroxy, alkoxy, haloalkoxy, (hydroxy)alkoxy, (alkoxy)alkoxy, phenoxy, benzyloxy, carboxy, phenyl, and cyanocycloalkyl;
or a pharmaceutically acceptable salt thereof.

For a particular compound of Formula I, the scope of any instance of a variable substituent, including R¹, R², R³, R⁴, R⁵, R⁶ and Ar¹ can be used independently with the scope of any other instance of a variable substituent. As such, the invention includes combinations of the different aspects.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I.

Preferred compounds in accordance with the present invention include the following:
(S)-2-(tert-butoxy)-2-(4-(4,4-dimethylpiperidin-1-yl)-5-(2-(4-fluorobenzyl)-1,2,3,4-tetrahydroisoquinolin-6-yl)-2,6-dimethylpyridin-3-yl)acetic acid;
(S)-2-(tert-butoxy)-2-(4-(4,4-dimethylpiperidin-1-yl)-2,6-dimethyl-5-(2-(3-(trifluoromethyl)benzyl)-1,2,3,4-tetrahydroisoquinolin-6-yl)pyridin-3-yl)acetic acid;
(S)-2-(tert-butoxy)-2-(4-(4,4-dimethylpiperidin-1-yl)-2,6-dimethyl-5-(2-(3-methylbenzyl)-1,2,3,4-tetrahydroisoquinolin-6-yl)pyridin-3-yl)acetic acid;
(S)-2-(tert-butoxy)-2-(4-(4,4-dimethylpiperidin-1-yl)-2,6-dimethyl-5-(2-(2-methylbenzyl)-1,2,3,4-tetrahydroisoquinolin-6-yl)pyridin-3-yl)acetic acid;
(S)-2-(tert-butoxy)-2-(4-(4,4-dimethylpiperidin-1-yl)-2,6-dimethyl-5-(2-(4-methylbenzyl)-1,2,3,4-tetrahydroisoquinolin-6-yl)pyridin-3-yl)acetic acid;
(S)-2-(tert-butoxy)-2-(4-(4,4-dimethylpiperidin-1-yl)-5-(2-(3-methoxybenzyl)-1,2,3,4-tetrahydroisoquinolin-6-yl)-2,6-dimethylpyridin-3-yl)acetic acid;
(S)-2-(tert-butoxy)-2-(4-(4,4-dimethylpiperidin-1-yl)-5-(2-(3-fluorobenzyl)-1,2,3,4-tetrahydroisoquinolin-6-yl)-2,6-dimethylpyridin-3-yl)acetic acid;
(S)-2-(tert-butoxy)-2-(4-(4,4-dimethylpiperidin-1-yl)-2,6-dimethyl-5-(2-(4-(trifluoromethyl)benzyl)-1,2,3,4-tetrahydroisoquinolin-6-yl)pyridin-3-yl)acetic acid;
(S)-2-(tert-butoxy)-2-(4-(4,4-dimethylpiperidin-1-yl)-5-(2-(2-fluorobenzyl)-1,2,3,4-tetrahydroisoquinolin-6-yl)-2,6-dimethylpyridin-3-yl)acetic acid;
(S)-3-((6-(5-(tert-butoxy(carboxy)methyl)-4-(4,4-dimethylpiperidin-1-yl)-2,6-dimethylpyridin-3-yl)-3,4-dihydroisoquinolin-2(1H)-yl)methyl)benzoic acid;
(S)-2-(5-(2-([1,1'-biphenyl]-3-ylmethyl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(4-(4,4-dimethylpiperidin-1-yl)-2,6-dimethyl-5-(2-(2-(trifluoromethyl)benzyl)-1,2,3,4-tetrahydroisoquinolin-6-yl)pyridin-3-yl)acetic acid;

(2S)-2-(tert-butoxy)-2-(4-(4,4-dimethylpiperidin-1-yl)-2,6-dimethyl-5-(2-(1-phenylethyl)-1,2,3,4-tetrahydroisoquinolin-6-yl)pyridin-3-yl)acetic acid;

(S)-2-(5-(2-([1,1'-biphenyl]-4-ylmethyl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(4-(4,4-dimethylpiperidin-1-yl)-2,6-dimethyl-5-(2-(2-methyl-3-(trifluoromethyl)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(4-methyl-3-(trifluoromethyl)benzyl)-1,2,3,4-tetrahydroisoquinolin-6-yl)pyridin-3-yl)acetic acid;

(S)-2-(tert-butoxy)-2-(5-(2-(3,4-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(3-fluoro-4-methylbenzyl)-1,2,3,4-tetrahydroisoquinolin-6-yl)-2,6-dimethylpyridin-3-yl)acetic acid;

(S)-2-(tert-butoxy)-2-(5-(2-(2,4-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,4-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,3-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-chloro-3-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-4-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2,6-dimethylpyridin-3-yl)acetic acid;

(S)-2-(tert-butoxy)-2-(5-(2-(3,5-dichlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-(tert-butyl)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,5-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-6-(trifluoromethyl)benzyl)-1,2,3,4-tetrahydroisoquinolin-6-yl)-2,6-dimethylpyridin-3-yl)acetic acid;

(S)-2-(tert-butoxy)-2-(5-(2-(3,5-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-3-(trifluoromethyl)benzyl)-1,2,3,4-tetrahydroisoquinolin-6-yl)-2,6-dimethylpyridin-3-yl)acetic acid;

(S)-2-(tert-butoxy)-2-(5-(2-(2,6-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(3,4,5-trifluorobenzyl)-1,2,3,4-tetrahydroisoquinolin-6-yl)pyridin-3-yl)acetic acid;

(S)-2-(tert-butoxy)-2-(5-(2-(2-chloro-4-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(3-isopropylbenzyl)-1,2,3,4-tetrahydroisoquinolin-6-yl)-2,6-dimethylpyridin-3-yl)acetic acid;

(S)-2-(tert-butoxy)-2-(5-(2-(3,4-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,5-difluorobenzyl)-1,2,3,4-tetrahydroisoquinolin-6-yl)-4-(4,4-dimethylpiperidin-1-yl)-2,6-dimethylpyridin-3-yl)acetic acid (S)-2-(tert-butoxy)-2-(5-(2-(4-chloro-2-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,3-dichlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(2,3,4-trifluorobenzyl)-1,2,3,4-tetrahydroisoquinolin-6-yl)pyridin-3-yl)acetic acid;

(S)-2-(tert-butoxy)-2-(5-(2-(5-chloro-2-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-5-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(2,3,6-trifluorobenzyl)-1,2,3,4-tetrahydroisoquinolin-6-yl)pyridin-3-yl)acetic acid;

(S)-2-(tert-butoxy)-2-(5-(2-(2-chloro-5-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(3-fluoro-5-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(5-fluoro-2-methylbenzyl)-1,2,3,4-tetrahydroisoquinolin-6-yl)-2,6-dimethylpyridin-3-yl)acetic acid;

(S)-2-(tert-butoxy)-2-(5-(2-(2,6-difluoro-3-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(2,4,5-trifluorobenzyl)-1,2,3,4-tetrahydroisoquinolin-6-yl)pyridin-3-yl)acetic acid;

(S)-2-(tert-butoxy)-2-(5-(2-(2,6-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-6-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(2-methyl-5-(trifluoromethyl)benzyl)-1,2,3,4-tetrahydroisoquinolin-6-yl)pyridin-3-yl)acetic acid;

(S)-2-(tert-butoxy)-2-(5-(2-(2,4-dichlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-3-methylbenzyl)-1,2,3,4-tetrahydroisoquinolin-6-yl)-2,6-dimethylpyridin-3-yl)acetic acid;

(S)-2-(tert-butoxy)-2-(5-(2-(2-chlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-(4-chlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(2,4,6-trimethylbenzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(2,4,6-trifluorobenzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(4-isopropylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-ethylbenzyl)-1,2,3,4-tetrahydroisoquinolin-6-yl)-2,6-dimethylpyridin-3-yl)acetic acid;

(S)-2-(tert-butoxy)-2-(5-(2-(3-cyanobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-cyanobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(5-cyano-2-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-cyanobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-cyano-2-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(5-fluoro-2-(trifluoromethyl)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-3-(trifluoromethyl)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-fluoro-5-(trifluoromethyl)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-2-(trifluoromethyl)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-fluoro-5-(trifluoromethyl)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-3-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-2,3-dimethylbenzyl)-1,2,3,4-tetrahydroisoquinolin-6-yl)-2,6-dimethylpyridin-3-yl)acetic acid;

(S)-2-(tert-butoxy)-2-(5-(2-(2,3-difluoro-4-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-5-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-3,5-dimethylbenzyl)-1,2,3,4-tetrahydroisoquinolin-6-yl)-2,6-dimethylpyridin-3-yl)acetic acid;

(S)-2-(tert-butoxy)-2-(5-(2-(3,4-difluoro-5-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-isopropylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(2,4,5-trimethylbenzyl)-1,2,3,4-tetrahydroisoquinolin-6-yl)pyridin-3-yl)acetic acid;

(S)-2-(tert-butoxy)-2-(5-(2-(3,5-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,3-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-(tert-butyl)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(3-fluoro-2-methylbenzyl)-1,2,3,4-tetrahydroisoquinolin-6-yl)-2,6-dimethylpyridin-3-yl)acetic acid;

(S)-2-(tert-butoxy)-2-(5-(2-(2,5-difluoro-4-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,6-difluoro-4-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(5-(2-(2-(benzyloxy)-3,5-dichlorobenzyl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(5-(2-(4,5-difluoro-2-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,3-difluoro-6-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-(2-hydroxyethoxy)benzyl)-1,2,3,4-tetrahydroisoquinolin-6-yl)-2,6-dimethylpyridin-3-yl)acetic acid;

(S)-2-(tert-butoxy)-2-(5-(2-(2,4-difluoro-6-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,4-dichloro-6-ethoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,3-dichloro-4-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,6-difluoro-3-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-chloro-2-fluoro-5-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,4-difluoro-5-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3,5-difluoro-4-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(2,3,5-trifluorobenzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(3-fluoro-4-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-methoxy-3-(trifluoromethyl)benzyl)-1,2,3,4-tetrahydroisoquinolin-6-yl)-2,6-dimethylpyridin-3-yl)acetic acid;

(S)-2-(tert-butoxy)-2-(5-(2-(5-chloro-2-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-5-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(4-fluoro-3-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(4-(trifluoromethoxy)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(3-ethoxybenzyl)-1,2,3,4-tetrahydroisoquinolin-6-yl)-2,6-dimethylpyridin-3-yl)acetic acid;

(S)-2-(tert-butoxy)-2-(5-(2-(3-chloro-4-(trifluoromethoxy)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-(difluoromethoxy)-2-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,6-difluoro-4-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,4-difluoro-6-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(3-fluoro-4-(trifluoromethoxy)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-methoxy-4-(trifluoromethyl)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(3-(trifluoromethoxy)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(3-fluoro-5-(trifluoromethoxy)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-methoxy-5-(trifluoromethyl)benzyl)-1,2,3,4-tetrahydroisoquinolin-6-yl)-2,6-dimethylpyridin-3-yl)acetic acid;

(S)-2-(tert-butoxy)-2-(5-(2-(3-chloro-5-(trifluoromethoxy)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-(difluoromethoxy)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-6-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-fluoro-5-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-2-methoxybenzyl)-1,2,3,4-tetrahydroisoquinolin-6-yl)-2,6-dimethylpyridin-3-yl)acetic acid;

(S)-2-(tert-butoxy)-2-(5-(2-(3-(difluoromethoxy)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-methoxy-5-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-3-(trifluoromethoxy)benzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(3-(1,1,2,2-tetrafluoroethoxy)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(3-fluoro-5-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(2-(trifluoromethoxy)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(5-fluoro-2-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-2,6-dimethyl-5-(2-(4-(1,1,2,2-tetrafluoroethoxy)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(5-ethoxy-2,4-difluorobenzyl)-1,2,3,4-tetrahydroisoquinolin-6-yl)-2,6-dimethylpyridin-3-yl)acetic acid;

(S)-2-(tert-butoxy)-2-(5-(2-(3,4-dichlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,6-dichlorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-chloro-3-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-2-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-chloro-2-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-4-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(5-chloro-2-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-chloro-3-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-chloro-2,6-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-chloro-6-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-4-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-chloro-3-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(5-isopropyl-2-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-methoxy-4-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-methoxy-3-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-fluoro-2-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-isopropyl-4-methoxybenzyl)-1,2,3,4-tetrahydroisoquinolin-6-yl)-2,6-dimethylpyridin-3-yl)acetic acid;

(S)-2-(tert-butoxy)-2-(5-(2-(2,4-difluoro-6-hydroxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-chloro-6-methoxybenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-4-methoxybenzyl)-1,2,3,4-tetrahydroisoquinolin-6-yl)-2,6-dimethylpyridin-3-yl)acetic acid (S)-2-(tert-butoxy)-2-(4-(4,4-dimethylpiperidin-1-yl)-5-(2-(4-methoxy-2,3-dimethylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-methoxy-2,5-dimethylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-ethoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-isopropoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-methoxy-5-(trifluoromethyl)benzyl)-1,2,3,4-tetrahydroisoquinolin-6-yl)-2,6-dimethylpyridin-3-yl)acetic acid (S)-2-(tert-butoxy)-2-(4-(4,4-dimethylpiperidin-1-yl)-5-(2-(2-isopropoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-isobutoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-isopropoxybenzyl)-1,2,3,4-tetrahydroisoquinolin-6-yl)-2,6-dimethylpyridin-3-yl)acetic acid;

(S)-2-(tert-butoxy)-2-(5-(2-(chroman-6-ylmethyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-((2,3-dihydrobenzo[b][1,4]dioxin-6-yl)methyl)-1,2,3,4-tetrahydroisoquinolin-6-yl)-4-(4,4-dimethylpiperidin-1-yl)-2,6-dimethylpyridin-3-yl)acetic acid;

(S)-2-(5-(2-(3,4-bis(difluoromethoxy)benzyl)-1,2,3,4-tetrahydroisoquinolin-6-yl)-4-(4,4-dimethylpiperidin-1-yl)-2,6-dimethylpyridin-3-yl)-2-(tert-butoxy)acetic acid;

(S)-2-(tert-butoxy)-2-(5-((2,3-dihydrobenzo[b][1,4]dioxin-5-yl)methyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(2-fluoro-6-phenoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-isopropoxy-2,6-dimethylbenzyl)-1,2,3,4-tetrahydroisoquinolin-6-yl)-2,6-dimethylpyridin-3-yl)acetic acid;

(S)-2-(tert-butoxy)-2-(5-(2-(3,4-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(4-(1-cyanocyclopropyl)benzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(4-(nonyloxy)benzyl)-1,2,3,4-tetrahydroisoquinolin-6-yl)pyridin-3-yl)acetic acid;

(S)-2-(tert-Butoxy)-2-(5-(2-(2-chloro-6-methylbenzyl)-1,2,3,4-tetrahydroisoquinolin-6-yl)-4-(4,4-dimethylpiperidin-1-yl)-2-methylpyridin-3-yl)acetic acid;

(S)-2-(tert-Butoxy)-2-(4-(4,4-dimethylpiperidin-1-yl)-2-methyl-5-(2-(2-methylbenzyl)-1,2,3,4-tetrahydroisoquinolin-6-yl)pyridin-3-yl)acetic acid;

(S)-2-(tert-Butoxy)-2-(5-(2-(2-chloro-6-methylbenzyl)-1,2,3,4-tetrahydroisoquinolin-6-yl)-4-(3,3-dimethylpiperidin-1-yl)-2,6-dimethylpyridin-3-yl)acetic acid;

(S)-2-(tert-butoxy)-2-(4-(4,4-dimethylpiperidin-1-yl)-2,6-dimethyl-5-(2-(3-methylbenzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(2-methylbenzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-2,6-dimethyl-5-(2-(3-(trifluoromethyl)benzyl)-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(2-fluorobenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-fluorobenzyl)-1,2,3,4-tetrahydroisoquinolin-6-yl)-2,6-dimethylpyridin-3-yl)acetic acid;

(S)-2-(tert-butoxy)-2-(5-(2-(3,4-dimethylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,4-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2,3-difluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(5-(2-(3-chloro-4-fluorobenzyl)-1,2,3,4-tetrahydroisoquinolin-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(2-fluoro-6-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(4-fluoro-2-methoxybenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(3-fluoro-2-methylbenzyl)-1,2,3,4-tetrahydroisoquinolin-6-yl)-2,6-dimethylpyridin-3-yl)acetic acid;

(S)-2-(tert-butoxy)-2-(4-(4,4-dimethylpiperidin-1-yl)-5-(2-(5-fluoro-2-methoxybenzyl)-1,2,3,4-tetrahydroisoquinolin-6-yl)-2,6-dimethylpyridin-3-yl)acetic acid; and (S)-2-(tert-Butoxy)-2-(5-(2-(2-chloro-6-methylbenzyl)-1,2,3,4-tetrahydroisoquinolin-6-yl)-4-(4,4-dimethylpiperidin-1-yl)-2-methylpyridin-3-yl)acetic acid; and pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhinitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

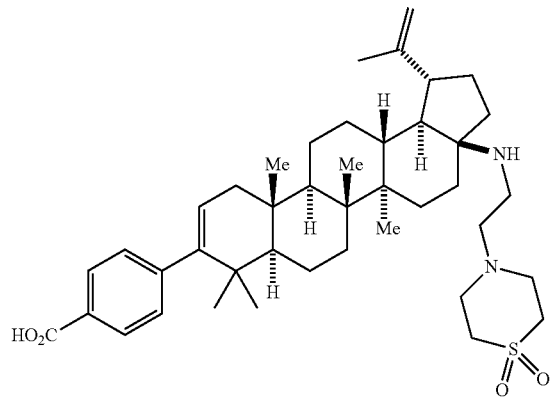

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| ANTIVIRALS | | |
|---|---|---|
| Drug Name | Manufacturer | Indication |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |

-continued

| ANTIVIRALS | | |
|---|---|---|
| Drug Name | Manufacturer | Indication |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |

-continued

ANTIVIRALS

| Drug Name | Manufacturer | Indication |
| --- | --- | --- |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |

ANTIVIRALS

| Drug Name | Manufacturer | Indication |
|---|---|---|
| GSK1349572 Integrase inhibitor TIVICAY® dolutegravir | GSK | HIV infection AIDs |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

METHODS OF SYNTHESIS

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd " for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be prepared by the methods outlined in the Scheme I

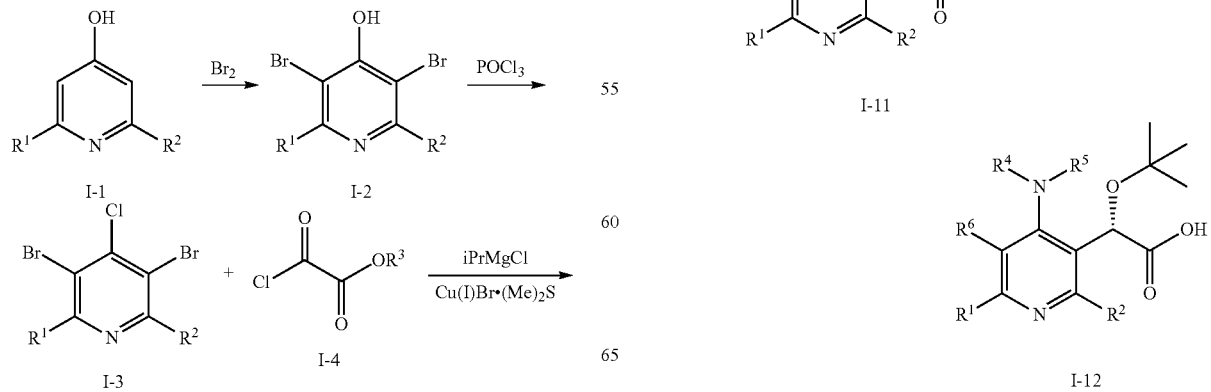

Some compounds of this invention can be prepared by the methods outlined in the Scheme II.

Scheme II

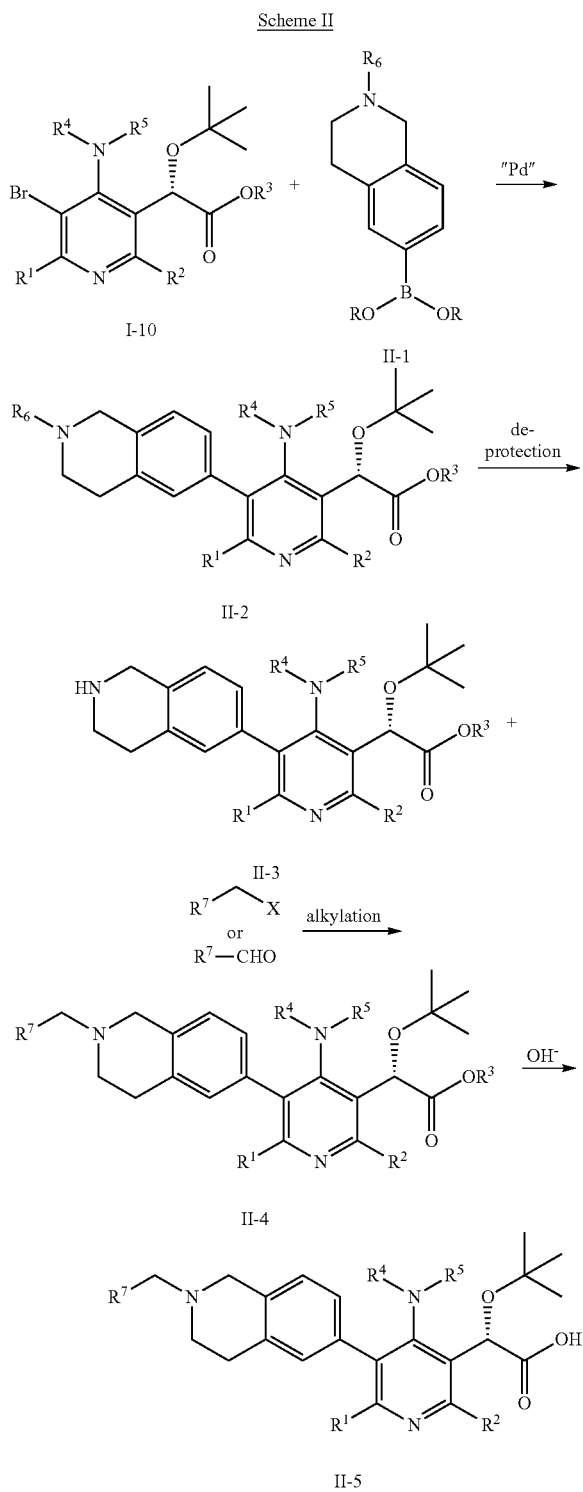

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 µm; 19 or 30×100 mm) or Waters Xbridge C18 column (5 µM; 19×200 or 30×100 mm) or Water Atlantis (5 µm; 19 or 30×100 mm) using the following mobile phases. Mobile phase A: 9:1 H$_2$O/acetonitrile with 10 mM NH$_4$OAc and mobile phase B: A: 9:1 acetonitrile/H$_2$O with 10 mM NH$_4$OAc; or mobile phase A: 9:1 H$_2$O/acetonitrile with 0.1% TFA and mobile phase B: A: 9:1 acetonitrile/H$_2$O with 0.1% TFA; or mobile phase A: water/MeOH (9:1) with 20 mM NH$_4$OAc and mobile phase B: 95:5 MeOH/H$_2$O with 20 mM NH$_4$OAc or mobile phase A: water/MeOH (9:1) with 0.1% TFA and mobile phase B: 95:5 MeOH/H$_2$O with 0.1% TFA or mobile Phase A: 5:95 acetonitrile: water with 10-mM ammonium acetate; Mobile Phase B: 95:5 acetonitrile: water with 10-mM ammonium acetate.

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

Compounds purified by preparative HPLC were diluted in methanol (1.2 mL) or DMF and purified using a Shimadzu LC-8A or LC-10A automated preparative HPLC system.

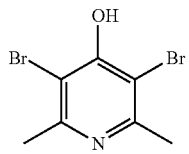

3,5-Dibromo-2,6-dimethylpyridin-4-ol: A 3-neck R.B-flask equipped with mechanical stirrer, addition funnel and condenser is charged with 2,6-dimethylpyridin-4-ol (100 g, 812 mmol), CH$_2$Cl$_2$ (1000 mL) and MeOH (120 mL). To the resulting light brown or tan solution was added tert-BuNH2 (176 ml, 1665 mmol), cooled in water bath maintained between 5-10° C. (ice-water) and added drop wise Br$_2$ (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-d$_6$) δ 12.08 (br. s., 1H), 2.41 (s, 6H). LCMS (M+H)=281.9.

Alternative procedure: Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2,6-dimethylpyridin-4-ol 176.8 g (88%).

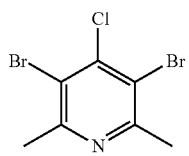

3,5-Dibromo-4-chloro-2,6-dimethylpyridine: Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed from heating and immediately concentrated under house vaccum; then under high vacuum. The appearance was a cream colored solid, which was azeotroped with toluene (2×100 mL); treated with ice (200 g) for 10 min and carefully neutralized with NaHCO$_3$ (powder), and 1N NaOH solution, and extracted with DCM (2×400 mL). The combined organic layers were dried (MgSO$_4$), concentrated, and a beige solid was obtained that was washed with hexanes and dried under high vacuum to give 3,5-dibromo-4-chloro-2,6-dimethyl-pyridine 52.74 g (85.1%). Concentration of the hexanes gave 3.5 g of less pure product. $^1$H NMR (500 MHz, CDCl$_3$) δ 2.59 (s, 6H). LCMS (M+H)=300.0.

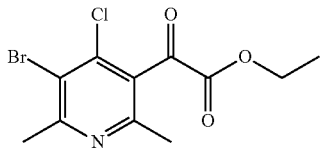 [SMILES: CCOC(=O)C(=O)c1c(C)nc(C)c(Br)c1Cl]

Ethyl 2-(5-bromo-4-chloro-2,6-dimethylpyridin-3-yl)-2-oxoacetate: To a stirred mixture of 3,5-dibromo-4-chloro-2,6-dimethylpyridine (14.94 g, 49.9 mmol) and Cu(I)Br Me2S (0.513 g, 2.495 mmol) in THF (50 mL) was added drop wise 2M iPrMgCl/THF (26.2 ml, 52.4 mmol) at −30° C. over 5 min. Then, the resulting slurry was warmed to −10° C. over 30 min and stirred for 30 min. The homogeneous brown reaction mixture was rapidly transferred via cannula to a solution of ethyl 2-chloro-2-oxoacetate (6.14 ml, 54.9 mmol, degassed for 5 min by bubbling N2 through the solution) in THF (50 mL) maintained at −30° C. The resulting reaction mixture was stirred (1.5 h) while warming to 0° C. Then, taken up in to Et$_2$O (200 mL), washed with 1:1 sat Na$_2$CO$_3$/1M NH$_4$Cl (3×50 mL), dried (MgSO$_4$), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl$_3$) δ 4.42 (q, J=7.0 Hz, 2H), 2.76 (s, 3H), 2.46 (s, 3H), 1.41 (t, J=7.2 Hz, 3H). LCMS (M+H)=322.1.

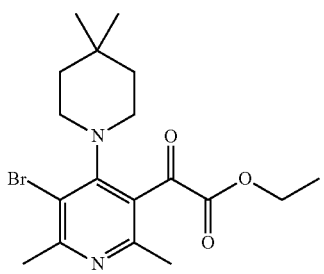 [SMILES: CCOC(=O)C(=O)c1c(C)nc(C)c(Br)c1N1CCC(C)(C)CC1]

Ethyl 2-(5-bromo-4-(4,4-dimethylpiperidin-1-yl)-2,6-dimethylpyridin-3-yl)-2-oxoacetate: To a solution of 4,4-dimethylpiperidine (1.245 g, 11.00 mmol) and DIEA (3.49 ml, 20.00 mmol) in anhydrous CH$_3$CN (40 mL) was added ethyl 2-(5-bromo-4-chloro-2,6-dimethylpyridin-3-yl)-2-oxoacetate (3.21 g, 10 mmol) at rt. The resulting mixture was placed in a pre-heated oil bath (80° C.). After 22 h, the reaction mixture was concentrated and the residue was purified by flash chromatography using 1-lit each 2.5, 5, 7.5 and 10% EtOAc/Hex to afford ethyl 2-(5-bromo-4-(4,4-dimethylpiperidin-1-yl)-2,6-dimethylpyridin-3-yl)-2-oxoacetate (2.846 g, 7.16 mmol, 71.6% yield) as yellow solid. $^1$H NMR (500 MHz, CDCl$_3$) δ 4.37 (q, J=7.1 Hz, 2H), 3.67-2.75 (br.s., 4H), 2.71 (s, 3H), 2.44 (s, 3H), 1.42 (t, J=7.1 Hz, 3H), 1.38 (t, J=5.6 Hz, 4H), 1.00 (s, 6H). LCMS (M+H)=399.4.

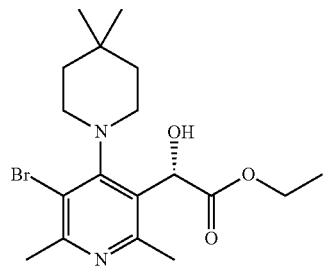 [SMILES: CCOC(=O)[C@@H](O)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-hydroxyacetate: To stirred yellow solution of ethyl 2-(5-bromo-4-(4,4-dimethylpiperidin-1-yl)-2,6-dimethylpyridin-3-yl)-2-oxoacetate (2.25 g, 5.66 mmol) and (R)-1-methyl-3,3-diphenylhexahydropyrrolo[1,2-c][1,3,2]oxazaborole (0.314 g, 1.133 mmol) in toluene (30 mL) at −35° C. was added drop wise 50% catecholborane (1.819 ml, 8.49 mmol) over 10 min. The reaction mixture was slowly warmed to −15° C. over 1 h and then left for 2 h at −15° C. Then, diluted with EtOAc (100 mL), washed with sat Na$_2$CO$_3$ (4×25 mL) by vigorously stirring and separating aqueous layers. The organic layer dried (MgSO$_4$), filtered, concentrated and purified by flash chromatography using 10, 20 and 25% EtOAc/Hex to afford desired (S)-ethyl 2-(5-bromo-4-(4,4-dimethylpiperidin-1-yl)-2,6-dimethylpyridin-3-yl)-2-hydroxyacetate (2.2596 g, 5.66 mmol, 100% yield) contaminated with about 10% of (S)-ethyl 2-(5-bromo-4-chloro-2,6-dimethylpyridin-3-yl)-2-hydroxyacetate. Used in the next step without further purification. $^1$H NMR (500 MHz, CDCl$_3$) δ 5.71 (d, J=7.3 Hz, 1H), 5.54 (d, J=7.4 Hz, 1H), 4.29 (dq, J=10.8, 7.1 Hz, 1H), 4.16 (dq, J=10.8, 7.1 Hz, 1H), 3.94-3.83 (m, 2H), 2.71 (d, J=11.9 Hz, 1H), 2.67 (s, 3H), 2.59 (s, 3H), 2.54 (d, J=12.0 Hz, 1H), 1.71 (td, J=12.7, 4.7 Hz, 1H), 1.62 (td, J=13.0, 4.7 Hz, 1H), 1.42 (dd, J=13.1, 2.2 Hz, 1H), 1.37 (dd, J=12.9, 2.4 Hz, 1H), 1.25 (t, J=7.1 Hz, 3H), 1.09 (s, 3H), 1.04 (s, 3H). LCMS (M+H)=401.3.

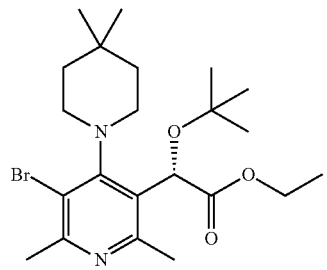 [SMILES: CCOC(=O)[C@@H](OC(C)(C)C)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-(tert-butoxy)acetate: A stirred ice-cold yellow mixture of (S)-ethyl 2-(5-bromo-4-(4,4-dimethylpiperidin-1-yl)-2,6-dimethylpyridin-3-yl)-2-hydroxyacetate (2.45 g, 6.14 mmol) and 70% HClO$_4$ (1.054 ml, 12.27 mmol) in CH$_2$Cl$_2$ (100 mL) was saturated with isobutylene gas by bubbling through the reaction mixture (10 min). After 2 h, cold bath was removed and the turbid reaction mixture stirred for 22 h at rt. LCMS at this point showed 4:1 product to sm. So, saturated with isobutylene (5 min) at rt and stirred for additional 24 h. Then, neutralized with sat. Na$_2$CO$_3$ (30 mL), organic layer separated and aqueous layer extracted with CH$_2$Cl$_2$ (25 mL). The combined organic layers dried (MgSO$_4$), filtered, concentrated and purified by flash chromatography using 5, 10, 15, 20 and 40% EtOAc/hex to afford (S)-ethyl 2-(5-bromo-4-(4,4-dimethylpiperidin-1-yl)-2,6-dimethylpyridin-3-yl)-2-(tert-butoxy)acetate (2.3074 g, 5.07 mmol, 83% yield) as yellow oil: $^1$H NMR (500 MHz, CDCl$_3$) δ 6.19 (br. s., 1H), 4.17-4.24 (m, 1H), 4.08-4.14 (m, 1H), 4.04 (dt, J=2.5, 12.1 Hz, 1H), 3.51 (dt, J=2.5, 12.1 Hz, 1H), 2.85-2.91 (m, 1H), 2.64 (s, 3H), 2.57-2.62 (m, 1H), 2.55 (s, 3H), 1.55-1.66 (m, 2H), 1.41-1.46 (m, 2H), 1.32-1.37 (m, 1H), 1.21 (s, 9H), 1.20 (t, J=7.2 Hz, 3H), 1.08 (s, 3H), 1.03 (s, 3H). LCMS (M+H)=457.4. And (S)-ethyl 2-(5-bromo-4-(4,4-dimethylpiperidin-1-yl)-2,6-dimethylpyridin-3-yl)-2-hydroxyacetate (0.3 g, 0.751 mmol, 12.24% yield) as pale yellow paste: LCMS (M+H)=401.3.

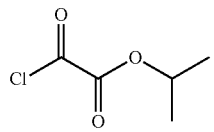

Isopropyl 2-chloro-2-oxoacetate: The propan-2-ol (38.2 mL, 499 mmol) was added drop wise over 15 min to a cold (0° C.), nitrogen purged solution of oxalyl dichloride (101 g, 799 mmol) and the reaction was stirred at room temperature for 2.5 h. Then a reflux condenser was fitted and a slight vacuum was applied for about 1 h until HCl gas was removed (the HCl was trapped in by a sat'd solution of NaHCO$_3$). The reflux condenser was removed and the flask was fitted with a short path distillation head. Excess reagent was removed by distillation under house vacuum (oil bath heated to 65° C.), and then the temperature was raised to between 85-95° C. and the product was distilled (NOTE: The 1$^{st}$ fraction of ~5 mL was discarded) to provide isopropyl 2-chloro-2-oxoacetate 52.62 g (70%).

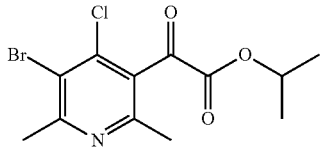 [SMILES: Cc1nc(C)c(C(=O)C(=O)OC(C)C)c(Cl)c1Br]

Isopropyl 2-(5-bromo-4-chloro-2,6-dimethylpyridin-3-yl)-2-oxoacetate: A solution of 2M isopropyl magnesium chloride (84 mL, 168 mmol) was added drop wise over 20 min to a cold (−70° C.), nitrogen purged solution of 3,5-dibromo-4-chloro-2,6-dimethylpyridine (48 g, 160 mmol) and copper(I)bromide-dimethyl sulfide complex (1.65 g, 8.02 mmol) in THF (240 mL), which was then allowed to warm to −10° C. over 60 min. The reaction mixture was transferred via cannula into a 1 L RB-flask containing isopropyl 2-chloro-2-oxoacetate (26.6 g, 176 mmol) in THF (160 mL) maintained at −60° C., and the reaction stirred an additional 2.5 h while being allowed to warm to −10° C. The reaction was quenched upon diluted with a mixture of 10% NH$_4$Cl solution (80 mL) in ether (320 mL). The organic layer was washed with 160 mL of sat'd NaHCO$_3$/10% NH$_4$Cl solution (1:1), brine, and dried (Na$_2$SO$_4$). The crude product was charged (DCM solution) to a 330 g ISCO silica gel cartridge and gradient eluted (5-20% EtOAc/hexanes) using an Isolera chromatography station gave isopropyl 2-(5-bromo-4-chloro-2,6-dimethylpyridin-3-yl)-2-oxoacetate 40.38 g (76%). $^1$H NMR (500 MHz, CDCl$_3$) δ 5.28-5.21 (m, 1H), 2.77 (s, 3H), 2.47 (s, 3H), 1.40 (d, J =6.3 Hz, 6H). LCMS (M+H)=336.04.

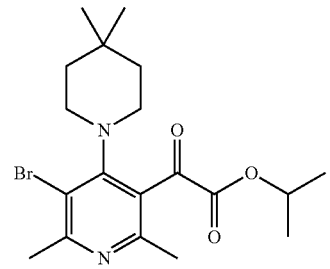 [SMILES: Cc1nc(C)c(C(=O)C(=O)OC(C)C)c(N2CCC(C)(C)CC2)c1Br]

Isopropyl 2-(5-bromo-4-(4,4-dimethylpiperidin-1-yl)-2,6-dimethylpyridin-3-yl)-2-oxoacetate: To a stirred solution of isopropyl 2-(5-bromo-4-chloro-2,6-dimethylpyridin-3-yl)-2-oxoacetate (7.2 g, 21.52 mmol) and DIEA (4.13 mL, 23.67 mmol) in anhydrous acetonitrile (15 mL) was added 4,4-dimethylpiperidine (2.68 g, 23.67 mmol) in acetonitrile (15 mL). The resulting solution was placed in a pre-heated oil bath at 75° C. After heating (75-78° C.) for 24 h and the temperature was raised to 85° C. for 24 h. Another portion of DIEA (3.5 mL, 20.04 mmol) and 4,4-dimethylpiperidine (0.27g, 2.4 mmol) in acetonitrile (3 mL) was added and hearted at 85° C. for a day. The reaction mixture was diluted with ether (100 mL), washed with water (100 mL), brine (50 mL), dried (MgSO$_4$), filtered, concentrated and purified by ISCO 120 g cartridge (EtOAc/hex: 0 to 20%) to afford isopropyl 2-(5-bromo-4-(4,4-dimethylpiperidin-1-yl)-2,6-dimethylpyridin-3-yl)-2-oxoacetate (6.8 g, 16.53 mmol, 77% yield. $^1$H NMR (500 MHz, CDCl$_3$) δ 5.25-5.11 (m, 1H), 3.17 (br. s., 4H), 2.71 (s, 3H), 2.41 (s, 3H), 1.42-1.37 (m, 10H), 1.00 (s, 6H).). LCMS (M+H)=413.3.

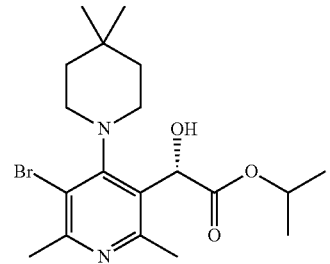 [SMILES: Cc1nc(C)c([C@H](O)C(=O)OC(C)C)c(N2CCC(C)(C)CC2)c1Br]

(S)-Isopropyl 2-(5-bromo-4-(4,4-dimethylpiperidin-1-yl)-2,6-dimethylpyridin-3-yl)-2-hydroxyacetate: To a yellow solution of isopropyl 2-(5-bromo-4-(4,4-dimethylpiperidin-1-yl)-2,6-dimethylpyridin-3-yl)-2-oxoacetate (7.7 g, 18.72 mmol) and (R)-1-methyl-3,3-diphenylhexahydropyrrolo[1,2-c][1,3,2]oxazaborole (7.5 mL, 7.50 mmol) in anhydrous toluene (100 mL) was added drop wise 50% catecholborane/toluene (6 mL, 28.0 mmol) over 5 min at −50° C. Then, the reaction mixture was slowly warmed to −30° C. over 1 h and left in refrigerator (−20° C.) for 3 days. Then, the reaction mixture was diluted with EtOAc (100 mL) and 20 mL of 1M Na$_2$CO$_3$, and vigorously stirred for 30 min. Aqueous layer separated and organic layer washed with sat'd Na$_2$CO$_3$ (2×25 mL) by vigorously stirring for 15 each time, then dried (MgSO$_4$), filtered and concentrated to give crude product as light purple paste which was purified by flash chromatography using 0 to 40% EtOAc/hex to afford (S)-isopropyl 2-(5-bromo-4-(4,4-dimethylpiperidin-1-yl)-2,6-dimethylpyridin-3-yl)-2-hydroxyacetate (6.7 g, 15.72 mmol, 84% yield) as colorless thick paste. ¹H NMR (500 MHz, CDCl₃) δ 5.85 (d, J=5.7 Hz, 1H), 5.59 (d, J=7.4 Hz, 1H), 5.08 (dt, J=12.5, 6.3 Hz, 1H), 3.98-3.88 (m, 1H), 3.88-3.78 (m, 1H), 2.76-2.68 (m, 1H), 2.67 (s, 3H), 2.64-2.58 (m, 1H), 2.57 (s, 3H), 1.73 (td, J=12.8, 4.8 Hz, 1H), 1.65-1.59 (m, 1H), 1.47-1.35 (m, 2H), 1.27 (d, J=6.3 Hz, 3H), 1.17 (d, J=6.1 Hz, 3H), 1.09 (s, 3H), 1.04 (s, 3H). LCMS (M+H)=414.6.

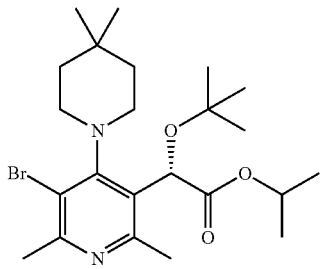 [SMILES: Cc1nc(C)c([C@H](OC(C)(C)C)C(=O)OC(C)C)c(N2CCC(C)(C)CC2)c1Br]

(S)-Isopropyl 2-(5-bromo-4-(4,4-dimethylpiperidin-1-yl)-2,6-dimethylpyridin-3-yl)-2-(tert-butoxy)acetate: A stirred ice-cold yellow mixture of (S)-isopropyl 2-(5-bromo-4-(4,4-dimethylpiperidin-1-yl)-2,6-dimethylpyridin-3-yl)-2-hydroxyacetate (6.7 g, 16.21 mmol) and 70% HClO₄ (2.2 mL, 25.6 mmol) in dichloromethane (400 mL) was saturated with isobutylene gas by bubbling through the reaction mixture (10 min). The reaction mixture was cloudy sealed in a seal tube, stirred for 24 h at rt. The reaction mixture was recooled in a –10° C. bath, bubbled additional isobutylene (~15 min). The reaction mixture became a clear solution at this point. The tube was sealed and stirred at rt for 16 h. LCMs at this point showed incomplete reaction. So, the reaction mixture was cooled down to –30° C. and bubbled isobutene (~15 min). After 24 h, reaction mixture was neutralized with sat. Na₂CO₃ (20 mL), organic layer separated and aqueous layer was extracted with CH₂Cl₂ (25 mL). The combined organic layers were dried (MgSO₄), filtered, concentrated and purified on a ISCO 120 g column (EtOAc/hex: 0 to 40%) to afford (S)-isopropyl 2-(5-bromo-4-(4,4-dimethylpiperidin-1-yl)-2,6-dimethylpyridin-3-yl)-2-(tert-butoxy)acetate (5.43 g, 9.83 mmol, 60.7% yield) as a viscous oil. ¹H NMR (500 MHz, CDCl₃) δ 6.26 (br. s., 1H), 5.09-4.97 (m, 1H), 4.06 (br. s., 1H), 3.51 (br. s., 1H), 2.90 (br. s., 1H), 2.65 (s, 3H), 2.56 (s, 3H), 1.72-1.54 (m, 3H), 1.47 (br. s., 1H), 1.37 (br. s., 1H), 1.23-1.20 (m, 12H), 1.15 (d, J=6.1 Hz, 3H), 1.09 (br. s., 3H), 1.04 (br. s., 3H). LCMS (M+H)=471.3.

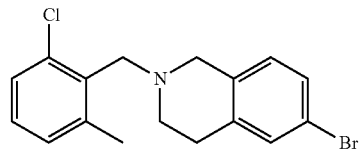 [SMILES: Cc1cccc(Cl)c1CN1CCc2cc(Br)ccc2C1]

6-Bromo-2-(2-chloro-6-methylbenzyl)-1,2,3,4-tetrahydroisoquinoline: To a solution of 6-bromo-1,2,3,4-tetrahydroisoquinoline (1.25 g, 5.88 mmol) in DCM (25 mL) was added 2-chloro-6-methylbenzaldehyde (1.0 g, 6.5 mmol) and acetic acid (0.337 mL, 5.88 mmol) in DCM (25 mL). Then sodium triacetoxyborohydride (1.62 g, 7.64 mmol) was added. The mixture was stirred at r.t for 16 hrs. The mixture was quenched with water and extracted with EtOAc. The organic layer was washed with brine, dried over Na₂SO₄ and concentrated. The residue was purified by recrystallization with EtOAc to give 6-bromo-2-(2-chloro-6-methylbenzyl)-1,2,3,4-tetrahydroisoquinoline (1.44 g, 4.11 mmol, 69.8% yield). LCMS (M+H): 350.00, 352.00. ¹H NMR (400 MHz, DMSO-d₆) δ 7.32-7.14 (m, 5H), 6.99 (d, J=8.1 Hz, 1H), 3.77 (s, 2H), 3.56 (s, 2H), 2.78-2.72 (m, 2H), 2.71-2.66 (m, 2H), 2.41 (s, 3H).

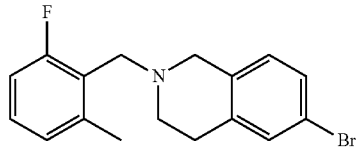

6-Bromo-2-(2-fluoro-6-methylbenzyl)-1,2,3,4-tetrahydroisoquinoline: This compound is prepared by the procedure described above for 6-bromo-2-(2-chloro-6-methylbenzyl)-1,2,3,4-tetrahydroisoquinoline. ¹H NMR (400 MHz, DMSO-d₆) δ 7.30-7.19 (m, 3H), 7.01 (dd, J=17.4, 7.6 Hz, 3H), 3.63 (d, J=2.2 Hz, 2H), 3.52 (s, 2H), 2.79-2.73 (m, 2H), 2.69-2.63 (m, 2H), 2.38 (s, 3H). LCMS (M+H)=336.1

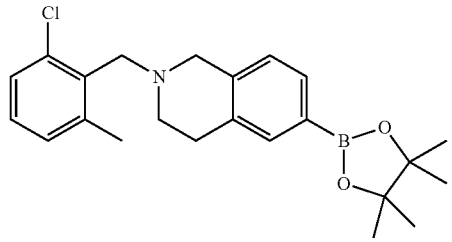 [SMILES: Cc1cccc(Cl)c1CN1CCc2cc(B3OC(C)(C)C(C)(C)O3)ccc2C1]

2-(2-Chloro-6-methylbenzyl)-6-(4,4,5,5-tetramethyl-1,3,2-dioxaborolan-2-yl)-1,2,3,4-tetrahydroisoquinoline: 6-Bromo-2-(2-chloro-6-methylbenzyl)-1,2,3,4-tetrahydroisoquinoline (1.00 g, 2.85 mmol), 4,4,4',4',5,5,5',5'-octamethyl-2,2'-bi(1,3,2-dioxaborolane) (1.09 g, 4.28 mmol), Pd(dppf)Cl₂ (0.209 g, 0.285 mmol) and potassium acetate (0.840 g, 8.55 mmol) were combined in dioxane (10 mL) in a sealed bottle. The mixture was degassed and heated at 85° C. for 8 hrs. The mixture was diluted with EtOAc, washed with water, brine, dried over MgSO₄ and concentrated. The residue was purified by silica gel column (EtOAc/hexanes gradient) to give 2-(2-chloro-6-methylbenzyl)-6-(4,4,5,5-tetramethyl-1,3,2-dioxaborolan-2-yl)-1,2,3,4-tetrahydroisoquinoline (1.05 g, 2.64 mmol, 93% yield). 1H NMR (400 MHz, CDCl₃) δ 7.57-7.51 (m, 2H), 7.23 (d, J=7.6 Hz, 1H), 7.14-7.06 (m, 2H), 7.02 (d, J=7.6 Hz, 1H), 3.83 (s, 2H), 3.71 (s, 2H), 2.88-2.76 (m, 4H), 2.46 (s, 3H), 1.34 (s, 12H). LCMS (M+H): 398.05.

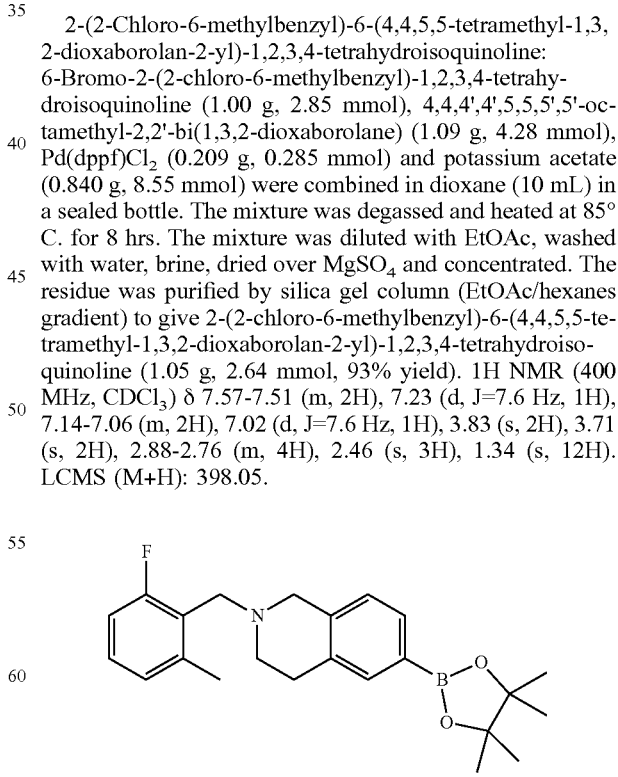

2-(2-Fluoro-6-methylbenzyl)-6-(4,4,5,5-tetramethyl-1,3,2-dioxaborolan-2-yl)-1,2,3,4-tetrahydroisoquinoline: This compound is prepared using 6-bromo-2-(2-fluoro-6-methylbenzyl)-1,2,3,4-tetrahydroisoquinoline by following the procedure described above for 2-(2-chloro-6-methylbenzyl)-6-(4,4,5,5-tetramethyl-1,3,2-dioxaborolan-2-yl)-1,2,3,4-tetrahydroisoquinoline. LCMS (M+H)=382.2.

Preparation of Intermediates (S)-ethyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate and (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid from (S)-ethyl 2-(5-bromo-4-(4,4-dimethylpiperidin-1-yl)-2,6-dimethylpyridin-3-yl)-2-(tert-butoxy)acetate

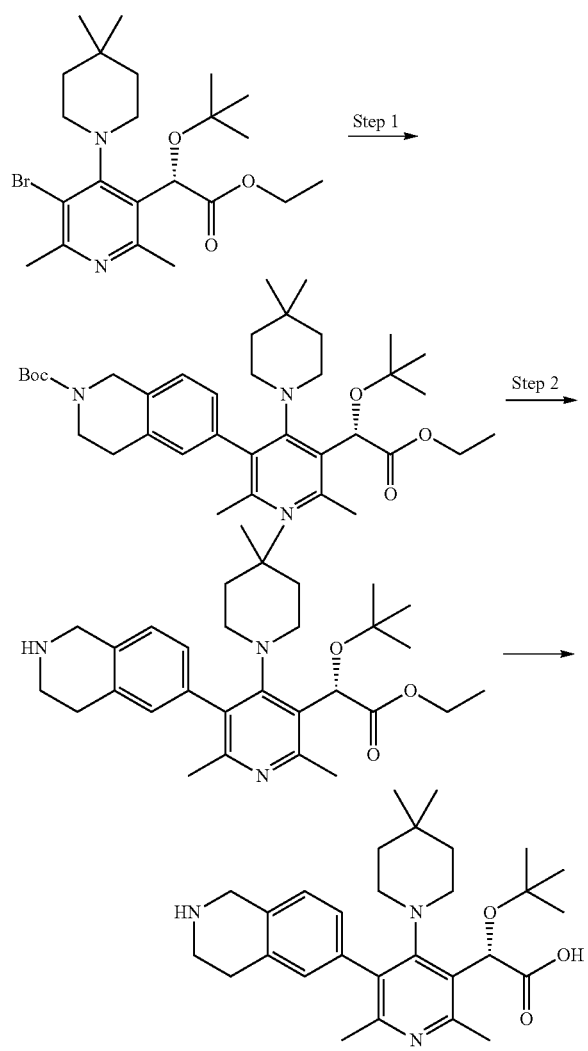

Step 1: To a mixture of (S)-ethyl 2-(5-bromo-4-(4,4-dimethylpiperidin-1-yl)-2,6-dimethylpyridin-3-yl)-2-(tert-butoxy)acetate (500 mg), (2-(tert-butoxycarbonyl)-1,2,3,4-tetrahydroisoquinolin-6-yl)boronic acid (365 mg) and $Cs_2CO_3$ (715 mg) in 1,4-dioxane (25 mL) and water (5 mL) was added $Pd(PPh_3)_4$ (127 mg). The mixture was flushed with nitrogen and then heated at 85° C. for 3 hours. The mixture was diluted with water (20 mL) and then extracted with EtOAc (2×20 mL). The organic layers were combined, washed with brine and concentrated under vaccum to give a crude of (S)-tert-butyl 6-(5-(1-(tert-butoxy)-2-ethoxy-2-oxoethyl)-4-(4,4-dimethylpiperidin-1-yl)-2,6-dimethylpyridin-3-yl)-3,4-dihydroisoquinoline-2(1H)-carboxylate which was used as was. LCMS: MS (M+H)+ calcd. 608.4; observ. 608.5.

Step 2: To a solution of (S)-tert-butyl 6-(5-(1-(tert-butoxy)-2-ethoxy-2-oxoethyl)-4-(4,4-dimethylpiperidin-1-yl)-2,6-dimethylpyridin-3-yl)-3,4-dihydroisoquinoline-2(1H)-carboxylate (200 mg) in $CH_2Cl_2$ (20 mL) was added TFA (1 mL). The reaction was stirred at room temperature for 3 hours. All the solvents were removed under vacuum to give rude (S)-ethyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate which was used without further purification. LCMS: MS (M+H)+ calcd. 508.4; observ. 508.3.

Step 3: To a solution of (S)-ethyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate (10 mg) in MeOH (1 mL) and THF (1 mL) was added sodium hydroxide (0.158 mL, 1N). The reaction was stirred at 80° C. for 2 hours. The mixture was acidified by 1N HCl to pH ~4. All the solvents were removed under vacuum to give a residue was prified by preparative HPLC system. LCMS: MS (M+H)+ calcd. 480.3; observ. 480.3.

Preparation of Intermediates (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate and (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid from (S)-isopropyl 2-(5-bromo-4-(4,4-dimethylpiperidin-1-yl)-2,6-dimethylpyridin-3-yl)-2-(tert-butoxy)acetate

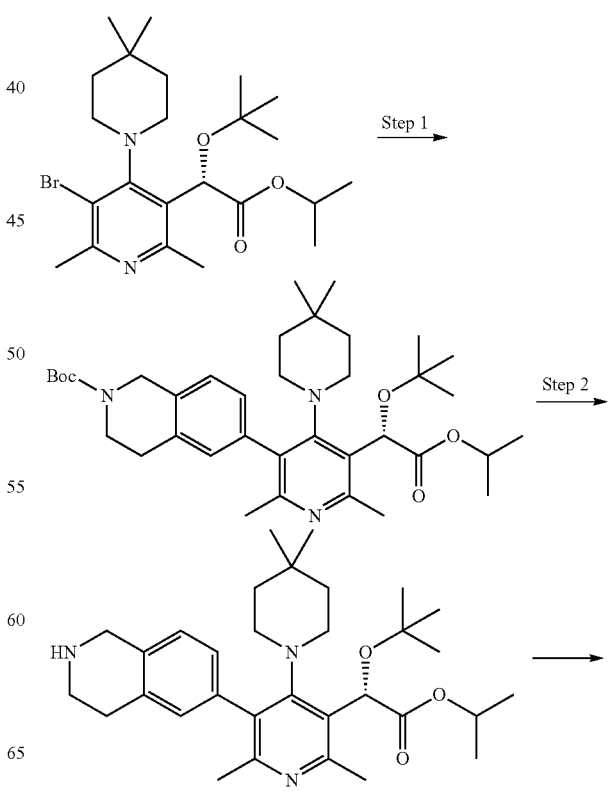

-continued

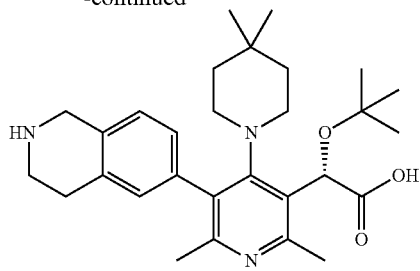

Step 1: To a mixture of (S)-isopropyl 2-(5-bromo-4-(4,4-dimethylpiperidin-1-yl)-2,6-dimethylpyridin-3-yl)-2-(tert-butoxy)acetate (1.1 g), (2-(tert-butoxycarbonyl)-1,2,3,4-tetrahydroisoquinolin-6-yl)boronic acid (0.649 g) and Cs$_2$CO$_3$ (1.527 g) in 1,4-dioxane (40 mL) and water (8 mL) was added Pd(PPh$_3$)$_4$ (0.271 g). The mixture was flushed with nitrogen and then heated at 85° C. for 5 hours. The mixture was diluted with water (50 mL) and then extracted with EtOAc (2×50 mL). The organic layers were combined, washed with brine and concentrated under vaccum to give a residue which was purified by silica gel chromatography (hexane/EtOAc=10:1 to 3:1) to give (S)-tert-butyl 6-(5-(1-(tert-butoxy)-2-isopropoxy-2-oxoethyl)-4-(4,4-dimethylpiperidin-1-yl)-2,6-dimethylpyridin-3-yl)-3,4-dihydroisoquinoline-2(1H)-carboxylate. LCMS: MS (M+H)$^+$ calcd. 622.4; observ. 622.4.

Step 2: To a solution of (S)-tert-butyl 6-(5-(1-(tert-butoxy)-2-isopropoxy-2-oxoethyl)-4-(4,4-dimethylpiperidin-1-yl)-2,6-dimethylpyridin-3-yl)-3,4-dihydroisoquinoline-2(1H)-carboxylate (420 mg) in CH$_2$Cl$_2$ (5 mL) was added TFA (1 mL). The reaction mixture was stirred at room temperature for 4 hours. All the solvents were removed under vacuum to give (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate which was used without further purification. LCMS: MS (M+H)$^+$ calcd. 522.4; observ. 522.3.

Step 3: To a solution of (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate (50 mg) in ethanol (4 mL) was added KOH (43.0 mg) and water (0.4 mL). The reaction mixture was heated at 85° C. for 6 hours. The mixture was acidified by 1N HCl to pH=4. All the solvents were removed under vaccum. The residue was used without further purification. LCMS: MS (M+H)$^+$ calcd. 480.3; observ. 480.2.

General Procedure A for the preparation of Claim I, from (S)-ethyl or (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate

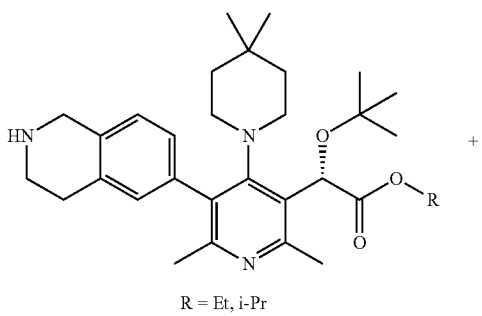

R = Et, i-Pr

-continued

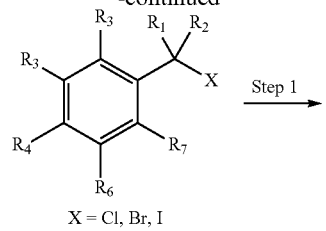

X = Cl, Br, I

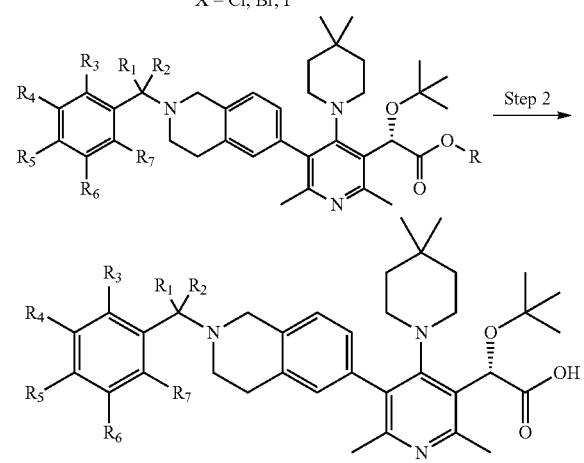

Claim I

Step 1: Na$_2$CO$_3$ or K$_2$CO$_3$ or Cs$_2$CO$_3$ or NaH (1-20 eq.) was added into a solution of (S)-ethyl of (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate (1 eq.) and an electrophile (1-20 eq.) in acetonitrile or THF or DMF or dioxane. The reaction was carried out at room temperature or at an increased temperature (up to 150° C.) for a period of time (10 minutes to 72 hours). After removal of solvents under vaccum, the residue was used as was or purified by the preparative HPLC system.

Step 2: To a solution of the product from the step 1 (1 eq.) in MeOH or EtOH and THF (volume ratio 20:1 to 1:20) was added NaOH or KOH (1 to 100 eq.). The reaction was carried out at room temperature or at an increased temperature (up to 150° C.) for a period of time (10 minutes to 72 hours). The mixture was acidified by 1N HCl to pH ~4. Removal of the solvents under vaccum gave a residue which was purified by the preparative HPLC system.

General Procedure B for the preparation of Claim I, from (S)-ethyl or (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate

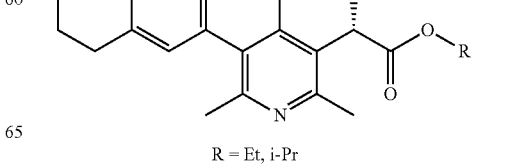

R = Et, i-Pr

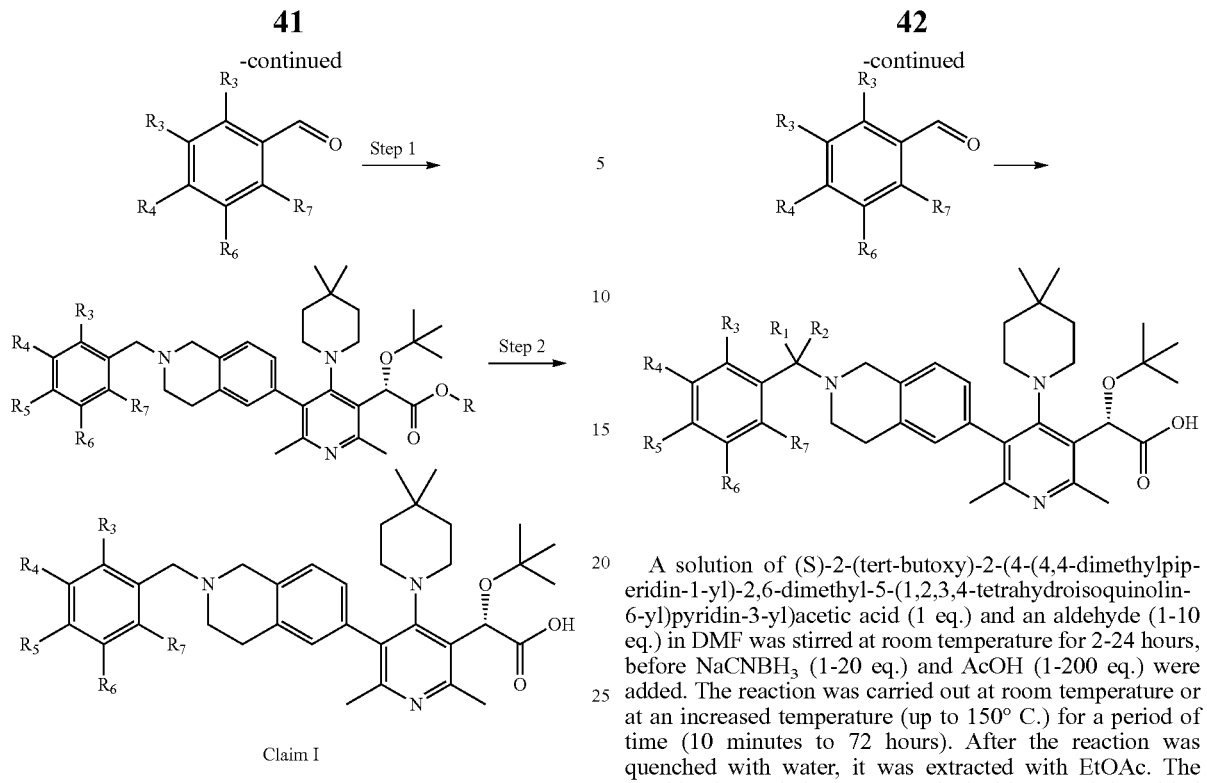

Claim I

Step 1: A solution of (S)-Ethyl or (S)-isopropyl 2-(tert-butoxy)-2-(4-(4,4-dimethylpiperidin-1-yl)-2,6-dimethyl-5-(1,2,3,4-tetrahydroisoquinolin-6-yl)pyridin-3-yl)acetate (1 eq.) and an aldehyde (1-10 eq.) in DMF was stirred at room temperature for 2-24 hours, before NaCNBH$_3$ (1-20 eq.) and AcOH (1-200 eq.) were added. The reaction was carried out at room temperature or at an increased temperature (up to 150° C.) for a period of time (10 minutes to 72 hours). After the reaction was quenched with water, it was extracted with EtOAc. The combined organic layer was washed with water, brine, dried over MgSO$_4$ and concentrated under vaccum. The residue was used as was or purified by the preparative HPLC system.

Step 2: To a solution of the product from the step 1 (1 eq.) in MeOH or EtOH and THF (volume ratio 20:1 to 1:20) was added NaOH or KOH (1 to 100 eq.). The reaction was carried out at room temperature or at an increased temperature (up to 150° C.) for a period of time (10 minutes to 72 hours). The mixture was acidified by 1N HCl to pH ~4. Removal of the solvents under vaccum gave a residue which was purified by the preparative HPLC system.

General Procedure C for the preparation of Claim I, from (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid

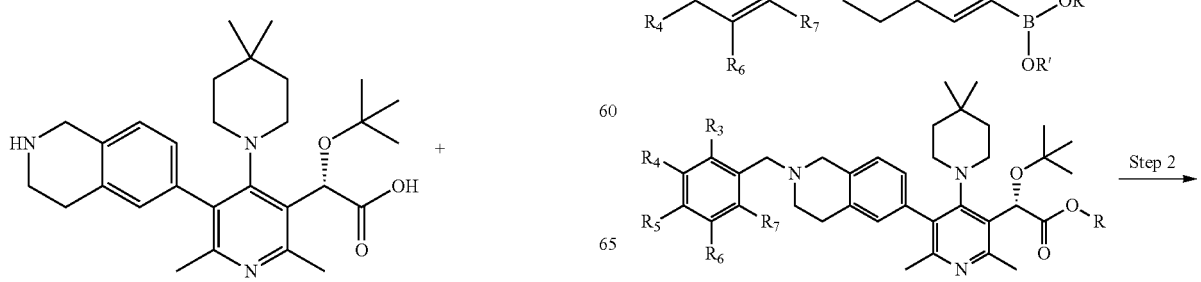

A solution of (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid (1 eq.) and an aldehyde (1-10 eq.) in DMF was stirred at room temperature for 2-24 hours, before NaCNBH$_3$ (1-20 eq.) and AcOH (1-200 eq.) were added. The reaction was carried out at room temperature or at an increased temperature (up to 150° C.) for a period of time (10 minutes to 72 hours). After the reaction was quenched with water, it was extracted with EtOAc. The combined organic layer was washed with water, brine, dried over MgSO$_4$ and concentrated under vaccum. The residue was used as was or purified by the preparative HPLC system.

General Procedure D for the preparation of Claim I, from (S)-2-(tert-butoxy)-2-(4-(4,4-dimethylpiperidin-1-yl)-2,6-dimethyl-5-(1,2,3,4-tetrahydroisoquinolin-6-yl)pyridin-3-yl)acetic acid

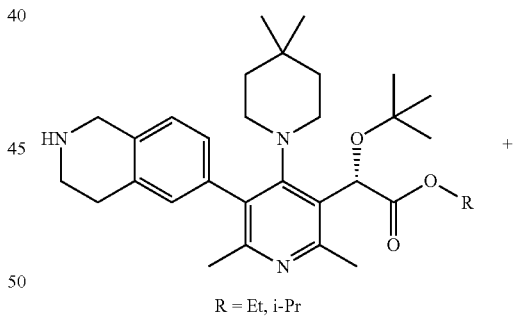

R = Et, i-Pr

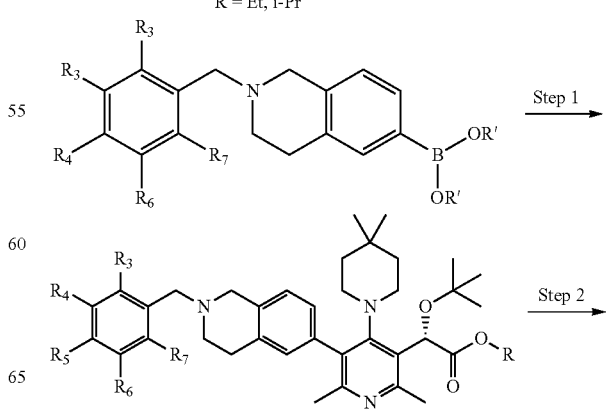

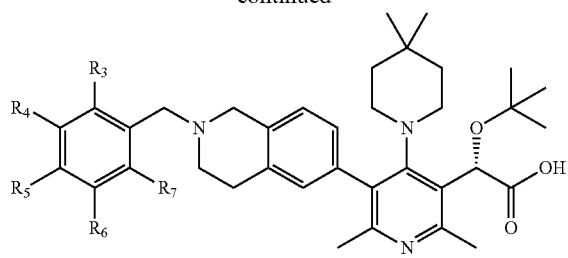

Claim I

Step 1: To a mixture of (S)-isopropyl 2-(5-bromo-4-(4,4-dimethylpiperidin-1-yl)-2,6-dimethylpyridin-3-yl)-2-(tert-butoxy)acetate (1 equiv), 2-(arylalkyl)-6-(4,4,5,5-tetramethyl-1,3,2-dioxaborolan-2-yl)-1,2,3,4-tetrahydroisoquinoline (1 to 5 equiv.) and cesium carbonat (2 to 10 equiv.) in 1,4-dioxane/water was added Pd(Ph₃P)₄ (0.1 to 1 equiv.). The mixture was flushed with nitrogen and then heated at 90° C. until reaction complete (1 to 24 h). The mixture was diluted with water and then extracted with EtOAc. The organic layers were combined, washed with brine and concentrated to give a residue, which was purified by silicagel column (EtOAc/Hex; gradient elution) to give (S)-isopropyl 2-(tert-butoxy)-2-(4-(4,4-dimethylpiperidin-1-yl)-5-(2-(arylalkyl)-1,2,3,4-tetrahydroisoquinolin-6-yl)-2,6-dimethylpyridin-3-yl)acetate Step 2: To a solution of the product from the step 1 (1 eq.) in MeOH or EtOH and THF (volume ratio 20:1 to 1:20) was added NaOH or KOH (1 to 100 eq.). The reaction was carried out at room temperature or at an increased temperature (up to 150° C.) for a period of time (10 minutes to 72 hours). The mixture was acidified by 1N HCl to pH ~4. Removal of the solvents under vaccum gave a residue which was purified by the preparative HPLC system.

| Compound | Name<br>General Method Used<br>Structure | LCMS<br>(M + H)⁺ |
| --- | --- | --- |
| 1 | (S)-2-(tert-butoxy)-2-(4-(4,4-dimethylpiperidin-1-yl)-5-(2-(4-fluorobenzyl)-1,2,3,4-tetrahydroisoquinolin-6-yl)-2,6-dimethylpyridin-3-yl)acetic acid | |
| | 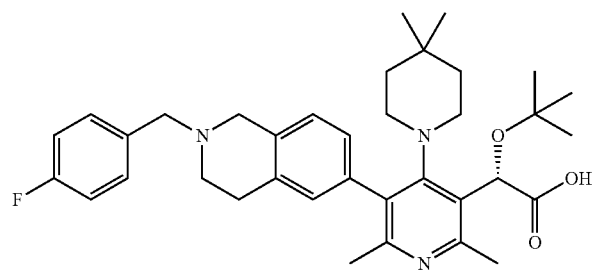 [SMILES: Cc1nc(C)c([C@H](OC(C)(C)C)C(=O)O)c(N2CCC(C)(C)CC2)c1-c1ccc2c(c1)CCN(Cc1ccc(F)cc1)C2] | |
| | Method A: LCMS (M + H) = 588.7 | |
| 2 | (S)-2-(tert-butoxy)-2-(4-(4,4-dimethylpiperidin-1-yl)-2,6-dimethyl-5-(2-(3-(trifluoromethyl)benzyl)-1,2,3,4-tetrahydroisoquinolin-6-yl)pyridin-3-yl)acetic acid | |
| | 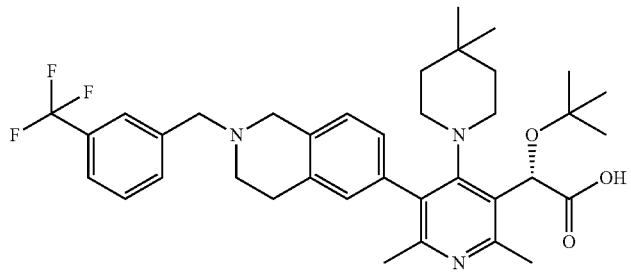 [SMILES: Cc1nc(C)c([C@H](OC(C)(C)C)C(=O)O)c(N2CCC(C)(C)CC2)c1-c1ccc2c(c1)CCN(Cc1cccc(C(F)(F)F)c1)C2] | |
| | Method A: LCMS (M + H) = 638.8 | |
| 3 | (S)-2-(tert-butoxy)-2-(4-(4,4-dimethylpiperidin-1-yl)-2,6-dimethyl-5-(2-(3-methylbenzyl)-1,2,3,4-tetrahydroisoquinolin-6-yl)pyridin-3-yl)acetic acid | |

| Compound | Name<br>General Method Used<br>Structure | LCMS<br>(M + H)+ |
|---|---|---|

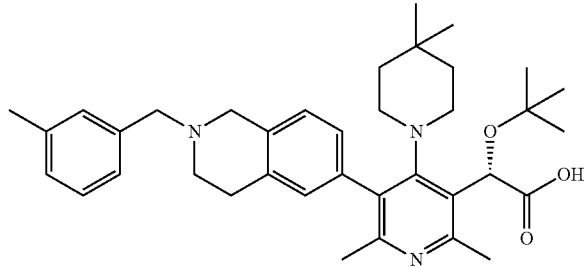 [SMILES: Cc1cccc(CN2CCc3cc(-c4c(C)nc(C)c([C@H](OC(C)(C)C)C(=O)O)c4N4CCC(C)(C)CC4)ccc3C2)c1]

Method A: LCMS (M + H) = 584.8

4     (S)-2-(tert-butoxy)-2-(4-(4,4-dimethylpiperidin-1-yl)-2,6-dimethyl-5-(2-(2-methylbenzyl)-1,2,3,4-tetrahydroisoquinolin-6-yl)pyridin-3-yl)acetic acid

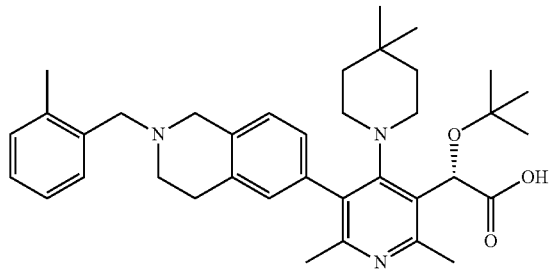 [SMILES: Cc1ccccc1CN1CCc2cc(-c3c(C)nc(C)c([C@H](OC(C)(C)C)C(=O)O)c3N3CCC(C)(C)CC3)ccc2C1]

Method A: LCMS (M + H) = 584.2

5     (S)-2-(tert-butoxy)-2-(4-(4,4-dimethylpiperidin-1-yl)-2,6-dimethyl-5-(2-(4-methylbenzyl)-1,2,3,4-tetrahydroisoquinolin-6-yl)pyridin-3-yl)acetic acid

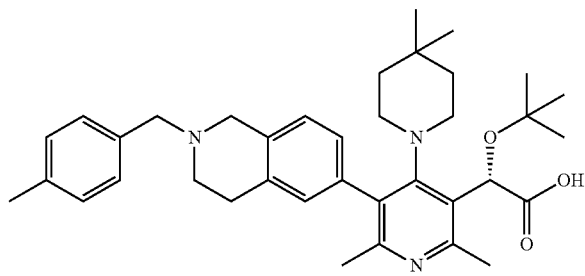 [SMILES: Cc1ccc(CN2CCc3cc(-c4c(C)nc(C)c([C@H](OC(C)(C)C)C(=O)O)c4N4CCC(C)(C)CC4)ccc3C2)cc1]

Method A: LCMS (M + H) = 584.4

6     (S)-2-(tert-butoxy)-2-(4-(4,4-dimethylpiperidin-1-yl)-5-(2-(3-methoxybenzyl)-1,2,3,4-tetrahydroisoquinolin-6-yl)-2,6-dimethylpyridin-3-yl)acetic acid

| Compound | Name<br>General Method Used<br>Structure | LCMS<br>(M + H)+ |
|---|---|---|
| | 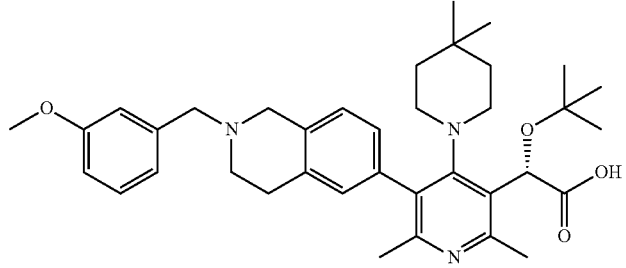 [SMILES: COc1cccc(CN2CCc3cc(-c4c(C)nc(C)c([C@H](OC(C)(C)C)C(=O)O)c4N4CCC(C)(C)CC4)ccc3C2)c1]<br>Method A: LCMS (M + H) = 600.3 | |
| 7 | (S)-2-(tert-butoxy)-2-(4-(4,4-dimethylpiperidin-1-yl)-5-(2-(3-fluorobenzyl)-1,2,3,4-tetrahydroisoquinolin-6-yl)-2,6-dimethylpyridin-3-yl)acetic acid | |
| | 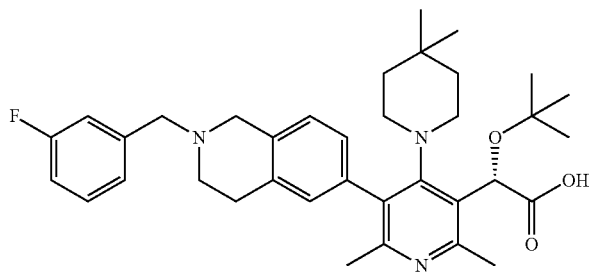<br>Method A: LCMS (M + H) = 588.2 | |
| 8 | (S)-2-(tert-butoxy)-2-(4-(4,4-dimethylpiperidin-1-yl)-2,6-dimethyl-5-(2-(4-(trifluoromethyl)benzyl)-1,2,3,4-tetrahydroisoquinolin-6-yl)pyridin-3-yl)acetic acid | |
| | 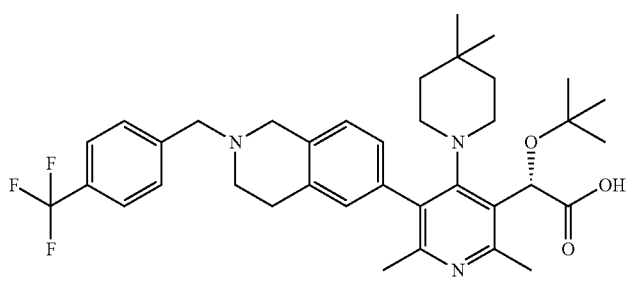 [SMILES: Cc1nc(C)c([C@H](OC(C)(C)C)C(=O)O)c(N2CCC(C)(C)CC2)c1-c1ccc2c(c1)CCN(Cc1ccc(C(F)(F)F)cc1)C2]<br>Method A: LCMS (M + H) = 638.4 | |
| 9 | (S)-2-(tert-butoxy)-2-(4-(4,4-dimethylpiperidin-1-yl)-5-(2-(2-fluorobenzyl)-1,2,3,4-tetrahydroisoquinolin-6-yl)-2,6-dimethylpyridin-3-yl)acetic acid | |

| Compound | Name<br>General Method Used<br>Structure | LCMS<br>(M + H)+ |
|---|---|---|
| | 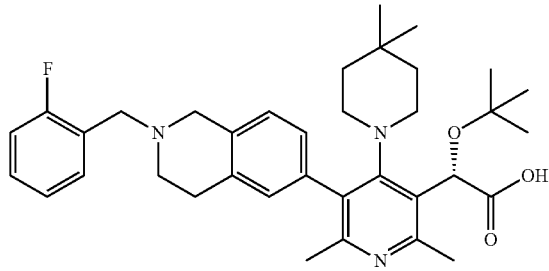<br>Method A: LCMS (M + H) = 588.8 | |
| 10 | (S)-3-((6-(5-(tert-butoxy(carboxy)methyl)-4-(4,4-dimethylpiperidin-1-yl)-2,6-dimethylpyridin-3-yl)-3,4-dihydroisoquinolin-2(1H)-yl)methyl)benzoic acid | |
| | 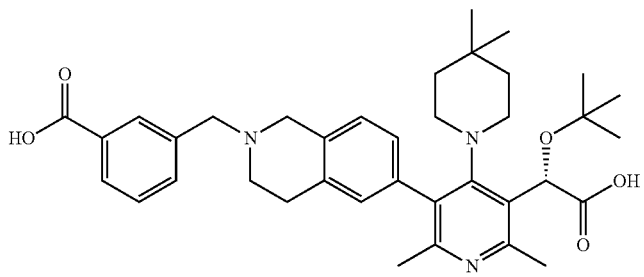 [SMILES: Cc1nc(C)c([C@H](OC(C)(C)C)C(=O)O)c(N2CCC(C)(C)CC2)c1-c1ccc2c(c1)CCN(Cc1cccc(C(=O)O)c1)C2]<br>Method A: LCMS (M + H) = 614.2 | |
| 11 | (S)-2-(5-(2-([1,1'-biphenyl]-3-ylmethyl)-1,2,3,4-tetrahydroisoquinolin-6-yl)-4-(4,4-dimethylpiperidin-1-yl)-2,6-dimethylpyridin-3-yl)-2-(tert-butoxy)acetic acid | |
| | 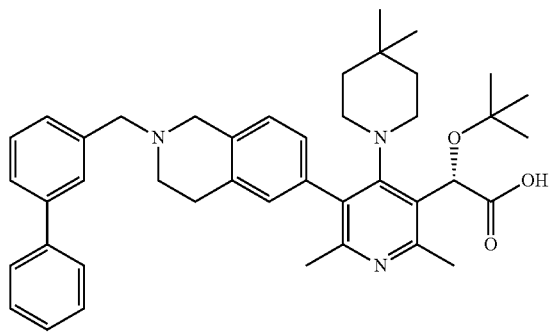 [SMILES: Cc1nc(C)c([C@H](OC(C)(C)C)C(=O)O)c(N2CCC(C)(C)CC2)c1-c1ccc2c(c1)CCN(Cc1cccc(-c3ccccc3)c1)C2]<br>Method A: LCMS (M + H) = 646.4 | |
| 12 | (S)-2-(tert-butoxy)-2-(4-(4,4-dimethylpiperidin-1-yl)-2,6-dimethyl-5-(2-(2-(trifluoromethyl)benzyl)-1,2,3,4-tetrahydroisoquinolin-6-yl)pyridin-3-yl)acetic acid | |

| Compound | Name / General Method Used / Structure | LCMS (M + H)+ |
|---|---|---|
| | 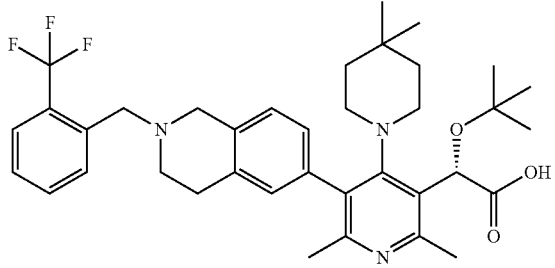 [SMILES: Cc1nc(C)c([C@H](OC(C)(C)C)C(=O)O)c(N2CCC(C)(C)CC2)c1-c1ccc2c(c1)CCN(Cc1ccccc1C(F)(F)F)C2]<br>Method A: LCMS (M + H) = 638.3 | |
| 13 | (2S)-2-(tert-butoxy)-2-(4-(4,4-dimethylpiperidin-1-yl)-2,6-dimethyl-5-(2-(1-phenylethyl)-1,2,3,4-tetrahydroisoquinolin-6-yl)pyridin-3-yl)acetic acid | |
| | 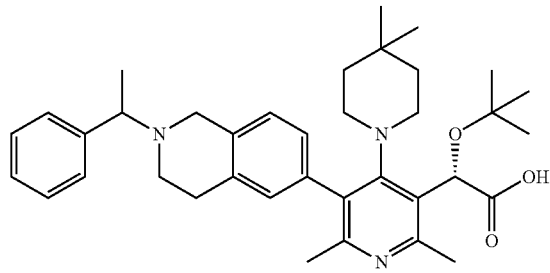 [SMILES: Cc1nc(C)c([C@H](OC(C)(C)C)C(=O)O)c(N2CCC(C)(C)CC2)c1-c1ccc2c(c1)CCN(C(C)c1ccccc1)C2]<br>Method A: LCMS (M + H) = 584.3 | |
| 14 | (S)-2-(5-(2-([1,1'-biphenyl]-4-ylmethyl)-1,2,3,4-tetrahydroisoquinolin-6-yl)-4-(4,4-dimethylpiperidin-1-yl)-2,6-dimethylpyridin-3-yl)-2-(tert-butoxy)acetic acid | |
| | 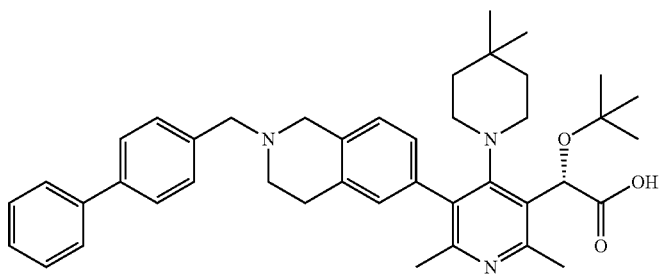 [SMILES: Cc1nc(C)c([C@H](OC(C)(C)C)C(=O)O)c(N2CCC(C)(C)CC2)c1-c1ccc2c(c1)CCN(Cc1ccc(-c3ccccc3)cc1)C2]<br>Method A: LCMS (M + H) = 646.4 | |
| 15 | (S)-2-(tert-butoxy)-2-(4-(4,4-dimethylpiperidin-1-yl)-2,6-dimethyl-5-(2-(2-methyl-3-(trifluoromethyl)benzyl)-1,2,3,4-tetrahydroisoquinolin-6-yl)pyridin-3-yl)acetic acid | |

| Compound | Name<br>General Method Used<br>Structure | LCMS<br>(M + H)+ |
|---|---|---|
| | 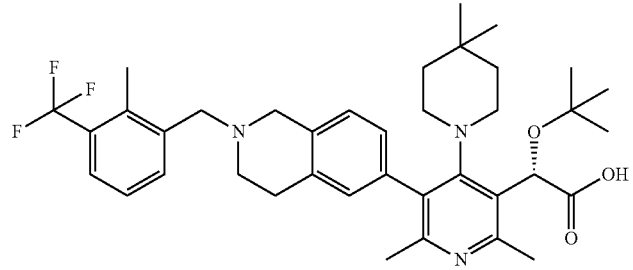<br>Method A: LCMS (M + H) = 652.1 | |
| 16 | (S)-2-(tert-butoxy)-2-(4-(4,4-dimethylpiperidin-1-yl)-2,6-dimethyl-5-(2-(4-methyl-3-(trifluoromethyl)benzyl)-1,2,3,4-tetrahydroisoquinolin-6-yl)pyridin-3-yl)acetic acid | |
| | 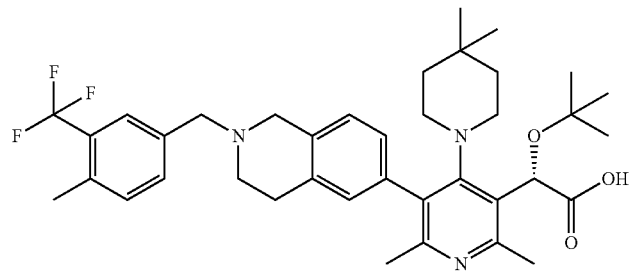 [SMILES: Cc1ccc(CN2CCc3cc(-c4c(C)nc(C)c([C@H](OC(C)(C)C)C(=O)O)c4N4CCC(C)(C)CC4)ccc3C2)cc1C(F)(F)F]<br>Method A: LCMS (M + H) = 652.1 | |
| 17 | (S)-2-(tert-butoxy)-2-(5-(2-(3,4-dimethylbenzyl)-1,2,3,4-tetrahydroisoquinolin-6-yl)-4-(4,4-dimethylpiperidin-1-yl)-2,6-dimethylpyridin-3-yl)acetic acid | |
| | 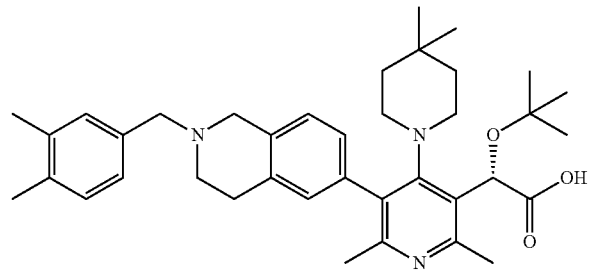 [SMILES: Cc1ccc(CN2CCc3cc(-c4c(C)nc(C)c([C@H](OC(C)(C)C)C(=O)O)c4N4CCC(C)(C)CC4)ccc3C2)cc1C]<br>Method A: LCMS (M + H) = 598.1 | |
| 18 | (S)-2-(tert-butoxy)-2-(4-(4,4-dimethylpiperidin-1-yl)-5-(2-(3-fluoro-4-methylbenzyl)-1,2,3,4-tetrahydroisoquinolin-6-yl)-2,6-dimethylpyridin-3-yl)acetic acid | |

-continued

| Compound | Name
General Method Used
Structure | LCMS
(M + H)+ |
|---|---|---|

Method A: LCMS (M + H) = 602.3

19     (S)-2-(tert-butoxy)-2-(5-(2-(2,4-dimethylbenzyl)-1,2,3,4-tetrahydroisoquinolin-6-yl)-4-(4,4-dimethylpiperidin-1-yl)-2,6-dimethylpyridin-3-yl)acetic acid Method A: LCMS (M + H) = 598.5

20     (S)-2-(tert-butoxy)-2-(5-(2-(2,4-difluorobenzyl)-1,2,3,4-tetrahydroisoquinolin-6-yl)-4-(4,4-dimethylpiperidin-1-yl)-2,6-dimethylpyridin-3-yl)acetic acid Method C: $^1$H NMR (500 MHz, DMSO-$d_6$) δ 7.56-7.49 (m, 1H), 7.23 (t, J = 9.7 Hz, 1H), 7.12-7.03 (m, 3H), 6.88 (s, 1H), 5.82 (d, J = 10.6 Hz, 1H), 3.71 (s, 2H), 3.64 (br. s., 2H), 3.32 (br. s., 1H), 2.89 (s, 1H), 2.83 (d, J = 4.8 Hz, 2H), 2.74-2.70 (m, 2H), 2.54 (s, 1H), 2.42 (s, 3H), 2.09-2.04 (m, 3H), 1.90 (s, 6H), 1.11 (s, 9H), 0.84 (br. s., 3H), 0.60 (br. s., 3H). LCMS (M + H) = 606.3

21     (S)-2-(tert-butoxy)-2-(5-(2-(2,3-difluorobenzyl)-1,2,3,4-tetrahydroisoquinolin-6-yl)-4-(4,4-dimethylpiperidin-1-yl)-2,6-dimethylpyridin-3-yl)acetic acid

| Compound | Name<br>General Method Used<br>Structure | LCMS<br>(M + H)+ |
|---|---|---|

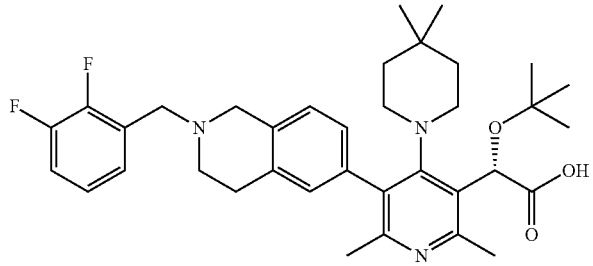 [SMILES: Cc1nc(C)c([C@H](OC(C)(C)C)C(=O)O)c(N2CCC(C)(C)CC2)c1-c1ccc2c(c1)CCN(Cc1cccc(F)c1F)C2]

Method C: ¹H NMR (500 MHz, DMSO-d₆) δ 7.40-7.28 (m, 2H), 7.22 (d, J = 5.5 Hz, 1H), 7.16-7.08 (m, 1H), 7.07-7.01 (m, 1H), 6.88 (s, 1H), 5.79 (d, J = 10.3 Hz, 1H), 3.81-3.75 (m, 2H), 3.66 (br. s., 2H), 3.40-3.36 (m, 1H), 2.91-2.68 (m, 6H), 2.54 (s, 1H), 2.42 (s, 3H), 2.12-2.01 (m, 3H), 1.90 (s, 5H), 1.11 (s, 9H), 0.84 (br. s., 3H), 0.60 (br. s., 3H). LCMS (M + H) = 606.3

22   (S)-2-(tert-butoxy)-2-(5-(2-(4-chloro-3-fluorobenzyl)-1,2,3,4-tetrahydroisoquinolin-6-yl)-4-(4,4-dimethylpiperidin-1-yl)-2,6-dimethylpyridin-3-yl)acetic acid

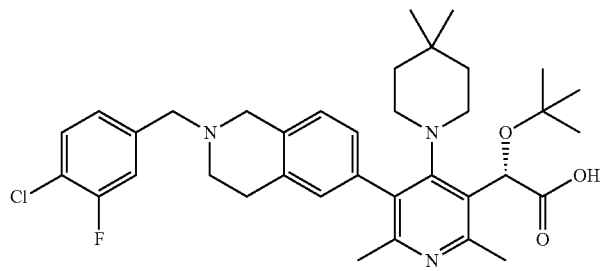 [SMILES: Cc1nc(C)c([C@H](OC(C)(C)C)C(=O)O)c(N2CCC(C)(C)CC2)c1-c1ccc2c(c1)CCN(Cc1ccc(Cl)c(F)c1)C2]

Method C: LCMS (M + H) = 622.3

23   (S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-2,6-dimethylpyridin-3-yl)acetic acid

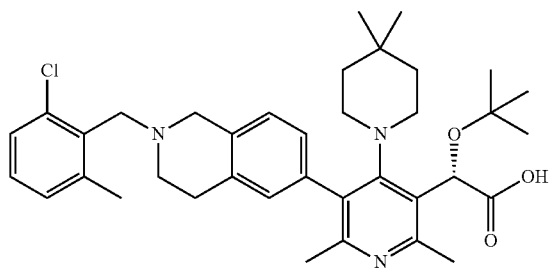

Method C, D: ¹H NMR (500 MHz, METHANOL-d₄) δ 7.32-7.25 (m, 1H), 7.25-7.07 (m, 4H), 6.99-6.90 (m, 1H), 5.60-5.41 (m, 1H), 3.94 (s, 2H), 3.80 (s, J = 15.1 Hz, 2H), 2.91 (m, 4H), 2.81-2.60 (m, 7H), 2.52 (s, 3H), 2.31 (s, 3H), 1.35 (br. s., 4H), 1.20 (s, 9H), 0.85 (s, 6H). LCMS (M + H) = 618.3

24   (S)-2-(tert-butoxy)-2-(5-(2-(3-chloro-4-fluorobenzyl)-1,2,3,4-tetrahydroisoquinolin-6-yl)-4-(4,4-dimethylpiperidin-1-yl)-2,6-dimethylpyridin-3-yl)acetic acid

| Compound | Name / General Method Used / Structure | LCMS (M + H)+ |
|---|---|---|
| | Method C: ¹H NMR (500 MHz, DMSO-d₆) δ 7.60-7.53 (m, 1H), 7.39 (d, J = 8.8 Hz, 2H), 7.15-7.02 (m, 2H), 6.90-6.84 (m, 1H), 5.82 (d, J = 11.0 Hz, 1H), 3.70-3.58 (m, 4H), 2.91-2.66 (m, 8H), 2.42 (s, 3H), 2.12-2.04 (m, 3H), 1.90 (s, 4H), 1.11 (s, 9H), 0.85 (br. s., 3H), 0.61 (br. s., 3H). LCMS (M + H) = 622.3 | |
| 25 | (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2,6-dimethylpyridin-3-yl)acetic acid | |
| | Method C: ¹H NMR (500 MHz, DMSO-d₆) δ 7.36-7.26 (m, 1H), 7.13-6.93 (m, 4H), 6.85 (br. s., 1H), 5.77 (d, J = 12.5 Hz, 1H), 3.59 (br. s., 4H), 2.90-2.66 (m, 6H), 2.42 (s, 3H), 2.35 (br. s., 3H), 2.12-2.03 (m, 3H), 1.90 (s, 7H), 1.10 (br. s., 9H), 0.84 (br. s., 3H), 0.59 (br. s., 3H). LCMS (M + H) = 602.4 | |
| 26 | (S)-2-(tert-butoxy)-2-(5-(2-(3,5-dichlorobenzyl)-1,2,3,4-tetrahydroisoquinolin-6-yl)-4-(4,4-dimethylpiperidin-1-yl)-2,6-dimethylpyridin-3-yl)acetic acid | |
| | Method A: LCMS (M + H) = 638.4 | |
| 27 | (S)-2-(tert-butoxy)-2-(5-(2-(4-(tert-butyl)benzyl)-1,2,3,4-tetrahydroisoquinolin-6-yl)-4-(4,4-dimethylpiperidin-1-yl)-2,6-dimethylpyridin-3-yl)acetic acid | |

-continued

| Compound | Name<br>General Method Used<br>Structure | LCMS<br>(M + H)+ |
|---|---|---|
| | 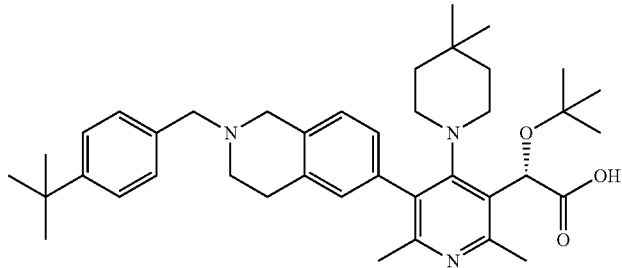<br>Method A: LCMS (M + H) = 626.5 | |
| 28 | (S)-2-(tert-butoxy)-2-(5-(2-(3-chlorobenzyl)-1,2,3,4-tetrahydroisoquinolin-6-yl)-4-(4,4-dimethylpiperidin-1-yl)-2,6-dimethylpyridin-3-yl)acetic acid | |
| | 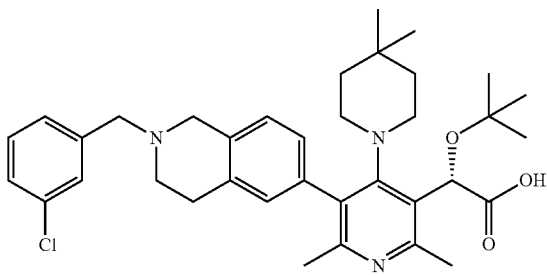 [SMILES: Cc1nc(C)c([C@H](OC(C)(C)C)C(=O)O)c(N2CCC(C)(C)CC2)c1-c1ccc2c(c1)CCN(Cc1cccc(Cl)c1)C2]<br>Method A: LCMS (M + H) = 604.4 | |
| 29 | (S)-2-(tert-butoxy)-2-(5-(2-(2,5-dimethylbenzyl)-1,2,3,4-tetrahydroisoquinolin-6-yl)-4-(4,4-dimethylpiperidin-1-yl)-2,6-dimethylpyridin-3-yl)acetic acid | |
| | 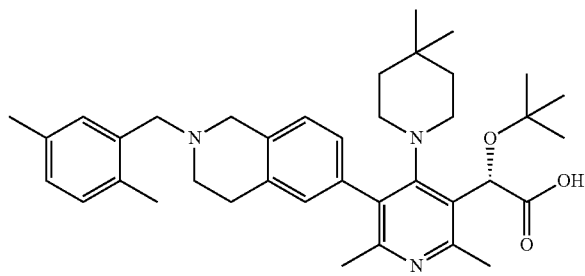 [SMILES: Cc1ccc(C)c(CN2CCc3cc(-c4c(C)nc(C)c([C@H](OC(C)(C)C)C(=O)O)c4N4CCC(C)(C)CC4)ccc3C2)c1]<br>Method A: LCMS (M + H) = 598.4 | |
| 30 | (S)-2-(tert-butoxy)-2-(4-(4,4-dimethylpiperidin-1-yl)-5-(2-(2-fluoro-6-(trifluoromethyl)benzyl)-1,2,3,4-tetrahydroisoquinolin-6-yl)-2,6-dimethylpyridin-3-yl)acetic acid | |
| | 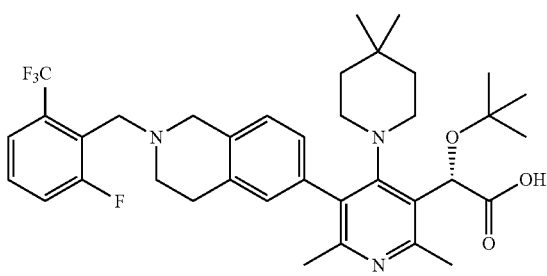 [SMILES: Cc1nc(C)c([C@H](OC(C)(C)C)C(=O)O)c(N2CCC(C)(C)CC2)c1-c1ccc2c(c1)CCN(Cc1c(F)cccc1C(F)(F)F)C2]<br>Method C: LCMS (M + H) = 656.5 | |

| Compound | Name / General Method Used / Structure | LCMS (M + H)+ |
|---|---|---|
| 31 | (S)-2-(tert-butoxy)-2-(5-(2-(3,5-difluorobenzyl)-1,2,3,4-tetrahydroisoquinolin-6-yl)-4-(4,4-dimethylpiperidin-1-yl)-2,6-dimethylpyridin-3-yl)acetic acid<br>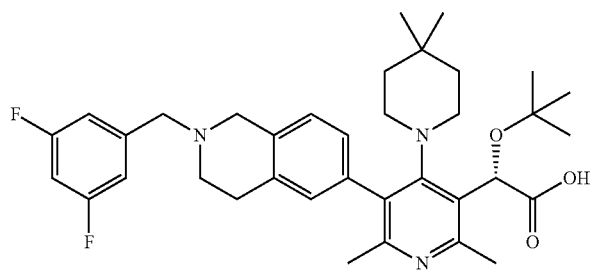 [SMILES: Cc1nc(C)c([C@H](OC(C)(C)C)C(=O)O)c(N2CCC(C)(C)CC2)c1-c1ccc2c(c1)CCN(Cc1cc(F)cc(F)c1)C2]<br>Method C: LCMS (M + H) = 606.3 | |
| 32 | (S)-2-(tert-butoxy)-2-(4-(4,4-dimethylpiperidin-1-yl)-5-(2-(2-fluoro-3-(trifluoromethyl)benzyl)-1,2,3,4-tetrahydroisoquinolin-6-yl)-2,6-dimethylpyridin-3-yl)acetic acid<br>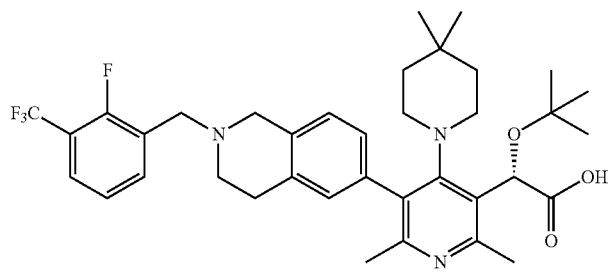 [SMILES: Cc1nc(C)c([C@H](OC(C)(C)C)C(=O)O)c(N2CCC(C)(C)CC2)c1-c1ccc2c(c1)CCN(Cc1cccc(C(F)(F)F)c1F)C2]<br>Method C: LCMS (M + H) = 656.3 | |
| 33 | (S)-2-(tert-butoxy)-2-(5-(2-(2,6-dimethylbenzyl)-1,2,3,4-tetrahydroisoquinolin-6-yl)-4-(4,4-dimethylpiperidin-1-yl)-2,6-dimethylpyridin-3-yl)acetic acid<br>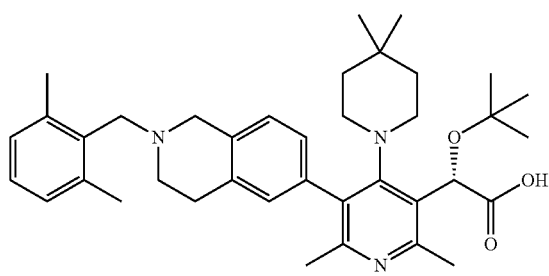 [SMILES: Cc1cccc(C)c1CN1CCc2cc(-c3c(C)nc(C)c([C@H](OC(C)(C)C)C(=O)O)c3N3CCC(C)(C)CC3)ccc2C1]<br>Method C: LCMS (M + H) = 598.4 | |
| 34 | (S)-2-(tert-butoxy)-2-(4-(4,4-dimethylpiperidin-1-yl)-2,6-dimethyl-5-(2-(3,4,5-trifluorobenzyl)-1,2,3,4-tetrahydroisoquinolin-6-yl)pyridin-3-yl)acetic acid | |

| Compound | Name<br>General Method Used<br>Structure | LCMS<br>(M + H)+ |
|---|---|---|
| | 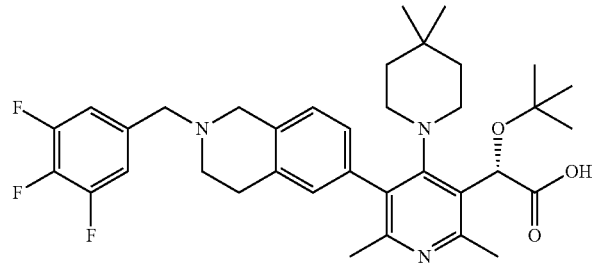 [SMILES: Cc1nc(C)c([C@H](OC(C)(C)C)C(=O)O)c(N2CCC(C)(C)CC2)c1-c1ccc2c(c1)CCN(Cc1cc(F)c(F)c(F)c1)C2]<br>Method A, C: LCMS (M + H) = 624.3 | |
| 35 | (S)-2-(tert-butoxy)-2-(5-(2-(2-chloro-4-fluorobenzyl)-1,2,3,4-tetrahydroisoquinolin-6-yl)-4-(4,4-dimethylpiperidin-1-yl)-2,6-dimethylpyridin-3-yl)acetic acid<br>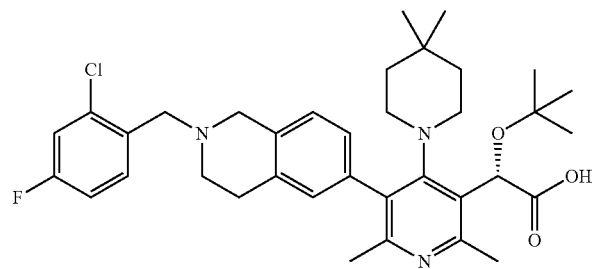 [SMILES: Cc1nc(C)c([C@H](OC(C)(C)C)C(=O)O)c(N2CCC(C)(C)CC2)c1-c1ccc2c(c1)CCN(Cc1ccc(F)cc1Cl)C2]<br>Method C: LCMS (M + H) = 622.0 | |
| 36 | (S)-2-(tert-butoxy)-2-(4-(4,4-dimethylpiperidin-1-yl)-5-(2-(3-isopropylbenzyl)-1,2,3,4-tetrahydroisoquinolin-6-yl)-2,6-dimethylpyridin-3-yl)acetic acid<br>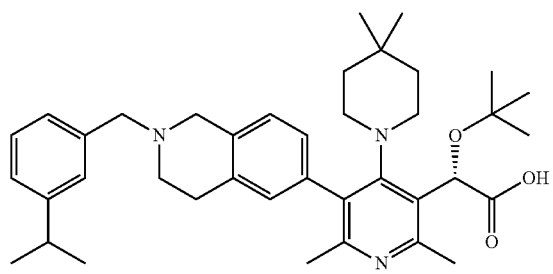 [SMILES: Cc1nc(C)c([C@H](OC(C)(C)C)C(=O)O)c(N2CCC(C)(C)CC2)c1-c1ccc2c(c1)CCN(Cc1cccc(C(C)C)c1)C2]<br>Method C: LCMS (M + H) = 612.5 | |
| 37 | (S)-2-(tert-butoxy)-2-(5-(2-(3,4-difluorobenzyl)-1,2,3,4-tetrahydroisoquinolin-6-yl)-4-(4,4-dimethylpiperidin-1-yl)-2,6-dimethylpyridin-3-yl)acetic acid<br>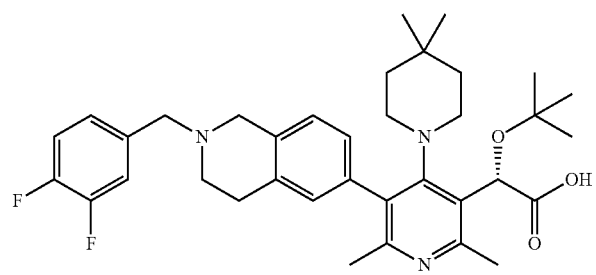 [SMILES: Cc1nc(C)c([C@H](OC(C)(C)C)C(=O)O)c(N2CCC(C)(C)CC2)c1-c1ccc2c(c1)CCN(Cc1ccc(F)c(F)c1)C2]<br>Method A: LCMS (M + H) = 606.5 | |

| Compound | Name<br>General Method Used<br>Structure | LCMS<br>(M + H)+ |
|---|---|---|
| 38 | (S)-2-(tert-butoxy)-2-(5-(2-(2,5-difluorobenzyl)-1,2,3,4-tetrahydroisoquinolin-6-yl)-4-(4,4-dimethylpiperidin-1-yl)-2,6-dimethylpyridin-3-yl)acetic acid<br>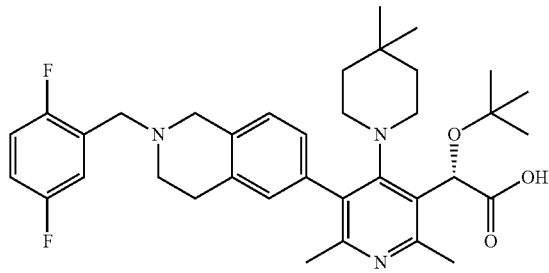 [SMILES: Cc1nc(C)c([C@H](OC(C)(C)C)C(=O)O)c(N2CCC(C)(C)CC2)c1-c1ccc2c(c1)CCN(Cc1cc(F)ccc1F)C2]<br>Method A: LCMS (M + H) = 606.5 | |
| 39 | (S)-2-(tert-butoxy)-2-(5-(2-(4-chloro-2-fluorobenzyl)-1,2,3,4-tetrahydroisoquinolin-6-yl)-4-(4,4-dimethylpiperidin-1-yl)-2,6-dimethylpyridin-3-yl)acetic acid<br>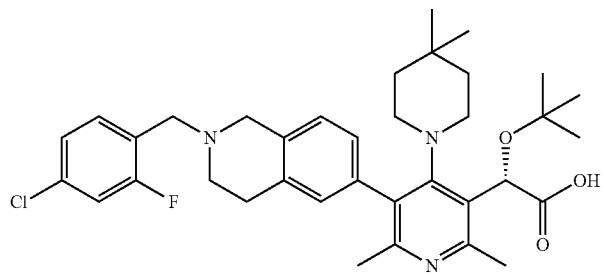 [SMILES: Cc1nc(C)c([C@H](OC(C)(C)C)C(=O)O)c(N2CCC(C)(C)CC2)c1-c1ccc2c(c1)CCN(Cc1ccc(Cl)cc1F)C2]<br>Method A: LCMS (M + H) = 622.4 | |
| 40 | (S)-2-(tert-butoxy)-2-(5-(2-(2,3-dichlorobenzyl)-1,2,3,4-tetrahydroisoquinolin-6-yl)-4-(4,4-dimethylpiperidin-1-yl)-2,6-dimethylpyridin-3-yl)acetic acid<br>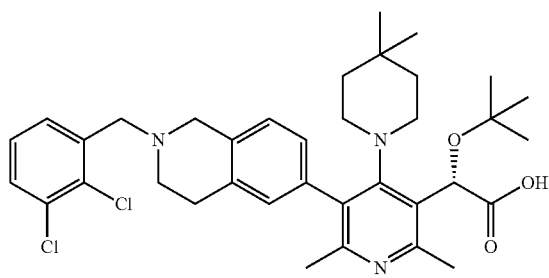 [SMILES: Cc1nc(C)c([C@H](OC(C)(C)C)C(=O)O)c(N2CCC(C)(C)CC2)c1-c1ccc2c(c1)CCN(Cc1cccc(Cl)c1Cl)C2]<br>Method A: LCMS (M + H) = 638.3 | |
| 41 | (S)-2-(tert-butoxy)-2-(4-(4,4-dimethylpiperidin-1-yl)-2,6-dimethyl-5-(2-(2,3,4-trifluorobenzyl)-1,2,3,4-tetrahydroisoquinolin-6-yl)pyridin-3-yl)acetic acid | |

-continued

| Compound | Name<br>General Method Used<br>Structure | LCMS<br>(M + H)+ |
|---|---|---|

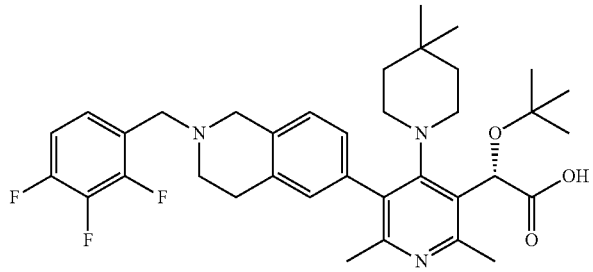 [SMILES: Cc1nc(C)c([C@H](OC(C)(C)C)C(=O)O)c(N2CCC(C)(C)CC2)c1-c1ccc2c(c1)CCN(Cc1ccc(F)c(F)c1F)C2]

Method A, C: LCMS (M + H) = 624.3

42    (S)-2-(tert-butoxy)-2-(5-(2-(5-chloro-2-fluorobenzyl)-1,2,3,4-tetrahydroisoquinolin-6-yl)-4-(4,4-dimethylpiperidin-1-yl)-2,6-dimethylpyridin-3-yl)acetic acid

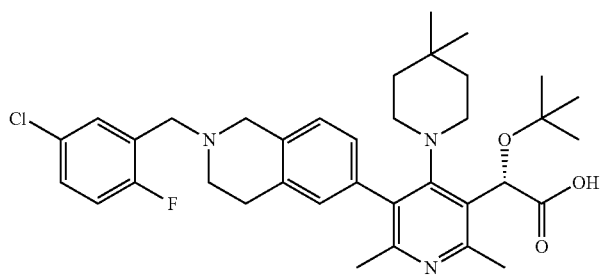 [SMILES: Cc1nc(C)c([C@H](OC(C)(C)C)C(=O)O)c(N2CCC(C)(C)CC2)c1-c1ccc2c(c1)CCN(Cc1cc(Cl)ccc1F)C2]

Method A: LCMS (M + H) = 622.3

43    (S)-2-(tert-butoxy)-2-(5-(2-(3-chloro-5-fluorobenzyl)-1,2,3,4-tetrahydroisoquinolin-6-yl)-4-(4,4-dimethylpiperidin-1-yl)-2,6-dimethylpyridin-3-yl)acetic acid

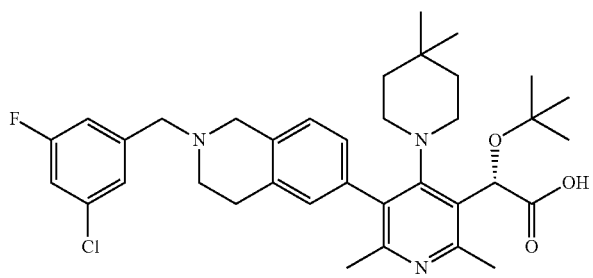 [SMILES: Cc1nc(C)c([C@H](OC(C)(C)C)C(=O)O)c(N2CCC(C)(C)CC2)c1-c1ccc2c(c1)CCN(Cc1cc(F)cc(Cl)c1)C2]

Method A: LCMS (M + H) = 622.4

44    (S)-2-(tert-butoxy)-2-(4-(4,4-dimethylpiperidin-1-yl)-2,6-dimethyl-5-(2-(2,3,6-trifluorobenzyl)-1,2,3,4-tetrahydroisoquinolin-6-yl)pyridin-3-yl)acetic acid

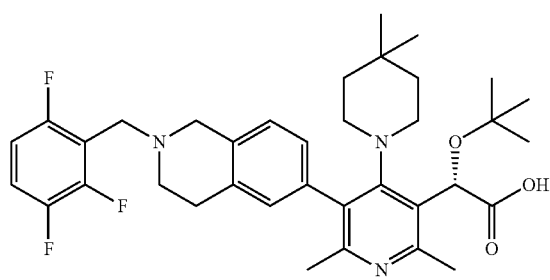 [SMILES: Cc1nc(C)c([C@H](OC(C)(C)C)C(=O)O)c(N2CCC(C)(C)CC2)c1-c1ccc2c(c1)CCN(Cc1c(F)ccc(F)c1F)C2]

Method A: LCMS (M + H) = 624.5

| Compound | Name<br>General Method Used<br>Structure | LCMS<br>(M + H)⁺ |
|---|---|---|
| 45 | (S)-2-(tert-butoxy)-2-(5-(2-(2-chloro-5-fluorobenzyl)-1,2,3,4-tetrahydroisoquinolin-6-yl)-4-(4,4-dimethylpiperidin-1-yl)-2,6-dimethylpyridin-3-yl)acetic acid<br>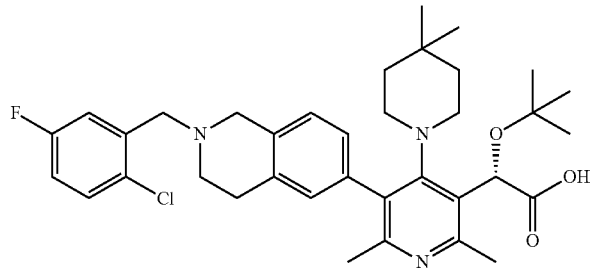<br>Method A: LCMS (M + H) = 622.4 | |
| 46 | (S)-2-(tert-butoxy)-2-(4-(4,4-dimethylpiperidin-1-yl)-5-(2-(3-fluoro-5-methylbenzyl)-1,2,3,4-tetrahydroisoquinolin-6-yl)-2,6-dimethylpyridin-3-yl)acetic acid<br>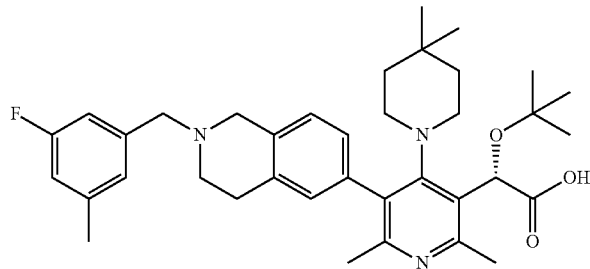 [SMILES: Cc1cc(F)cc(CN2CCc3cc(-c4c(C)nc(C)c([C@H](OC(C)(C)C)C(=O)O)c4N4CCC(C)(C)CC4)ccc3C2)c1]<br>Method A: LCMS (M + H) = 602.5 | |
| 47 | (S)-2-(tert-butoxy)-2-(4-(4,4-dimethylpiperidin-1-yl)-5-(2-(5-fluoro-2-methylbenzyl)-1,2,3,4-tetrahydroisoquinolin-6-yl)-2,6-dimethylpyridin-3-yl)acetic acid<br>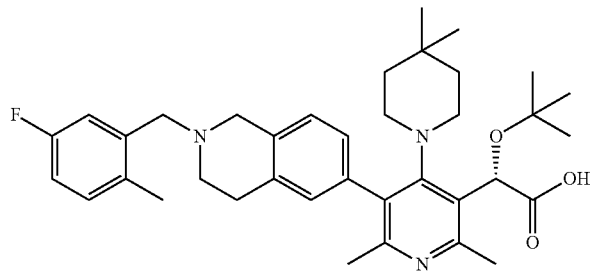 [SMILES: Cc1ccc(F)cc1CN1CCc2cc(-c3c(C)nc(C)c([C@H](OC(C)(C)C)C(=O)O)c3N3CCC(C)(C)CC3)ccc2C1]<br>Method A: LCMS (M + H) = 602.5 | |
| 48 | (S)-2-(tert-butoxy)-2-(5-(2-(2,6-difluoro-3-methylbenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|

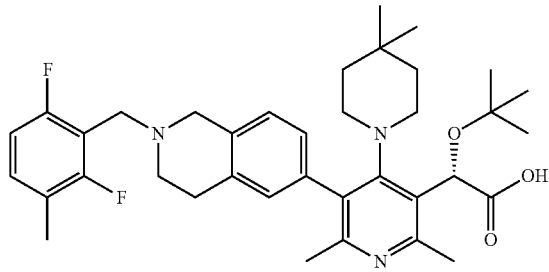

Method A: LCMS (M + H) = 620.5

49     (S)-2-(tert-butoxy)-2-(4-(4,4-dimethylpiperidin-1-yl)-2,6-dimethyl-5-(2-(2,4,5-trifluorobenzyl)-1,2,3,4-tetrahydroisoquinolin-6-yl)pyridin-3-yl)acetic acid

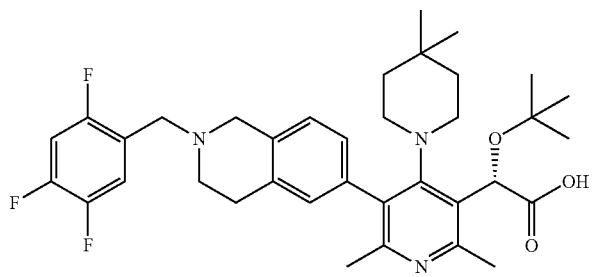 [SMILES: Cc1nc(C)c([C@H](OC(C)(C)C)C(=O)O)c(N2CCC(C)(C)CC2)c1-c1ccc2c(c1)CCN(Cc1cc(F)c(F)cc1F)C2]

Method A: LCMS (M + H) = 624.4

50     (S)-2-(tert-butoxy)-2-(5-(2-(2,6-difluorobenzyl)-1,2,3,4-tetrahydroisoquinolin-6-yl)-4-(4,4-dimethylpiperidin-1-yl)-2,6-dimethylpyridin-3-yl)acetic acid

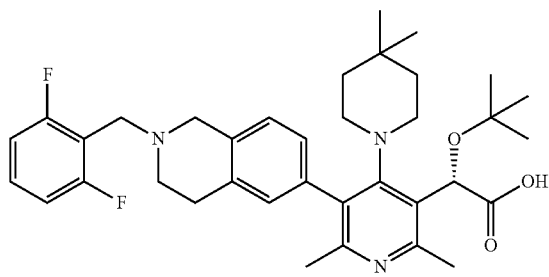 [SMILES: Cc1nc(C)c([C@H](OC(C)(C)C)C(=O)O)c(N2CCC(C)(C)CC2)c1-c1ccc2c(c1)CCN(Cc1c(F)cccc1F)C2]

Method A: LCMS (M + H) = 606.5

51     (S)-2-(tert-butoxy)-2-(4-(4,4-dimethylpiperidin-1-yl)-5-(2-(2-fluoro-6-methylbenzyl)-1,2,3,4-tetrahydroisoquinolin-6-yl)-2,6-dimethylpyridin-3-yl)acetic acid

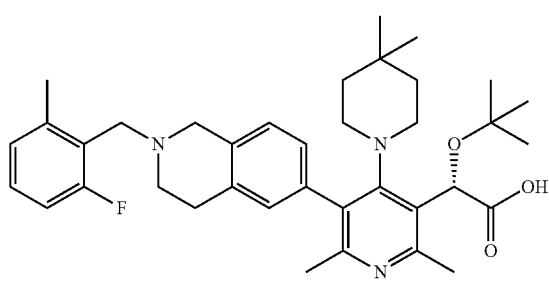 [SMILES: Cc1cccc(F)c1CN1CCc2cc(-c3c(C)nc(C)c([C@H](OC(C)(C)C)C(=O)O)c3N3CCC(C)(C)CC3)ccc2C1]

| Compound | Name<br>General Method Used<br>Structure | LCMS<br>(M + H)⁺ |
|---|---|---|
|  | Method A, D: ¹H NMR (400 MHz, DMSO-d₆) δ 7.28-7.19 (m, 1H), 7.15-6.98 (m, 4H), 6.87 (s, 1H), 5.96 (br. s., 1H), 4.94 (td, J = 6.2, 3.4 Hz, 1H), 3.68 (br. s., 2H), 3.64 (br. s., 2H), 2.88-2.67 (m, 6H), 2.44-2.39 (m, 6H), 2.10 (s, 2H), 2.05 (s, 1H), 1.82 (t, J = 11.4 Hz, 1H), 1.51-1.41 (m, 1H), 1.25 (d, J = 13.2 Hz, 1H), 1.17 (dd, J = 6.2, 1.3 Hz, 4H), 1.15-1.09 (m, 14H), 0.84 (s, 3H), 0.59 (s, 3H). LCMS (M + H) = 644.3. LCMS (M + H) = 602.5 | |
| 52 | (S)-2-(tert-butoxy)-2-(4-(4,4-dimethylpiperidin-1-yl)-2,6-dimethyl-5-(2-(2-methyl-5-(trifluoromethyl)benzyl)-1,2,3,4-tetrahydroisoquinolin-6-yl)pyridin-3-yl)acetic acid | |

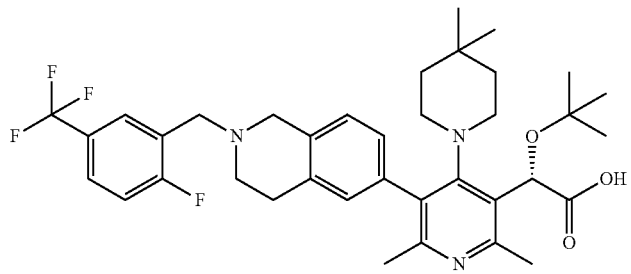 [SMILES: Cc1nc(C)c([C@H](OC(C)(C)C)C(=O)O)c(N2CCC(C)(C)CC2)c1-c1ccc2c(c1)CCN(Cc1cc(C(F)(F)F)ccc1F)C2]

Method A: LCMS (M + H) = 652.5

| 53 | (S)-2-(tert-butoxy)-2-(5-(2-(2,4-dichlorobenzyl)-1,2,3,4-tetrahydroisoquinolin-6-yl)-4-(4,4-dimethylpiperidin-1-yl)-2,6-dimethylpyridin-3-yl)acetic acid | |
|---|---|---|

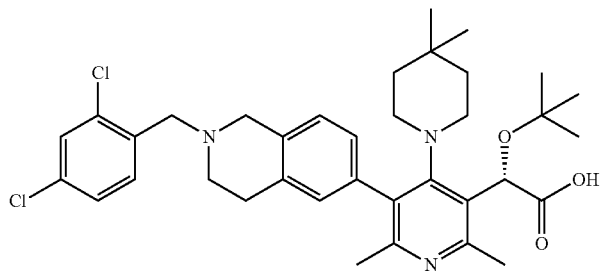 [SMILES: Cc1nc(C)c([C@H](OC(C)(C)C)C(=O)O)c(N2CCC(C)(C)CC2)c1-c1ccc2c(c1)CCN(Cc1ccc(Cl)cc1Cl)C2]

Method A: LCMS (M + H) = 638.4

| 54 | (S)-2-(tert-butoxy)-2-(4-(4,4-dimethylpiperidin-1-yl)-5-(2-(2-fluoro-3-methylbenzyl)-1,2,3,4-tetrahydroisoquinolin-6-yl)-2,6-dimethylpyridin-3-yl)acetic acid | |
|---|---|---|

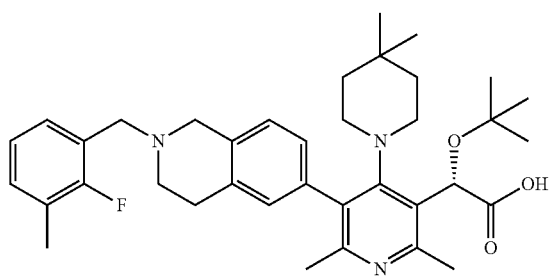 [SMILES: Cc1cccc(CN2CCc3cc(-c4c(C)nc(C)c([C@H](OC(C)(C)C)C(=O)O)c4N4CCC(C)(C)CC4)ccc3C2)c1F]

Method A: LCMS (M + H) = 602.5

| 55 | (S)-2-(tert-butoxy)-2-(5-(2-(2-chlorobenzyl)-1,2,3,4-tetrahydroisoquinolin-6-yl)-4-(4,4-dimethylpiperidin-1-yl)-2,6-dimethylpyridin-3-yl)acetic acid | |
|---|---|---|

-continued

| Compound | Name<br>General Method Used<br>Structure | LCMS<br>(M + H)+ |
|---|---|---|
|  | 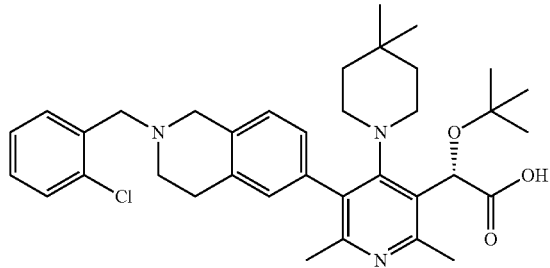<br>Method A: LCMS (M + H) = 604.5 |  |
| 56 | (S)-2-(tert-butoxy)-2-(5-(2-(4-chlorobenzyl)-1,2,3,4-tetrahydroisoquinolin-6-yl)-4-(4,4-dimethylpiperidin-1-yl)-2,6-dimethylpyridin-3-yl)acetic acid |  |
|  | 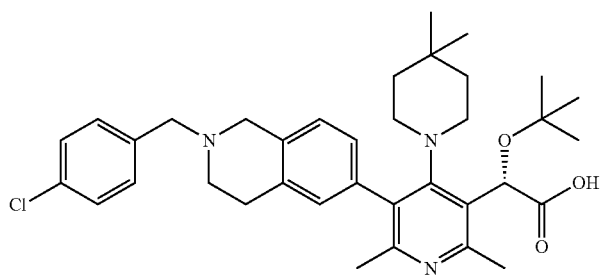 [SMILES: Cc1nc(C)c([C@H](OC(C)(C)C)C(=O)O)c(N2CCC(C)(C)CC2)c1-c1ccc2c(c1)CCN(Cc1ccc(Cl)cc1)C2]<br>Method A: LCMS (M + H) = 604.4 |  |
| 57 | (S)-2-(tert-butoxy)-2-(4-(4,4-dimethylpiperidin-1-yl)-2,6-dimethyl-5-(2-(2,4,6-trimethylbenzyl)-1,2,3,4-tetrahydroisoquinolin-6-yl)pyridin-3-yl)acetic acid |  |
|  | 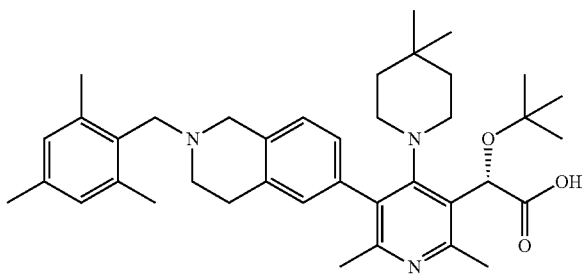 [SMILES: Cc1cc(C)c(CN2CCc3cc(-c4c(C)nc(C)c([C@H](OC(C)(C)C)C(=O)O)c4N4CCC(C)(C)CC4)ccc3C2)c(C)c1]<br>Method A: LCMS (M + H) = 612.5 |  |
| 58 | (S)-2-(tert-butoxy)-2-(4-(4,4-dimethylpiperidin-1-yl)-2,6-dimethyl-5-(2-(2,4,6-trifluorobenzyl)-1,2,3,4-tetrahydroisoquinolin-6-yl)pyridin-3-yl)acetic acid |  |
|  | 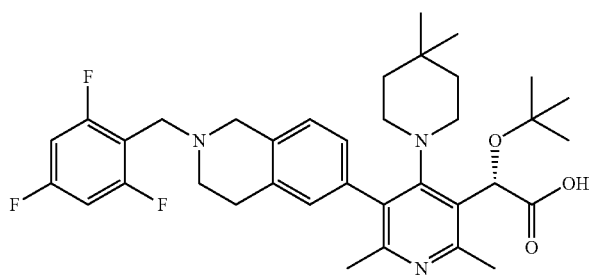 [SMILES: Cc1nc(C)c([C@H](OC(C)(C)C)C(=O)O)c(N2CCC(C)(C)CC2)c1-c1ccc2c(c1)CCN(Cc1c(F)cc(F)cc1F)C2]<br>Method A: LCMS (M + H) = 624.5 |  |

| Compound | Name<br>General Method Used<br>Structure | LCMS<br>(M + H)+ |
|---|---|---|
| 59 | (S)-2-(tert-butoxy)-2-(4-(4,4-dimethylpiperidin-1-yl)-5-(2-(4-isopropylbenzyl)-1,2,3,4-tetrahydroisoquinolin-6-yl)-2,6-dimethylpyridin-3-yl)acetic acid<br>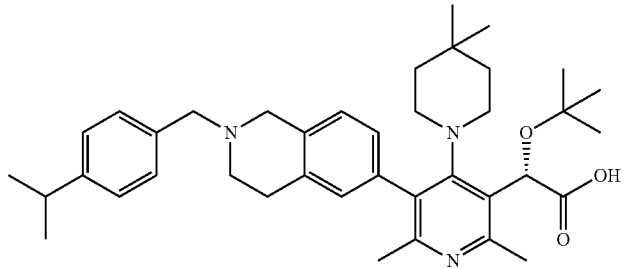 [SMILES: Cc1nc(C)c([C@H](OC(C)(C)C)C(=O)O)c(N2CCC(C)(C)CC2)c1-c1ccc2c(c1)CCN(Cc1ccc(C(C)C)cc1)C2]<br>Method A: LCMS (M + H) = 612.6 | |
| 60 | (S)-2-(tert-butoxy)-2-(4-(4,4-dimethylpiperidin-1-yl)-5-(2-(4-ethylbenzyl)-1,2,3,4-tetrahydroisoquinolin-6-yl)-2,6-dimethylpyridin-3-yl)acetic acid<br>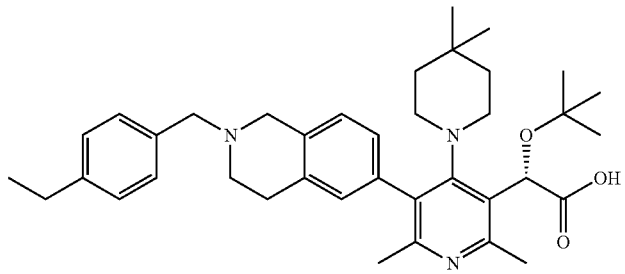 [SMILES: CCc1ccc(CN2CCc3cc(-c4c(C)nc(C)c([C@H](OC(C)(C)C)C(=O)O)c4N4CCC(C)(C)CC4)ccc3C2)cc1]<br>Method A: LCMS (M + H) = 598.2 | |
| 61 | (S)-2-(tert-butoxy)-2-(5-(2-(3-cyanobenzyl)-1,2,3,4-tetrahydroisoquinolin-6-yl)-4-(4,4-dimethylpiperidin-1-yl)-2,6-dimethylpyridin-3-yl)acetic acid<br>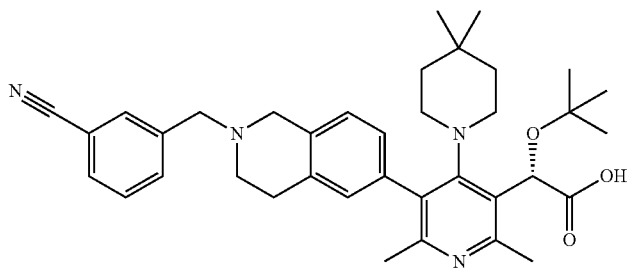 [SMILES: Cc1nc(C)c([C@H](OC(C)(C)C)C(=O)O)c(N2CCC(C)(C)CC2)c1-c1ccc2c(c1)CCN(Cc1cccc(C#N)c1)C2]<br>Method C: LCMS (M + H) = 595.3 | |
| 62 | (S)-2-(tert-butoxy)-2-(5-(2-(2-cyanobenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|
| | 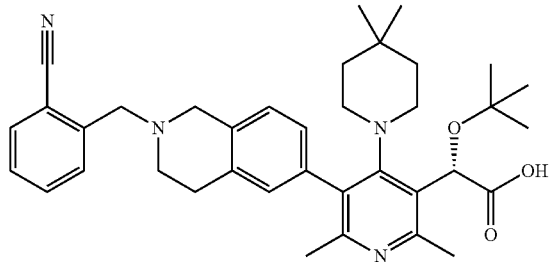 [SMILES: Cc1nc(C)c([C@H](OC(C)(C)C)C(=O)O)c(N2CCC(C)(C)CC2)c1-c1ccc2c(c1)CCN(Cc1ccccc1C#N)C2]→ Method C: LCMS (M + H) = 595.3 | |
| 63 | (S)-2-(tert-butoxy)-2-(5-(2-(5-cyano-2-fluorobenzyl)-1,2,3,4-tetrahydroisoquinolin-6-yl)-4-(4,4-dimethylpiperidin-1-yl)-2,6-dimethylpyridin-3-yl)acetic acid | |
| | 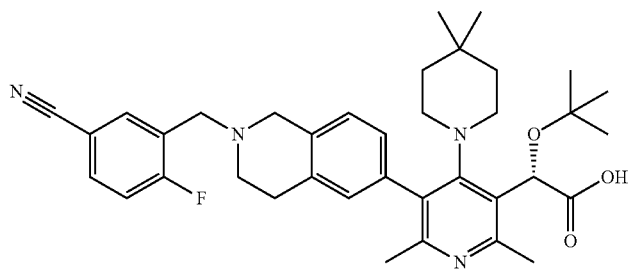 [SMILES: Cc1nc(C)c([C@H](OC(C)(C)C)C(=O)O)c(N2CCC(C)(C)CC2)c1-c1ccc2c(c1)CCN(Cc1cc(C#N)ccc1F)C2]→ Method C: LCMS (M + H) = 613.3 | |
| 64 | (S)-2-(tert-butoxy)-2-(5-(2-(4-cyanobenzyl)-1,2,3,4-tetrahydroisoquinolin-6-yl)-4-(4,4-dimethylpiperidin-1-yl)-2,6-dimethylpyridin-3-yl)acetic acid | |
| | 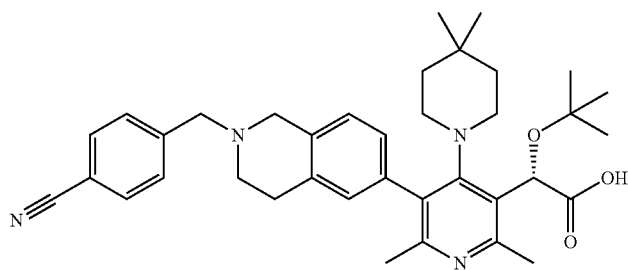→ Method C: LCMS (M + H) = 595.3 | |
| 65 | (S)-2-(tert-butoxy)-2-(5-(2-(4-cyano-2-methylbenzyl)-1,2,3,4-tetrahydroisoquinolin-6-yl)-4-(4,4-dimethylpiperidin-1-yl)-2,6-dimethylpyridin-3-yl)acetic acid | |
| | 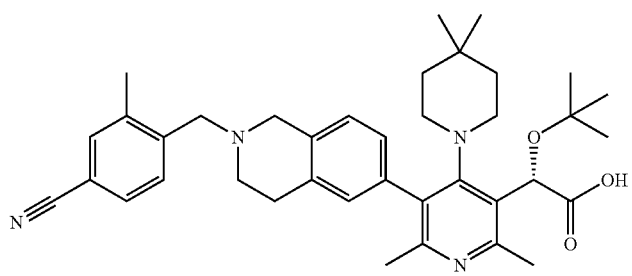→ Method C: LCMS (M + H) = 609.3 | |

| Compound | Name<br>General Method Used<br>Structure | LCMS<br>(M + H)+ |
|---|---|---|
| 66 | (S)-2-(tert-butoxy)-2-(4-(4,4-dimethylpiperidin-1-yl)-5-(2-(5-fluoro-2-(trifluoromethyl)benzyl)-1,2,3,4-tetrahydroisoquinolin-6-yl)-2,6-dimethylpyridin-3-yl)acetic acid<br>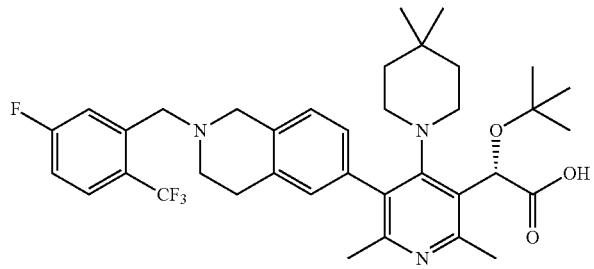 [SMILES: Cc1nc(C)c([C@H](OC(C)(C)C)C(=O)O)c(N2CCC(C)(C)CC2)c1-c1ccc2c(c1)CCN(Cc1cc(F)ccc1C(F)(F)F)C2]<br>Method C: LCMS (M + H) = 656.3 | |
| 67 | (S)-2-(tert-butoxy)-2-(4-(4,4-dimethylpiperidin-1-yl)-5-(2-(4-fluoro-3-(trifluoromethyl)benzyl)-1,2,3,4-tetrahydroisoquinolin-6-yl)-2,6-dimethylpyridin-3-yl)acetic acid<br>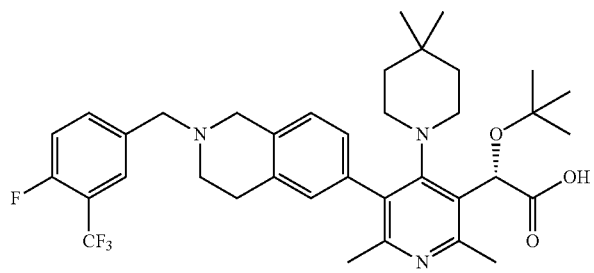 [SMILES: Cc1nc(C)c([C@H](OC(C)(C)C)C(=O)O)c(N2CCC(C)(C)CC2)c1-c1ccc2c(c1)CCN(Cc1ccc(F)c(C(F)(F)F)c1)C2]<br>Method C: LCMS (M + H) = 656.3 | |
| 68 | (S)-2-(tert-butoxy)-2-(4-(4,4-dimethylpiperidin-1-yl)-5-(2-(3-fluoro-5-(trifluoromethyl)benzyl)-1,2,3,4-tetrahydroisoquinolin-6-yl)-2,6-dimethylpyridin-3-yl)acetic acid<br>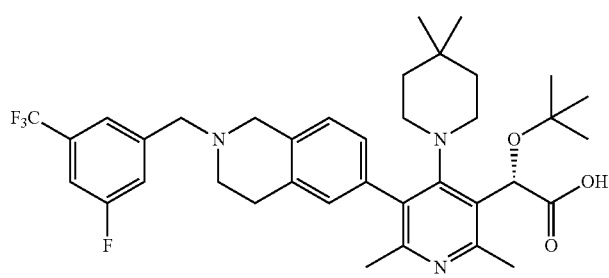 [SMILES: Cc1nc(C)c([C@H](OC(C)(C)C)C(=O)O)c(N2CCC(C)(C)CC2)c1-c1ccc2c(c1)CCN(Cc1cc(F)cc(C(F)(F)F)c1)C2]<br>Method C: LCMS (M + H) = 656.3 | |
| 69 | (S)-2-(tert-butoxy)-2-(4-(4,4-dimethylpiperidin-1-yl)-5-(2-(4-fluoro-2-(trifluoromethyl)benzyl)-1,2,3,4-tetrahydroisoquinolin-6-yl)-2,6-dimethylpyridin-3-yl)acetic acid | |

| Compound | Name<br>General Method Used<br>Structure | LCMS<br>(M + H)+ |
|---|---|---|
| | 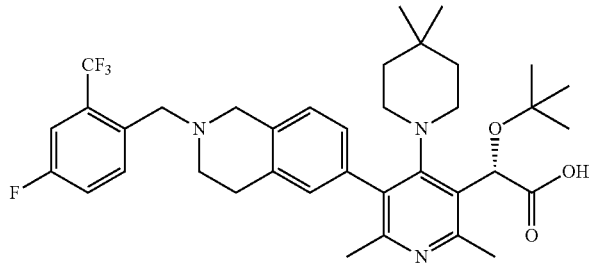<br>Method C: LCMS (M + H) = 656.3 | |
| 70 | (S)-2-(tert-butoxy)-2-(4-(4,4-dimethylpiperidin-1-yl)-5-(2-(2-fluoro-5-(trifluoromethyl)benzyl)-1,2,3,4-tetrahydroisoquinolin-6-yl)-2,6-dimethylpyridin-3-yl)acetic acid | |
| | 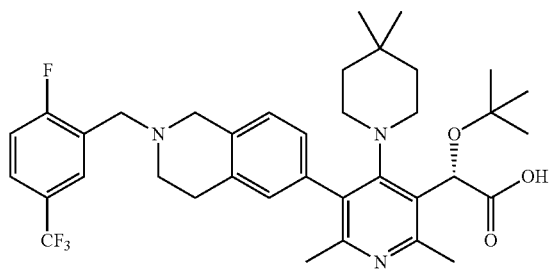 [SMILES: Cc1nc(C)c([C@H](OC(C)(C)C)C(=O)O)c(N2CCC(C)(C)CC2)c1-c1ccc2c(c1)CCN(Cc1cc(C(F)(F)F)ccc1F)C2]<br>Method C: LCMS (M + H) = 656.3 | |
| 71 | (S)-2-(tert-butoxy)-2-(4-(4,4-dimethylpiperidin-1-yl)-5-(2-(4-fluoro-3-methylbenzyl)-1,2,3,4-tetrahydroisoquinolin-6-yl)-2,6-dimethylpyridin-3-yl)acetic acid | |
| | 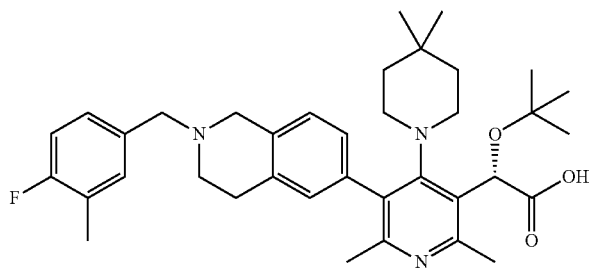 [SMILES: Cc1cc(CN2CCc3cc(-c4c(C)nc(C)c([C@H](OC(C)(C)C)C(=O)O)c4N4CCC(C)(C)CC4)ccc3C2)ccc1F]<br>Method C: LCMS (M + H) = 602.3 | |
| 72 | (S)-2-(tert-butoxy)-2-(4-(4,4-dimethylpiperidin-1-yl)-5-(2-(4-fluoro-2,3-dimethylbenzyl)-1,2,3,4-tetrahydroisoquinolin-6-yl)-2,6-dimethylpyridin-3-yl)acetic acid | |
| | 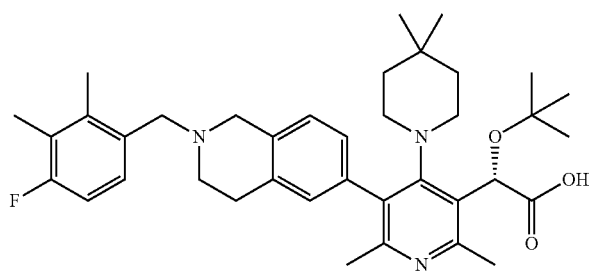 [SMILES: Cc1nc(C)c([C@H](OC(C)(C)C)C(=O)O)c(N2CCC(C)(C)CC2)c1-c1ccc2c(c1)CCN(Cc1ccc(F)c(C)c1C)C2]<br>Method C: LCMS (M + H) = 616.2 | |

| Compound | Name<br>General Method Used<br>Structure | LCMS<br>(M + H)+ |
|---|---|---|
| 73 | (S)-2-(tert-butoxy)-2-(5-(2-(2,3-difluoro-4-methylbenzyl)-1,2,3,4-tetrahydroisoquinolin-6-yl)-4-(4,4-dimethylpiperidin-1-yl)-2,6-dimethylpyridin-3-yl)acetic acid<br>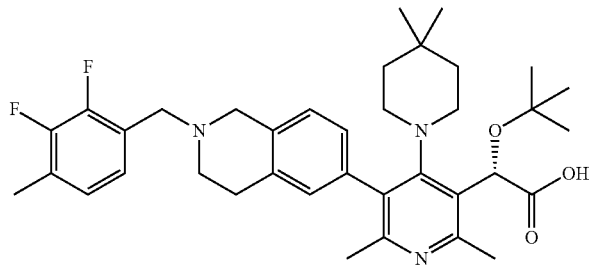 [SMILES: Cc1ccc(CN2CCc3cc(-c4c(C)nc(C)c([C@H](OC(C)(C)C)C(=O)O)c4N4CCC(C)(C)CC4)ccc3C2)c(F)c1F]<br>Method C: LCMS (M + H) = 620.1 | |
| 74 | (S)-2-(tert-butoxy)-2-(4-(4,4-dimethylpiperidin-1-yl)-5-(2-(2-fluoro-5-methylbenzyl)-1,2,3,4-tetrahydroisoquinolin-6-yl)-2,6-dimethylpyridin-3-yl)acetic acid<br>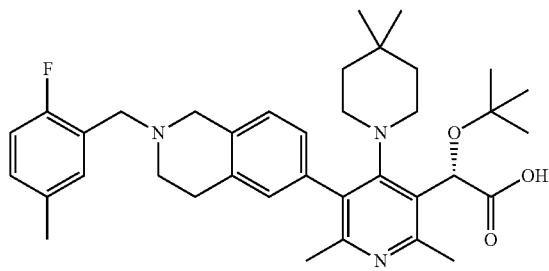 [SMILES: Cc1ccc(F)c(CN2CCc3cc(-c4c(C)nc(C)c([C@H](OC(C)(C)C)C(=O)O)c4N4CCC(C)(C)CC4)ccc3C2)c1]<br>Method C: LCMS (M + H) = 602.3 | |
| 75 | (S)-2-(tert-butoxy)-2-(4-(4,4-dimethylpiperidin-1-yl)-5-(2-(4-fluoro-3,5-dimethylbenzyl)-1,2,3,4-tetrahydroisoquinolin-6-yl)-2,6-dimethylpyridin-3-yl)acetic acid<br>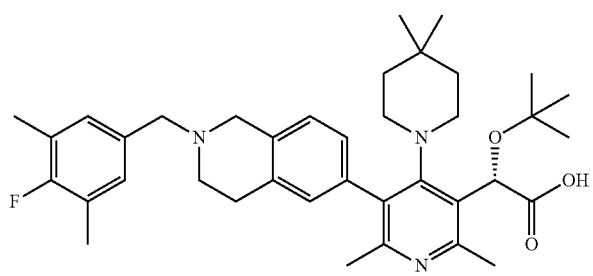 [SMILES: Cc1cc(CN2CCc3cc(-c4c(C)nc(C)c([C@H](OC(C)(C)C)C(=O)O)c4N4CCC(C)(C)CC4)ccc3C2)cc(C)c1F]<br>Method C: LCMS (M + H) = 616.3 | |
| 76 | (S)-2-(tert-butoxy)-2-(5-(2-(3,4-difluoro-5-methylbenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|

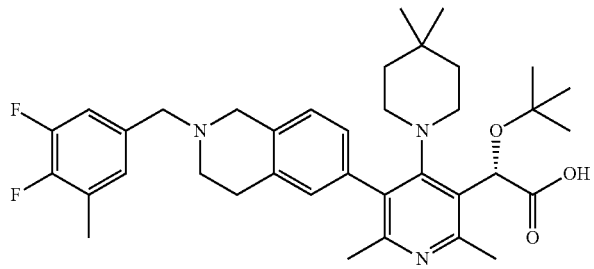 [SMILES: Cc1cc(CN2CCc3cc(-c4c(C)nc(C)c([C@H](OC(C)(C)C)C(=O)O)c4N4CCC(C)(C)CC4)ccc3C2)cc(F)c1F]

Method C: LCMS (M + H) = 620.3

77  (S)-2-(tert-butoxy)-2-(4-(4,4-dimethylpiperidin-1-yl)-5-(2-(2-isopropylbenzyl)-1,2,3,4-tetrahydroisoquinolin-6-yl)-2,6-dimethylpyridin-3-yl)acetic acid

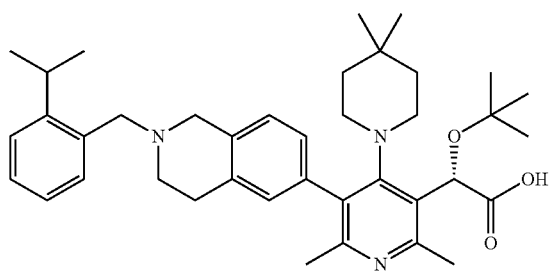 [SMILES: Cc1nc(C)c([C@H](OC(C)(C)C)C(=O)O)c(N2CCC(C)(C)CC2)c1-c1ccc2c(c1)CCN(Cc1ccccc1C(C)C)C2]

Method C: LCMS (M + H) = 612.4

78  (S)-2-(tert-butoxy)-2-(4-(4,4-dimethylpiperidin-1-yl)-2,6-dimethyl-5-(2-(2,4,5-trimethylbenzyl)-1,2,3,4-tetrahydroisoquinolin-6-yl)pyridin-3-yl)acetic acid

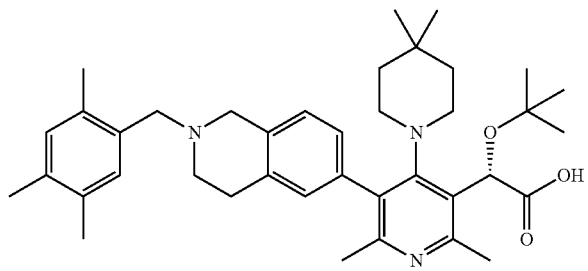 [SMILES: Cc1cc(C)c(CN2CCc3cc(-c4c(C)nc(C)c([C@H](OC(C)(C)C)C(=O)O)c4N4CCC(C)(C)CC4)ccc3C2)cc1C]

Method C: LCMS (M + H) = 612.2

79  (S)-2-(tert-butoxy)-2-(5-(2-(3,5-dimethylbenzyl)-1,2,3,4-tetrahydroisoquinolin-6-yl)-4-(4,4-dimethylpiperidin-1-yl)-2,6-dimethylpyridin-3-yl)acetic acid

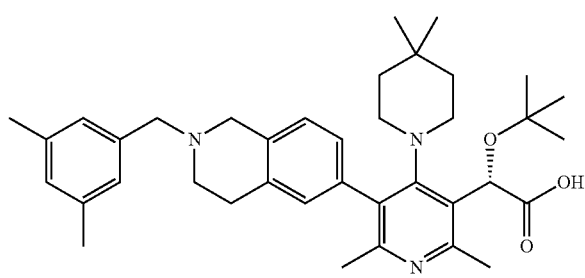 [SMILES: Cc1cc(C)cc(CN2CCc3cc(-c4c(C)nc(C)c([C@H](OC(C)(C)C)C(=O)O)c4N4CCC(C)(C)CC4)ccc3C2)c1]

Method C: LCMS (M + H) = 598.3

-continued

| Compound | Name<br>General Method Used<br>Structure | LCMS<br>(M + H)+ |
|---|---|---|
| 80 | (S)-2-(tert-butoxy)-2-(5-(2-(2,3-dimethylbenzyl)-1,2,3,4-tetrahydroisoquinolin-6-yl)-4-(4,4-dimethylpiperidin-1-yl)-2,6-dimethylpyridin-3-yl)acetic acid 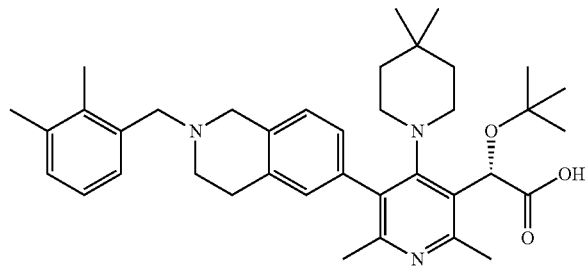 [SMILES: Cc1cccc(CN2CCc3cc(-c4c(C)nc(C)c([C@H](OC(C)(C)C)C(=O)O)c4N4CCC(C)(C)CC4)ccc3C2)c1C] Method C: LCMS (M + H) = 598.3 | |
| 81 | (S)-2-(tert-butoxy)-2-(5-(2-(3-(tert-butyl)benzyl)-1,2,3,4-tetrahydroisoquinolin-6-yl)-4-(4,4-dimethylpiperidin-1-yl)-2,6-dimethylpyridin-3-yl)acetic acid 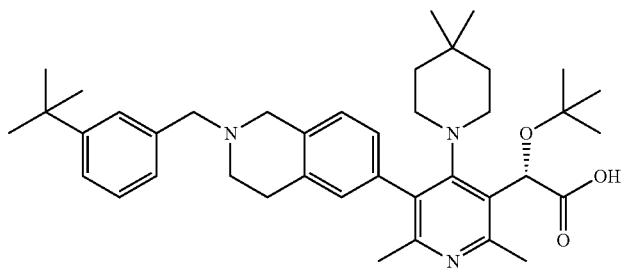 [SMILES: Cc1nc(C)c([C@H](OC(C)(C)C)C(=O)O)c(N2CCC(C)(C)CC2)c1-c1ccc2c(c1)CCN(Cc1cccc(C(C)(C)C)c1)C2] Method C: LCMS (M + H) = 626.4 | |
| 82 | (S)-2-(tert-butoxy)-2-(4-(4,4-dimethylpiperidin-1-yl)-5-(2-(3-fluoro-2-methylbenzyl)-1,2,3,4-tetrahydroisoquinolin-6-yl)-2,6-dimethylpyridin-3-yl)acetic acid 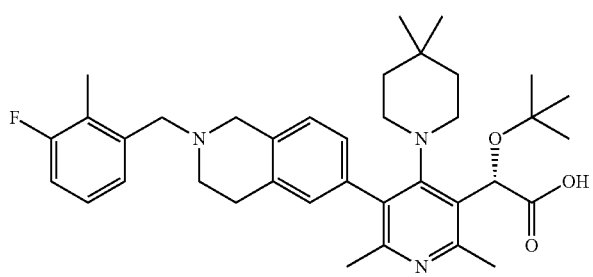 Method C: LCMS (M + H) = 602.3 | |
| 83 | (S)-2-(tert-butoxy)-2-(5-(2-(2,5-difluoro-4-methoxybenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|
| | 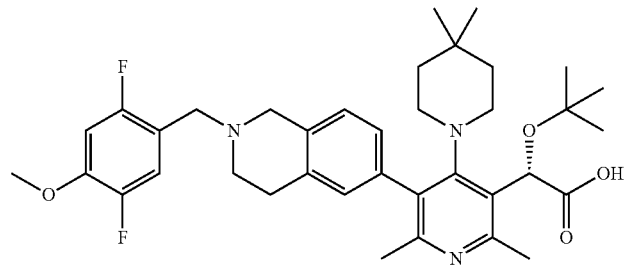<br>Method C: LCMS (M + H) = 636.2 | |
| 84 | (S)-2-(tert-butoxy)-2-(5-(2-(2,6-difluoro-4-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| | 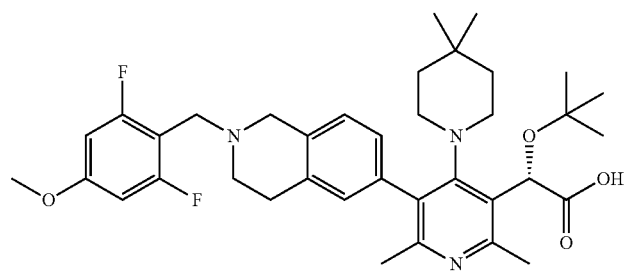 [SMILES: COc1cc(F)c(CN2CCc3cc(-c4c(C)nc(C)c([C@H](OC(C)(C)C)C(=O)O)c4N4CCC(C)(C)CC4)ccc3C2)c(F)c1]<br>Method C: LCMS (M + H) = 636.2 | |
| 85 | (S)-2-(5-(2-(2-(benzyloxy)-3,5-dichlorobenzyl)-1,2,3,4-<br>tetrahydroisoquinolin-6-yl)-4-(4,4-dimethylpiperidin-1-yl)-2,6-<br>dimethylpyridin-3-yl)-2-(tert-butoxy)acetic acid | |
| | 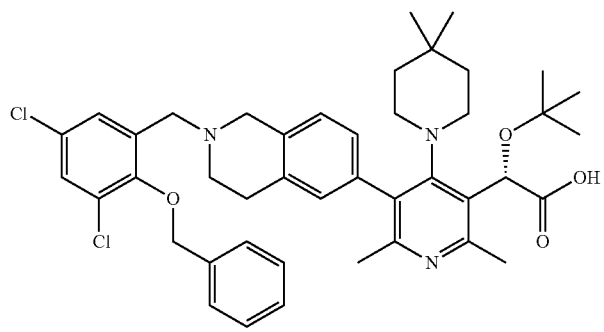 [SMILES: Cc1nc(C)c([C@H](OC(C)(C)C)C(=O)O)c(N2CCC(C)(C)CC2)c1-c1ccc2c(c1)CCN(Cc1cc(Cl)cc(Cl)c1OCc1ccccc1)C2]<br>Method C: LCMS (M + H) = 744.4 | |
| 86 | (S)-2-(tert-butoxy)-2-(5-(2-(4,5-difluoro-2-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| | 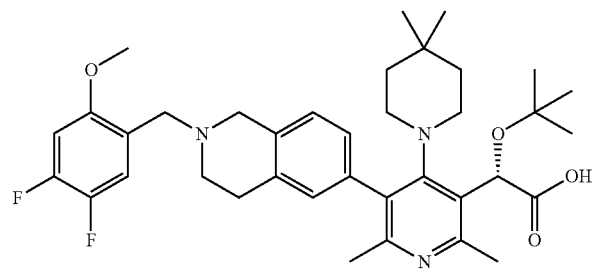 [SMILES: COc1cc(F)c(F)cc1CN1CCc2cc(-c3c(C)nc(C)c([C@H](OC(C)(C)C)C(=O)O)c3N3CCC(C)(C)CC3)ccc2C1]<br>Method C: LCMS (M + H) = 636.2 | |

| Compound | Name<br>General Method Used<br>Structure | LCMS<br>(M + H)+ |
|---|---|---|
| 87 | (S)-2-(tert-butoxy)-2-(5-(2-(2,3-difluoro-6-methoxybenzyl)-1,2,3,4-tetrahydroisoquinolin-6-yl)-4-(4,4-dimethylpiperidin-1-yl)-2,6-dimethylpyridin-3-yl)acetic acid<br>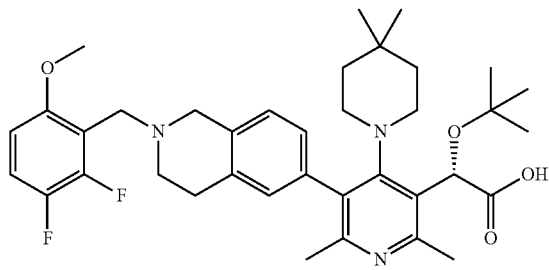 [SMILES: COc1ccc(F)c(F)c1CN1CCc2cc(-c3c(C)nc(C)c([C@H](OC(C)(C)C)C(=O)O)c3N3CCC(C)(C)CC3)ccc2C1]<br>Method A, C: LCMS (M + H) = 636.2 | |
| 88 | (S)-2-(tert-butoxy)-2-(4-(4,4-dimethylpiperidin-1-yl)-5-(2-(2-(2-hydroxyethoxy)benzyl)-1,2,3,4-tetrahydroisoquinolin-6-yl)-2,6-dimethylpyridin-3-yl)acetic acid<br>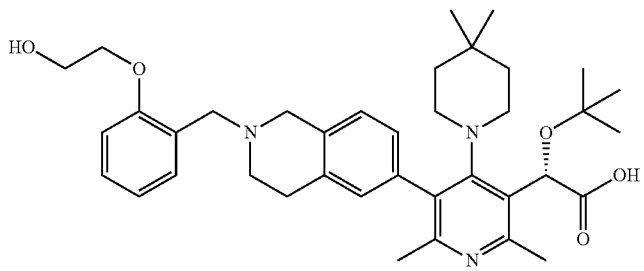 [SMILES: Cc1nc(C)c([C@H](OC(C)(C)C)C(=O)O)c(N2CCC(C)(C)CC2)c1-c1ccc2c(c1)CCN(Cc1ccccc1OCCO)C2]<br>Method C: LCMS (M + H) = 630.2 | |
| 89 | (S)-2-(tert-butoxy)-2-(5-(2-(2,4-difluoro-6-methoxybenzyl)-1,2,3,4-tetrahydroisoquinolin-6-yl)-4-(4,4-dimethylpiperidin-1-yl)-2,6-dimethylpyridin-3-yl)acetic acid<br>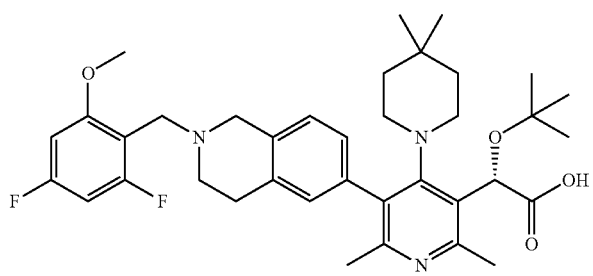 [SMILES: COc1cc(F)cc(F)c1CN1CCc2cc(-c3c(C)nc(C)c([C@H](OC(C)(C)C)C(=O)O)c3N3CCC(C)(C)CC3)ccc2C1]<br>Method C: LCMS (M + H) = 636.2 | |
| 90 | (S)-2-(tert-butoxy)-2-(5-(2-(2,4-dichloro-6-ethoxybenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|
| 91 | Method C: LCMS (M + H) = 682.1<br><br>(S)-2-(tert-butoxy)-2-(5-(2-(2,3-dichloro-4-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| 92 | Method C: LCMS (M + H) = 668.1<br><br>(S)-2-(tert-butoxy)-2-(5-(2-(2,6-difluoro-3-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| 93 | Method C: LCMS (M + H) = 636.3<br><br>(S)-2-(tert-butoxy)-2-(5-(2-(4-chloro-2-fluoro-5-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| | Method C: LCMS (M + H) = 652.3 | |

| Compound | Name<br>General Method Used<br>Structure | LCMS<br>(M + H)+ |
|---|---|---|
| 94 | (S)-2-(tert-butoxy)-2-(5-(2-(2,4-difluoro-5-methoxybenzyl)-1,2,3,4-tetrahydroisoquinolin-6-yl)-4-(4,4-dimethylpiperidin-1-yl)-2,6-dimethylpyridin-3-yl)acetic acid<br>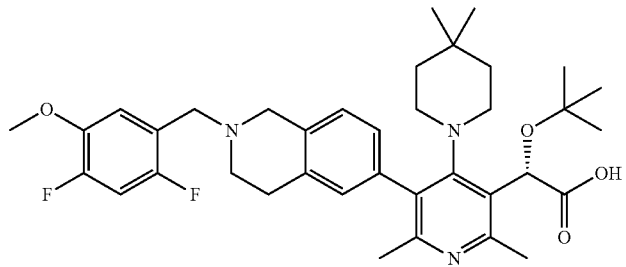 [SMILES: COc1cc(CN2CCc3cc(-c4c(C)nc(C)c([C@H](OC(C)(C)C)C(=O)O)c4N4CCC(C)(C)CC4)ccc3C2)c(F)cc1F]<br>Method A, C: LCMS (M + H) = 636.3 | |
| 95 | (S)-2-(tert-butoxy)-2-(5-(2-(3,5-difluoro-4-methoxybenzyl)-1,2,3,4-tetrahydroisoquinolin-6-yl)-4-(4,4-dimethylpiperidin-1-yl)-2,6-dimethylpyridin-3-yl)acetic acid<br>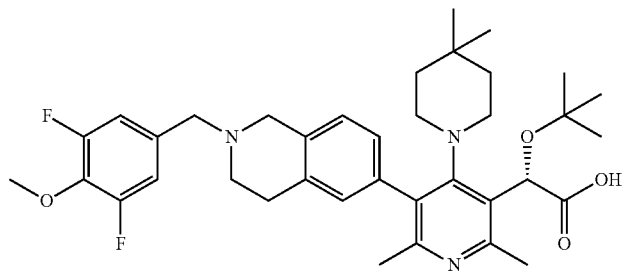 [SMILES: COc1c(F)cc(CN2CCc3cc(-c4c(C)nc(C)c([C@H](OC(C)(C)C)C(=O)O)c4N4CCC(C)(C)CC4)ccc3C2)cc1F]<br>Method A, C: LCMS (M + H) = 636.5 | |
| 96 | (S)-2-(tert-butoxy)-2-(4-(4,4-dimethylpiperidin-1-yl)-2,6-dimethyl-5-(2-(2,3,5-trifluorobenzyl)-1,2,3,4-tetrahydroisoquinolin-6-yl)pyridin-3-yl)acetic acid<br>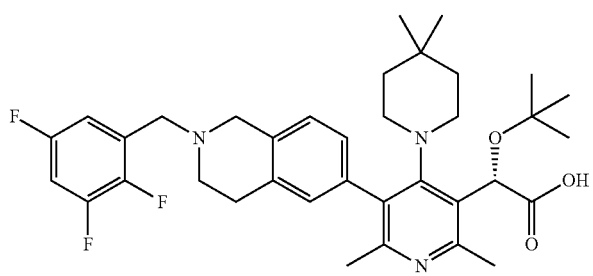 [SMILES: Cc1nc(C)c([C@H](OC(C)(C)C)C(=O)O)c(N2CCC(C)(C)CC2)c1-c1ccc2c(c1)CCN(Cc1cc(F)cc(F)c1F)C2]<br>Method C: LCMS (M + H) = 624.3 | |
| 97 | (S)-2-(tert-butoxy)-2-(4-(4,4-dimethylpiperidin-1-yl)-5-(2-(3-fluoro-4-methoxybenzyl)-1,2,3,4-tetrahydroisoquinolin-6-yl)-2,6-dimethylpyridin-3-yl)acetic acid | |

| Compound | Name<br>General Method Used<br>Structure | LCMS<br>(M + H)+ |
|---|---|---|

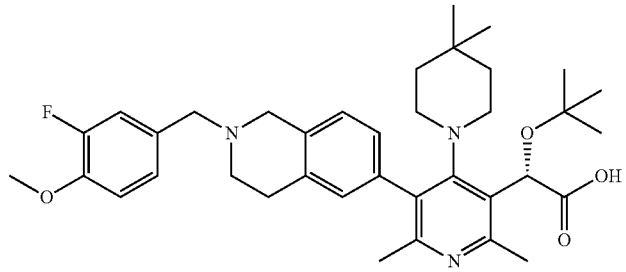 [SMILES: COc1ccc(CN2CCc3cc(-c4c(C)nc(C)c([C@H](OC(C)(C)C)C(=O)O)c4N4CCC(C)(C)CC4)ccc3C2)cc1F]

Method A,: LCMS (M + H) = 618.2

98    (S)-2-(tert-butoxy)-2-(4-(4,4-dimethylpiperidin-1-yl)-5-(2-(2-methoxy-3-(trifluoromethyl)benzyl)-1,2,3,4-tetrahydroisoquinolin-6-yl)-2,6-dimethylpyridin-3-yl)acetic acid

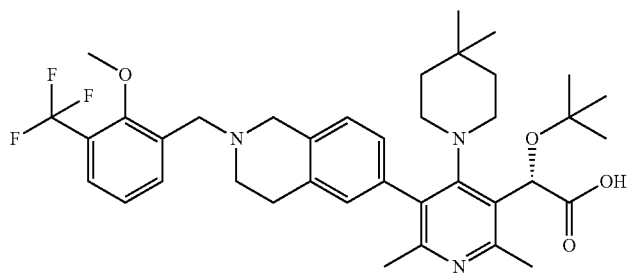 [SMILES: COc1c(CN2CCc3cc(-c4c(C)nc(C)c([C@H](OC(C)(C)C)C(=O)O)c4N4CCC(C)(C)CC4)ccc3C2)cccc1C(F)(F)F]

Method A: LCMS (M + H) = 668.7

99    (S)-2-(tert-butoxy)-2-(5-(2-(5-chloro-2-methoxybenzyl)-1,2,3,4-tetrahydroisoquinolin-6-yl)-4-(4,4-dimethylpiperidin-1-yl)-2,6-dimethylpyridin-3-yl)acetic acid

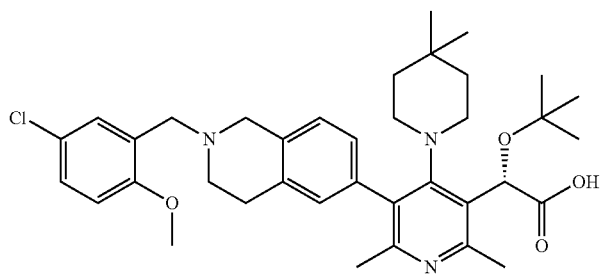 [SMILES: COc1ccc(Cl)cc1CN1CCc2cc(-c3c(C)nc(C)c([C@H](OC(C)(C)C)C(=O)O)c3N3CCC(C)(C)CC3)ccc2C1]

Method A: LCMS (M + H) = 634.4

100    (S)-2-(tert-butoxy)-2-(5-(2-(3-chloro-5-methoxybenzyl)-1,2,3,4-tetrahydroisoquinolin-6-yl)-4-(4,4-dimethylpiperidin-1-yl)-2,6-dimethylpyridin-3-yl)acetic acid

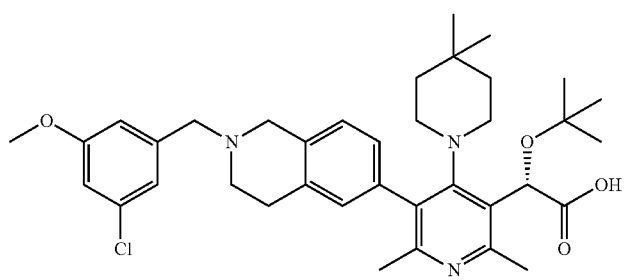 [SMILES: COc1cc(Cl)cc(CN2CCc3cc(-c4c(C)nc(C)c([C@H](OC(C)(C)C)C(=O)O)c4N4CCC(C)(C)CC4)ccc3C2)c1]

Method A: LCMS (M + H) = 634.5

| Compound | Name<br>General Method Used<br>Structure | LCMS<br>(M + H)+ |
|---|---|---|
| 101 | (S)-2-(tert-butoxy)-2-(4-(4,4-dimethylpiperidin-1-yl)-5-(2-(4-fluoro-3-methoxybenzyl)-1,2,3,4-tetrahydroisoquinolin-6-yl)-2,6-dimethylpyridin-3-yl)acetic acid<br><br>Method A: LCMS (M + H) = 618.5 | |
| 102 | (S)-2-(tert-butoxy)-2-(4-(4,4-dimethylpiperidin-1-yl)-2,6-dimethyl-5-(2-(4-(trifluoromethoxy)benzyl)-1,2,3,4-tetrahydroisoquinolin-6-yl)pyridin-3-yl)acetic acid<br><br>Method A: LCMS (M + H) = 654.1 | |
| 103 | (S)-2-(tert-butoxy)-2-(4-(4,4-dimethylpiperidin-1-yl)-5-(2-(3-ethoxybenzyl)-1,2,3,4-tetrahydroisoquinolin-6-yl)-2,6-dimethylpyridin-3-yl)acetic acid<br><br>Method A: LCMS (M + H) = 614.3 | |
| 104 | (S)-2-(tert-butoxy)-2-(5-(2-(3-chloro-4-(trifluoromethoxy)benzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|
| | 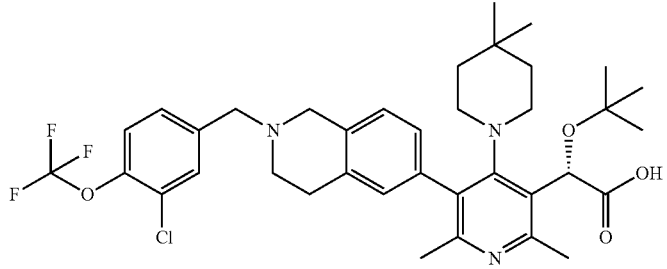 [SMILES: Cc1nc(C)c([C@H](OC(C)(C)C)C(=O)O)c(N2CCC(C)(C)CC2)c1-c1ccc2c(c1)CCN(Cc1ccc(OC(F)(F)F)c(Cl)c1)C2]<br>Method A: LCMS (M + H) = 688.1 | |
| 105 | (S)-2-(tert-butoxy)-2-(5-(2-(4-(difluoromethoxy)-2-fluorobenzyl)-<br>1,2,3,4-tetrahydroisoquinolin-6-yl)-4-(4,4-dimethylpiperidin-1-<br>yl)-2,6-dimethylpyridin-3-yl)acetic acid | |
| | 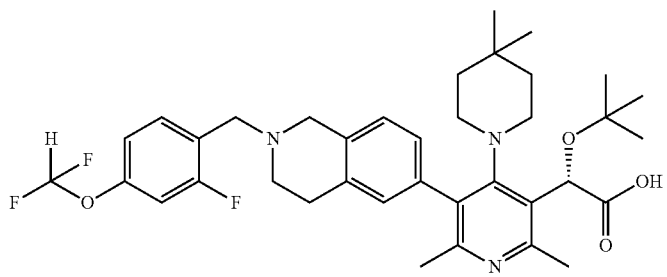 [SMILES: Cc1nc(C)c([C@H](OC(C)(C)C)C(=O)O)c(N2CCC(C)(C)CC2)c1-c1ccc2c(c1)CCN(Cc1ccc(OC(F)F)cc1F)C2]<br>Method A: LCMS (M + H) = 654.2 | |
| 106 | (S)-2-(tert-butoxy)-2-(5-(2-(2,6-difluoro-4-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| | 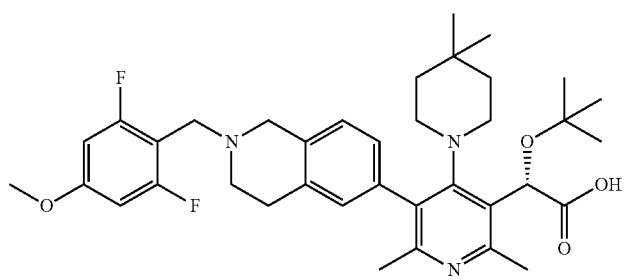 [SMILES: COc1cc(F)c(CN2CCc3cc(-c4c(C)nc(C)c([C@H](OC(C)(C)C)C(=O)O)c4N4CCC(C)(C)CC4)ccc3C2)c(F)c1]<br>Method A: LCMS (M + H) = 636.7 | |
| 107 | (S)-2-(tert-butoxy)-2-(5-(2-(2,4-difluoro-6-methoxybenzyl)-<br>1,2,3,4-tetrahydroisoquinolin-6-yl)-4-(4,4-dimethylpiperidin-1-<br>yl)-2,6-dimethylpyridin-3-yl)acetic acid | |
| | 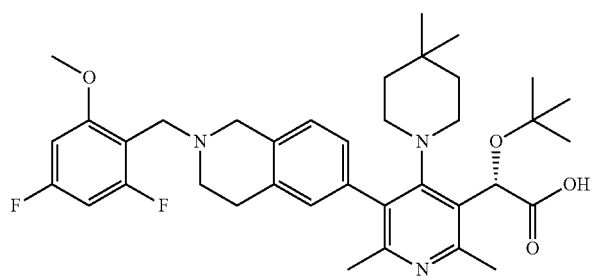 [SMILES: COc1cc(F)cc(F)c1CN1CCc2cc(-c3c(C)nc(C)c([C@H](OC(C)(C)C)C(=O)O)c3N3CCC(C)(C)CC3)ccc2C1]<br>Method A: LCMS (M + H) = 636.7 | |

| Compound | Name<br>General Method Used<br>Structure | LCMS<br>(M + H)+ |
|---|---|---|
| 108 | (S)-2-(tert-butoxy)-2-(4-(4,4-dimethylpiperidin-1-yl)-5-(2-(3-fluoro-4-(trifluoromethoxy)benzyl)-1,2,3,4-tetrahydroisoquinolin-6-yl)-2,6-dimethylpyridin-3-yl)acetic acid<br>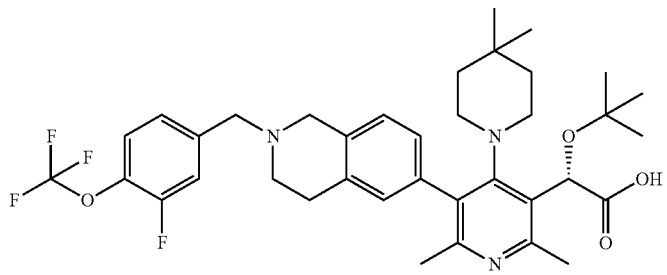<br>Method A: LCMS (M + H) = 672.2 | |
| 109 | (S)-2-(tert-butoxy)-2-(4-(4,4-dimethylpiperidin-1-yl)-5-(2-(2-methoxy-4-(trifluoromethyl)benzyl)-1,2,3,4-tetrahydroisoquinolin-6-yl)-2,6-dimethylpyridin-3-yl)acetic acid<br>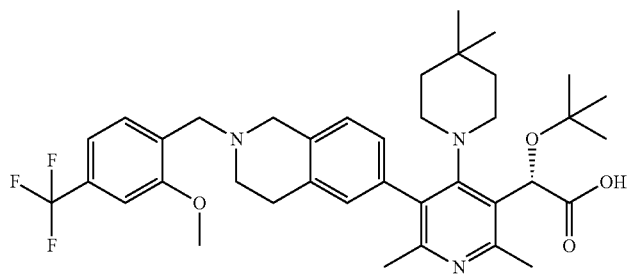 [SMILES: COc1cc(C(F)(F)F)ccc1CN1CCc2cc(-c3c(C)nc(C)c([C@H](OC(C)(C)C)C(=O)O)c3N3CCC(C)(C)CC3)ccc2C1]<br>Method A: LCMS (M + H) = 668.2 | |
| 110 | (S)-2-(tert-butoxy)-2-(4-(4,4-dimethylpiperidin-1-yl)-2,6-dimethyl-5-(2-(3-(trifluoromethoxy)benzyl)-1,2,3,4-tetrahydroisoquinolin-6-yl)pyridin-3-yl)acetic acid<br>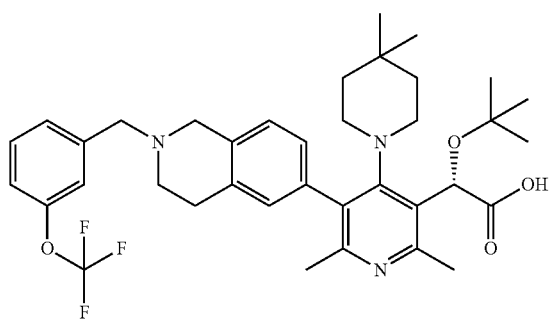 [SMILES: Cc1nc(C)c([C@H](OC(C)(C)C)C(=O)O)c(N2CCC(C)(C)CC2)c1-c1ccc2c(c1)CCN(Cc1cccc(OC(F)(F)F)c1)C2]<br>Method A, C: LCMS (M + H) = 654.4 | |
| 111 | (S)-2-(tert-butoxy)-2-(4-(4,4-dimethylpiperidin-1-yl)-5-(2-(3-fluoro-5-(trifluoromethoxy)benzyl)-1,2,3,4-tetrahydroisoquinolin-6-yl)-2,6-dimethylpyridin-3-yl)acetic acid | |

| Compound | Name<br>General Method Used<br>Structure | LCMS<br>(M + H)+ |
|---|---|---|

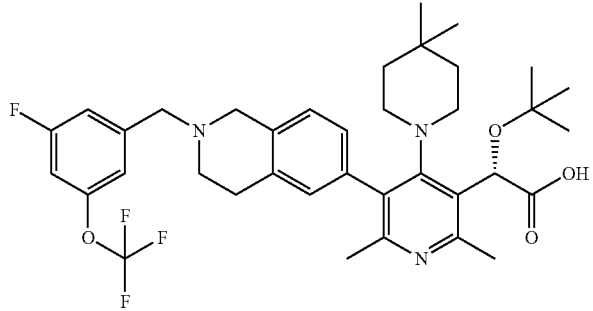 [SMILES: Cc1nc(C)c([C@H](OC(C)(C)C)C(=O)O)c(N2CCC(C)(C)CC2)c1-c1ccc2c(c1)CCN(Cc1cc(F)cc(OC(F)(F)F)c1)C2]

Method A: LCMS (M + H) = 672.2

112    (S)-2-(tert-butoxy)-2-(4-(4,4-dimethylpiperidin-1-yl)-5-(2-(3-methoxy-5-(trifluoromethyl)benzyl)-1,2,3,4-tetrahydroisoquinolin-6-yl)-2,6-dimethylpyridin-3-yl)acetic acid

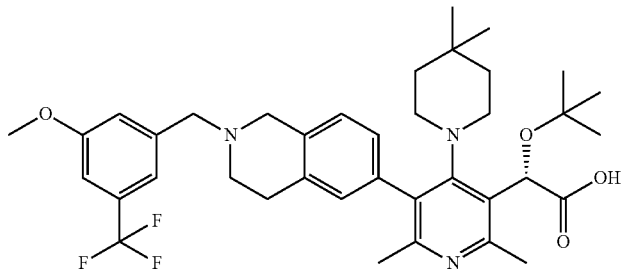 [SMILES: COc1cc(CN2CCc3cc(-c4c(C)nc(C)c([C@H](OC(C)(C)C)C(=O)O)c4N4CCC(C)(C)CC4)ccc3C2)cc(C(F)(F)F)c1]

Method A: LCMS (M + H) = 668.2

113    (S)-2-(tert-butoxy)-2-(5-(2-(3-chloro-5-(trifluoromethoxy)benzyl)-1,2,3,4-tetrahydroisoquinolin-6-yl)-4-(4,4-dimethylpiperidin-1-yl)-2,6-dimethylpyridin-3-yl)acetic acid

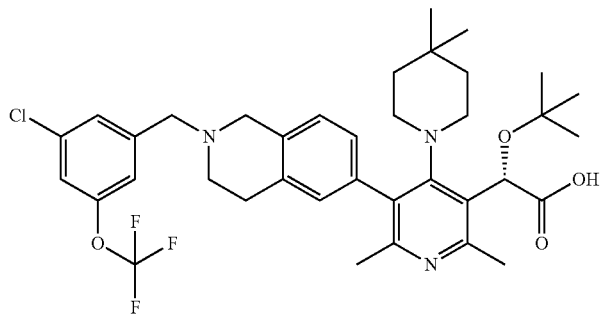 [SMILES: Cc1nc(C)c([C@H](OC(C)(C)C)C(=O)O)c(N2CCC(C)(C)CC2)c1-c1ccc2c(c1)CCN(Cc1cc(Cl)cc(OC(F)(F)F)c1)C2]

Method A: LCMS (M + H) = 688.3

114    (S)-2-(tert-butoxy)-2-(5-(2-(2-(difluoromethoxy)benzyl)-1,2,3,4-tetrahydroisoquinolin-6-yl)-4-(4,4-dimethylpiperidin-1-yl)-2,6-dimethylpyridin-3-yl)acetic acid

| Compound | Name<br>General Method Used<br>Structure | LCMS<br>(M + H)+ |
|---|---|---|

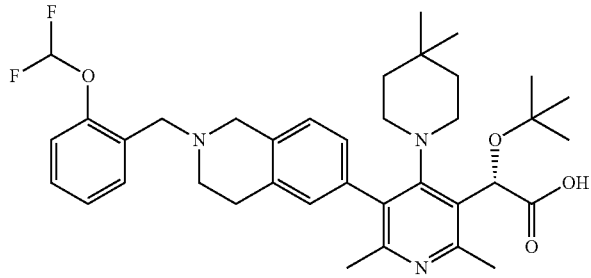 [SMILES: Cc1nc(C)c([C@H](OC(C)(C)C)C(=O)O)c(N2CCC(C)(C)CC2)c1-c1ccc2c(c1)CCN(Cc1ccccc1OC(F)F)C2]

Method A: LCMS (M + H) = 636.4

115    (S)-2-(tert-butoxy)-2-(4-(4,4-dimethylpiperidin-1-yl)-5-(2-(2-fluoro-6-methoxybenzyl)-1,2,3,4-tetrahydroisoquinolin-6-yl)-2,6-dimethylpyridin-3-yl)acetic acid

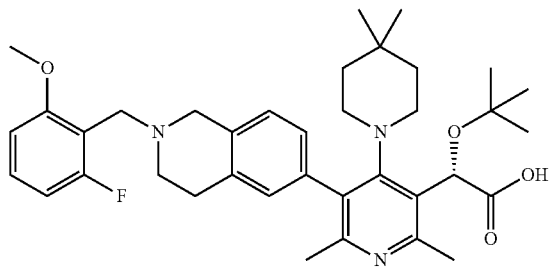 [SMILES: COc1cccc(F)c1CN1CCc2cc(-c3c(C)nc(C)c([C@H](OC(C)(C)C)C(=O)O)c3N3CCC(C)(C)CC3)ccc2C1]

Method C: LCMS (M + H) = 618.2

116    (S)-2-(tert-butoxy)-2-(4-(4,4-dimethylpiperidin-1-yl)-5-(2-(2-fluoro-5-methoxybenzyl)-1,2,3,4-tetrahydroisoquinolin-6-yl)-2,6-dimethylpyridin-3-yl)acetic acid

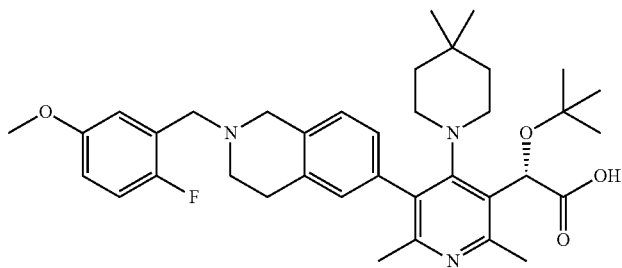 [SMILES: COc1ccc(F)c(CN2CCc3cc(-c4c(C)nc(C)c([C@H](OC(C)(C)C)C(=O)O)c4N4CCC(C)(C)CC4)ccc3C2)c1]

Method C: LCMS (M + H) = 618.2

117    (S)-2-(tert-butoxy)-2-(4-(4,4-dimethylpiperidin-1-yl)-5-(2-(4-fluoro-2-methoxybenzyl)-1,2,3,4-tetrahydroisoquinolin-6-yl)-2,6-dimethylpyridin-3-yl)acetic acid

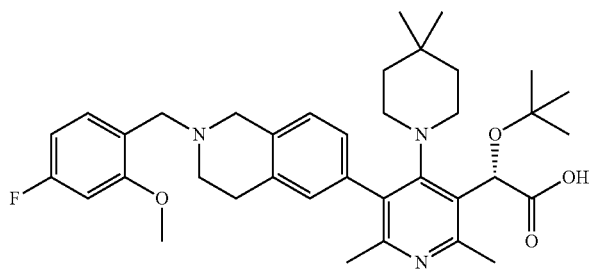 [SMILES: COc1cc(F)ccc1CN1CCc2cc(-c3c(C)nc(C)c([C@H](OC(C)(C)C)C(=O)O)c3N3CCC(C)(C)CC3)ccc2C1]

-continued

| Compound | Name<br>General Method Used<br>Structure | LCMS<br>(M + H)+ |
|---|---|---|
| | Method C: $^1$H NMR (500 MHz, DMSO-d$_6$) δ 7.37 (t, J = 7.7 Hz, 1H), 7.15-7.01 (m, 2H), 6.94-6.83 (m, 2H), 6.75 (t, J = 8.3 Hz, 1H), 5.75 (d, J = 9.5 Hz, 1H), 3.84-3.77 (m, 3H), 3.62 (br. s., 1H), 2.91-2.62 (m, 8H), 2.42 (s, 3H), 2.11-2.03 (m, 3H), 1.89 (s, 8H), 1.10 (s, 9H), 0.84 (br. s., 3H), 0.61 (br. s., 3H). LCMS (M + H) = 618.2 | |
| 118 | (S)-2-(tert-butoxy)-2-(5-(2-(3-(difluoromethoxy)benzyl)-1,2,3,4-tetrahydroisoquinolin-6-yl)-4-(4,4-dimethylpiperidin-1-yl)-2,6-dimethylpyridin-3-yl)acetic acid | |

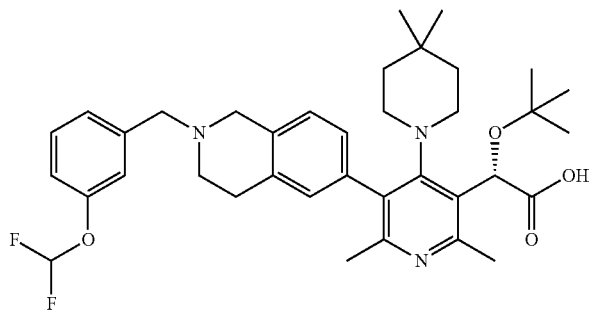 [SMILES: Cc1nc(C)c([C@H](OC(C)(C)C)C(=O)O)c(N2CCC(C)(C)CC2)c1-c1ccc2c(c1)CCN(Cc1cccc(OC(F)F)c1)C2]

Method C: LCMS (M + H) = 636.2

| 119 | (S)-2-(tert-butoxy)-2-(4-(4,4-dimethylpiperidin-1-yl)-5-(2-(2-methoxy-5-methylbenzyl)-1,2,3,4-tetrahydroisoquinolin-6-yl)-2,6-dimethylpyridin-3-yl)acetic acid | |

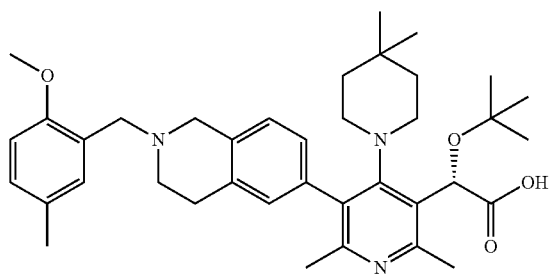 [SMILES: COc1ccc(C)cc1CN1CCc2cc(-c3c(C)nc(C)c([C@H](OC(C)(C)C)C(=O)O)c3N3CCC(C)(C)CC3)ccc2C1]

Method A: LCMS (M + H) = 614.4

| 120 | (S)-2-(tert-butoxy)-2-(4-(4,4-dimethylpiperidin-1-yl)-5-(2-(4-fluoro-3-(trifluoromethoxy)benzyl)-1,2,3,4-tetrahydroisoquinolin-6-yl)-2,6-dimethylpyridin-3-yl)acetic acid | |

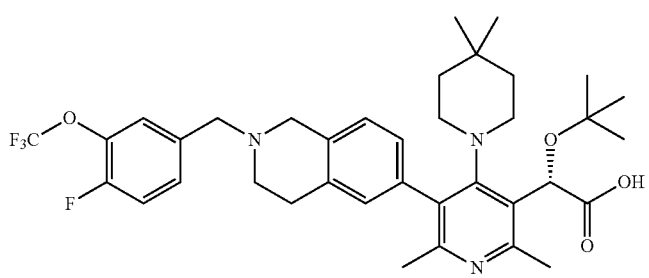 [SMILES: Cc1nc(C)c([C@H](OC(C)(C)C)C(=O)O)c(N2CCC(C)(C)CC2)c1-c1ccc2c(c1)CCN(Cc1ccc(F)c(OC(F)(F)F)c1)C2]

Method C: LCMS (M + H) = 672.2

| 121 | (S)-2-(tert-butoxy)-2-(4-(4,4-dimethylpiperidin-1-yl)-2,6-dimethyl-5-(2-(3-(1,1,2,2-tetrafluoroethoxy)benzyl)-1,2,3,4-tetrahydroisoquinolin-6-yl)pyridin-3-yl)acetic acid | |

| Compound | Name<br>General Method Used<br>Structure | LCMS<br>(M + H)+ |
|---|---|---|
| | 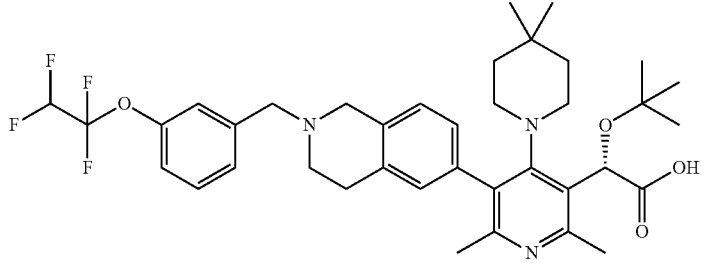 [SMILES: Cc1nc(C)c([C@H](OC(C)(C)C)C(=O)O)c(N2CCC(C)(C)CC2)c1-c1ccc2c(c1)CCN(Cc1cccc(OC(F)(F)C(F)F)c1)C2]<br>Method C: LCMS (M + H) = 686.2 | |
| 122 | (S)-2-(tert-butoxy)-2-(4-(4,4-dimethylpiperidin-1-yl)-5-(2-(3-fluoro-5-methoxybenzyl)-1,2,3,4-tetrahydroisoquinolin-6-yl)-2,6-dimethylpyridin-3-yl)acetic acid | |
| | 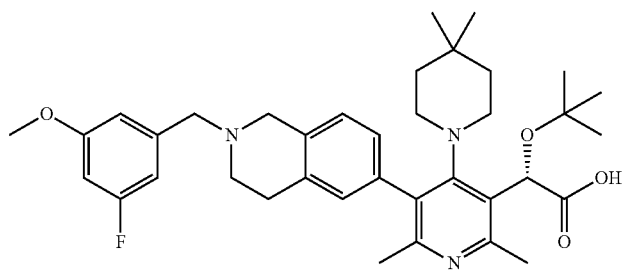 [SMILES: COc1cc(F)cc(CN2CCc3cc(-c4c(C)nc(C)c([C@H](OC(C)(C)C)C(=O)O)c4N4CCC(C)(C)CC4)ccc3C2)c1]<br>Method C: LCMS (M + H) = 618.2 | |
| 123 | (S)-2-(tert-butoxy)-2-(4-(4,4-dimethylpiperidin-1-yl)-2,6-dimethyl-5-(2-(2-(trifluoromethoxy)benzyl)-1,2,3,4-tetrahydroisoquinolin-6-yl)pyridin-3-yl)acetic acid | |
| | 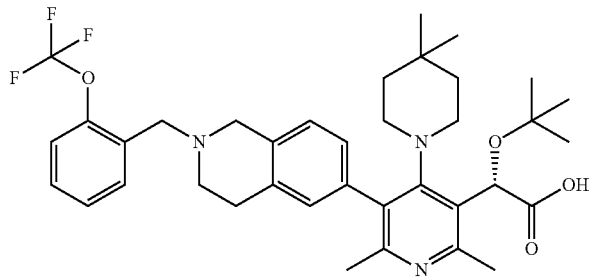 [SMILES: Cc1nc(C)c([C@H](OC(C)(C)C)C(=O)O)c(N2CCC(C)(C)CC2)c1-c1ccc2c(c1)CCN(Cc1ccccc1OC(F)(F)F)C2]<br>Method A: LCMS (M + H) = 654.3 | |
| 124 | (S)-2-(tert-butoxy)-2-(4-(4,4-dimethylpiperidin-1-yl)-5-(2-(5-fluoro-2-methoxybenzyl)-1,2,3,4-tetrahydroisoquinolin-6-yl)-2,6-dimethylpyridin-3-yl)acetic acid | |
| | 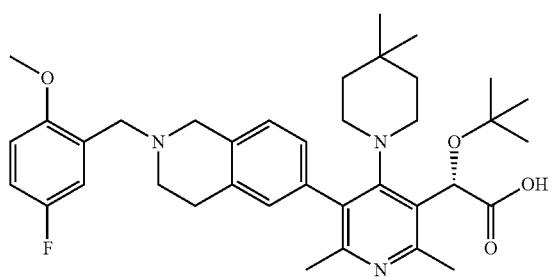<br>Method A: LCMS (M + H) = 618.4 | |

| Compound | Name<br>General Method Used<br>Structure | LCMS<br>(M + H)+ |
|---|---|---|
| 125 | (S)-2-(tert-butoxy)-2-(4-(4,4-dimethylpiperidin-1-yl)-2,6-dimethyl-5-(2-(4-(1,1,2,2-tetrafluoroethoxy)benzyl)-1,2,3,4-tetrahydroisoquinolin-6-yl)pyridin-3-yl)acetic acid<br><br>Method C: LCMS (M + H) = 686.2 | |
| 126 | (S)-2-(tert-butoxy)-2-(4-(4,4-dimethylpiperidin-1-yl)-5-(2-(5-ethoxy-2,4-difluorobenzyl)-1,2,3,4-tetrahydroisoquinolin-6-yl)-2,6-dimethylpyridin-3-yl)acetic acid<br><br>Method A: LCMS (M + H) = 650.4 | |
| 127 | (S)-2-(tert-butoxy)-2-(5-(2-(3,4-dichlorobenzyl)-1,2,3,4-tetrahydroisoquinolin-6-yl)-4-(4,4-dimethylpiperidin-1-yl)-2,6-dimethylpyridin-3-yl)acetic acid<br><br>Method C: LCMS (M + H) = 638.1 | |
| 128 | (S)-2-(tert-butoxy)-2-(5-(2-(2,6-dichlorobenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|
| | 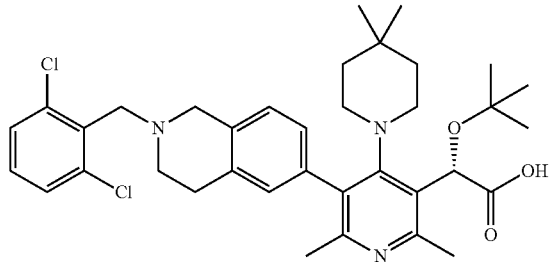<br>Method C: LCMS (M + H) = 638.1 | |
| 129 | (S)-2-(tert-butoxy)-2-(5-(2-(2-chloro-3-methoxybenzyl)-1,2,3,4-tetrahydroisoquinolin-6-yl)-4-(4,4-dimethylpiperidin-1-yl)-2,6-dimethylpyridin-3-yl)acetic acid | |
| | 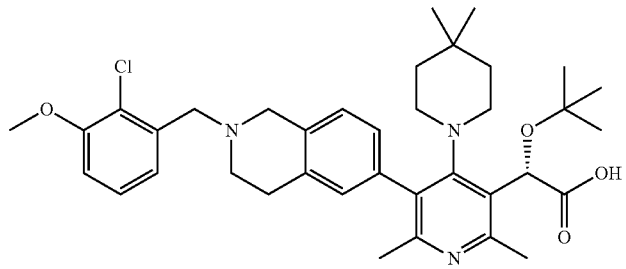 [SMILES: COc1cccc(CN2CCc3cc(-c4c(C)nc(C)c([C@H](OC(C)(C)C)C(=O)O)c4N4CCC(C)(C)CC4)ccc3C2)c1Cl]<br>Method C: LCMS (M + H) = 634.2 | |
| 130 | (S)-2-(tert-butoxy)-2-(5-(2-(3-chloro-2-fluorobenzyl)-1,2,3,4-tetrahydroisoquinolin-6-yl)-4-(4,4-dimethylpiperidin-1-yl)-2,6-dimethylpyridin-3-yl)acetic acid | |
| | 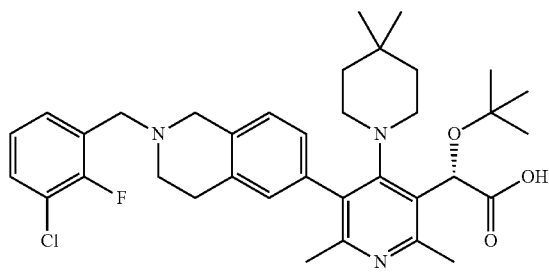 [SMILES: Cc1nc(C)c([C@H](OC(C)(C)C)C(=O)O)c(N2CCC(C)(C)CC2)c1-c1ccc2c(c1)CCN(Cc1cccc(Cl)c1F)C2]<br>Method C: LCMS (M + H) = 622.1 | |
| 131 | (S)-2-(tert-butoxy)-2-(5-(2-(4-chloro-2-methylbenzyl)-1,2,3,4-tetrahydroisoquinolin-6-yl)-4-(4,4-dimethylpiperidin-1-yl)-2,6-dimethylpyridin-3-yl)acetic acid | |
| | 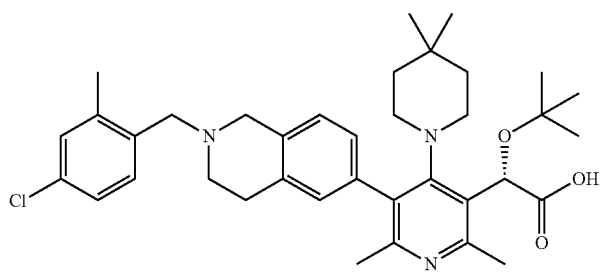 [SMILES: Cc1cc(Cl)ccc1CN1CCc2cc(-c3c(C)nc(C)c([C@H](OC(C)(C)C)C(=O)O)c3N3CCC(C)(C)CC3)ccc2C1]<br>Method C: LCMS (M + H) = 618.1 | |

| Compound | Name<br>General Method Used<br>Structure | LCMS<br>(M + H)+ |
|---|---|---|
| 132 | (S)-2-(tert-butoxy)-2-(5-(2-(3-chloro-4-methylbenzyl)-1,2,3,4-tetrahydroisoquinolin-6-yl)-4-(4,4-dimethylpiperidin-1-yl)-2,6-dimethylpyridin-3-yl)acetic acid<br>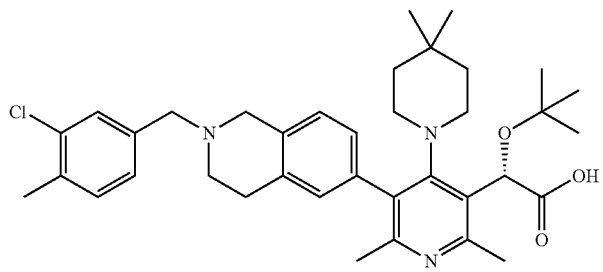 [SMILES: Cc1ccc(CN2CCc3cc(-c4c(C)nc(C)c([C@H](OC(C)(C)C)C(=O)O)c4N4CCC(C)(C)CC4)ccc3C2)cc1Cl]<br>Method C: LCMS (M + H) = 618.1 | |
| 133 | (S)-2-(tert-butoxy)-2-(5-(2-(5-chloro-2-methylbenzyl)-1,2,3,4-tetrahydroisoquinolin-6-yl)-4-(4,4-dimethylpiperidin-1-yl)-2,6-dimethylpyridin-3-yl)acetic acid<br>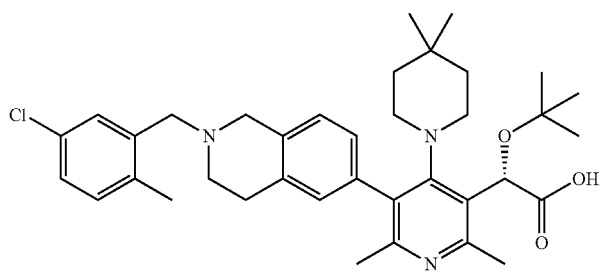 [SMILES: Cc1ccc(Cl)cc1CN1CCc2cc(-c3c(C)nc(C)c([C@H](OC(C)(C)C)C(=O)O)c3N3CCC(C)(C)CC3)ccc2C1]<br>Method C: LCMS (M + H) = 618.1 | |
| 134 | (S)-2-(tert-butoxy)-2-(5-(2-(4-chloro-3-methylbenzyl)-1,2,3,4-tetrahydroisoquinolin-6-yl)-4-(4,4-dimethylpiperidin-1-yl)-2,6-dimethylpyridin-3-yl)acetic acid<br>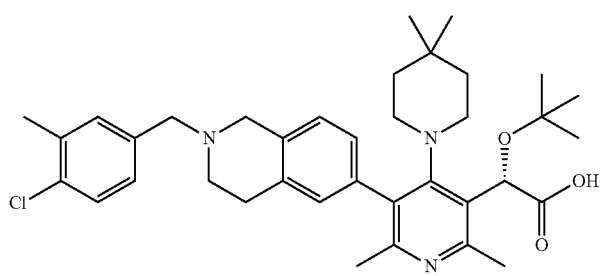 [SMILES: Cc1cc(CN2CCc3cc(-c4c(C)nc(C)c([C@H](OC(C)(C)C)C(=O)O)c4N4CCC(C)(C)CC4)ccc3C2)ccc1Cl]<br>Method C: LCMS (M + H) = 618.1 | |
| 135 | (S)-2-(tert-butoxy)-2-(5-(2-(4-chloro-2,6-difluorobenzyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|
| | 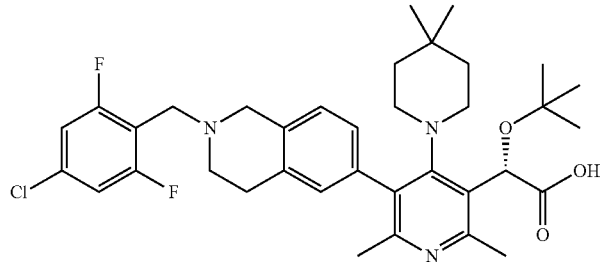 [SMILES: Cc1nc(C)c([C@H](OC(C)(C)C)C(=O)O)c(N2CCC(C)(C)CC2)c1-c1ccc2c(c1)CCN(Cc1c(F)cc(Cl)cc1F)C2]<br>Method C: LCMS (M + H) = 640.1 | |
| 136 | (S)-2-(tert-butoxy)-2-(5-(2-(2-chloro-6-fluorobenzyl)-1,2,3,4-tetrahydroisoquinolin-6-yl)-4-(4,4-dimethylpiperidin-1-yl)-2,6-dimethylpyridin-3-yl)acetic acid | |
| | 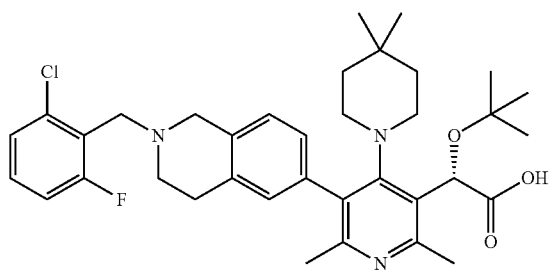<br>Method C: LCMS (M + H) = 622.1 | |
| 137 | (S)-2-(tert-butoxy)-2-(5-(2-(3-chloro-4-methoxybenzyl)-1,2,3,4-tetrahydroisoquinolin-6-yl)-4-(4,4-dimethylpiperidin-1-yl)-2,6-dimethylpyridin-3-yl)acetic acid | |
| | 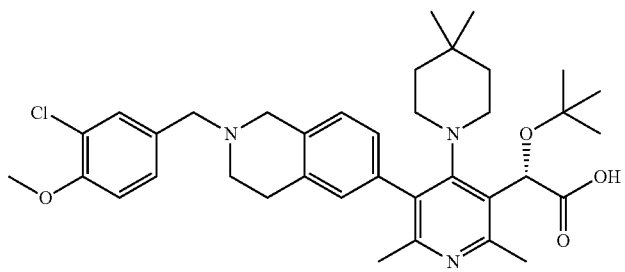 [SMILES: COc1ccc(CN2CCc3cc(-c4c(C)nc(C)c([C@H](OC(C)(C)C)C(=O)O)c4N4CCC(C)(C)CC4)ccc3C2)cc1Cl]<br>Method C: LCMS (M + H) = 634.1 | |
| 138 | (S)-2-(tert-butoxy)-2-(5-(2-(4-chloro-3-methoxybenzyl)-1,2,3,4-tetrahydroisoquinolin-6-yl)-4-(4,4-dimethylpiperidin-1-yl)-2,6-dimethylpyridin-3-yl)acetic acid | |
| | 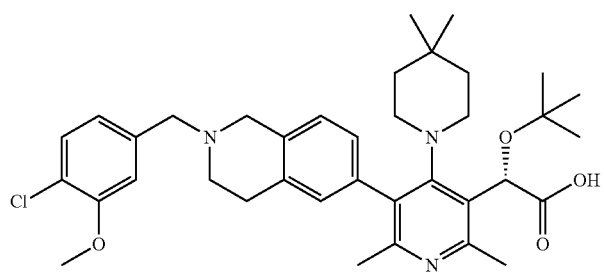 [SMILES: COc1cc(CN2CCc3cc(-c4c(C)nc(C)c([C@H](OC(C)(C)C)C(=O)O)c4N4CCC(C)(C)CC4)ccc3C2)ccc1Cl]<br>Method C: LCMS (M + H) = 634.1 | |

| Compound | Name General Method Used Structure | LCMS (M + H)+ |
|---|---|---|
| 139 | (S)-2-(tert-butoxy)-2-(4-(4,4-dimethylpiperidin-1-yl)-5-(2-(5-isopropyl-2-methoxybenzyl)-1,2,3,4-tetrahydroisoquinolin-6-yl)-2,6-dimethylpyridin-3-yl)acetic acid<br>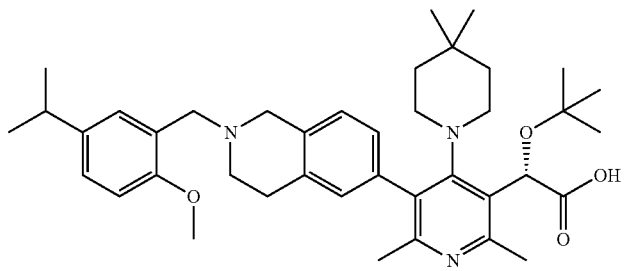 [SMILES: COc1ccc(C(C)C)cc1CN1CCc2cc(-c3c(C)nc(C)c([C@H](OC(C)(C)C)C(=O)O)c3N3CCC(C)(C)CC3)ccc2C1]<br>Method C: LCMS (M + H) = 642.2 | |
| 140 | (S)-2-(tert-butoxy)-2-(4-(4,4-dimethylpiperidin-1-yl)-5-(2-(3-methoxy-4-methylbenzyl)-1,2,3,4-tetrahydroisoquinolin-6-yl)-2,6-dimethylpyridin-3-yl)acetic acid<br>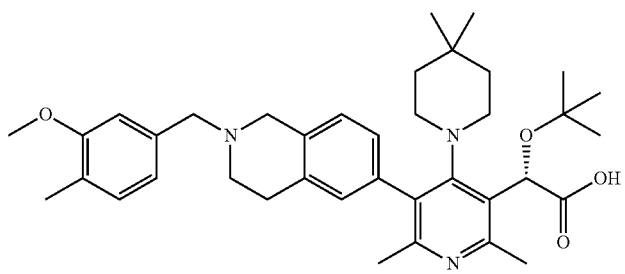 [SMILES: COc1cc(CN2CCc3cc(-c4c(C)nc(C)c([C@H](OC(C)(C)C)C(=O)O)c4N4CCC(C)(C)CC4)ccc3C2)ccc1C]<br>Method C: LCMS (M + H) = 614.2 | |
| 141 | (S)-2-(tert-butoxy)-2-(4-(4,4-dimethylpiperidin-1-yl)-5-(2-(4-methoxy-3-methylbenzyl)-1,2,3,4-tetrahydroisoquinolin-6-yl)-2,6-dimethylpyridin-3-yl)acetic acid<br>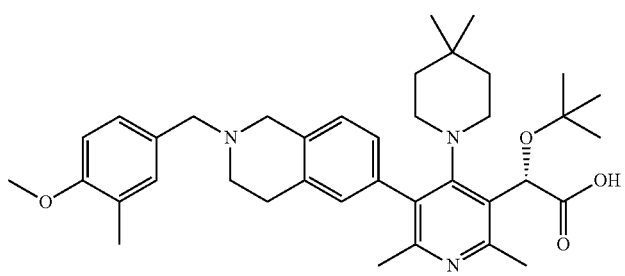 [SMILES: COc1ccc(CN2CCc3cc(-c4c(C)nc(C)c([C@H](OC(C)(C)C)C(=O)O)c4N4CCC(C)(C)CC4)ccc3C2)cc1C]<br>Method C: LCMS (M + H) = 614.2 | |
| 142 | (S)-2-(tert-butoxy)-2-(4-(4,4-dimethylpiperidin-1-yl)-5-(2-(3-fluoro-2-methoxybenzyl)-1,2,3,4-tetrahydroisoquinolin-6-yl)-2,6-dimethylpyridin-3-yl)acetic acid | |

| Compound | Name<br>General Method Used<br>Structure | LCMS<br>(M + H)+ |
|---|---|---|
| | 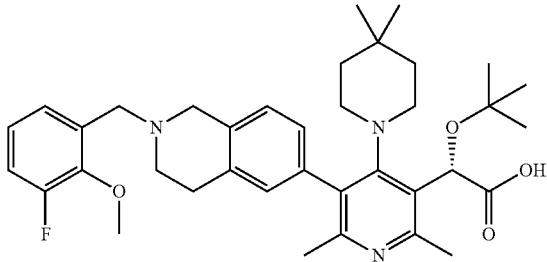 [SMILES: COc1c(F)cccc1CN1CCc2cc(-c3c(C)nc(C)c([C@H](OC(C)(C)C)C(=O)O)c3N3CCC(C)(C)CC3)ccc2C1]<br>Method C: LCMS (M + H) = 618.3 | |
| 143 | (S)-2-(tert-butoxy)-2-(4-(4,4-dimethylpiperidin-1-yl)-5-(2-(3-isopropyl-4-methoxybenzyl)-1,2,3,4-tetrahydroisoquinolin-6-yl)-2,6-dimethylpyridin-3-yl)acetic acid | |
| | 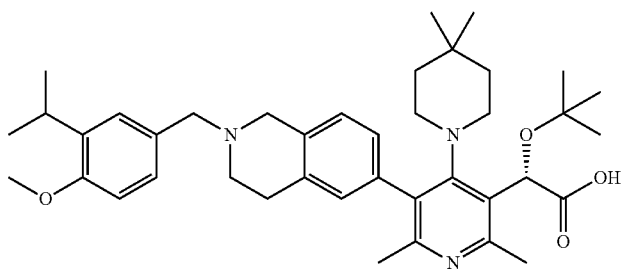 [SMILES: COc1ccc(CN2CCc3cc(-c4c(C)nc(C)c([C@H](OC(C)(C)C)C(=O)O)c4N4CCC(C)(C)CC4)ccc3C2)cc1C(C)C]<br>Method C: LCMS (M + H) = 642.4 | |
| 144 | (S)-2-(tert-butoxy)-2-(5-(2-(2,4-difluoro-6-hydroxybenzyl)-1,2,3,4-tetrahydroisoquinolin-6-yl)-4-(4,4-dimethylpiperidin-1-yl)-2,6-dimethylpyridin-3-yl)acetic acid | |
| | 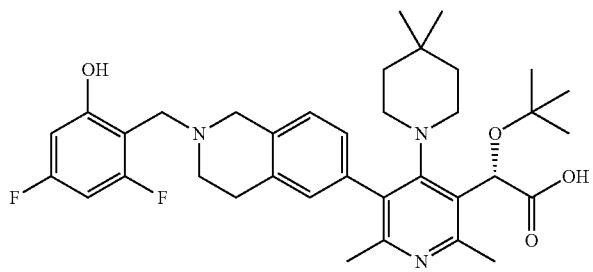 [SMILES: Cc1nc(C)c([C@H](OC(C)(C)C)C(=O)O)c(N2CCC(C)(C)CC2)c1-c1ccc2c(c1)CCN(Cc1c(O)cc(F)cc1F)C2]<br>Method C: LCMS (M + H) = 622.3 | |
| 145 | (S)-2-(tert-butoxy)-2-(5-(2-(2-chloro-6-methoxybenzyl)-1,2,3,4-tetrahydroisoquinolin-6-yl)-4-(4,4-dimethylpiperidin-1-yl)-2,6-dimethylpyridin-3-yl)acetic acid | |
| | 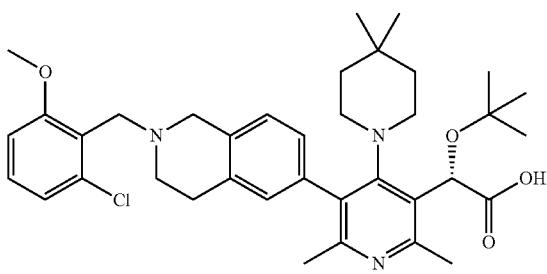<br>Method C: LCMS (M + H) = 634.5 | |

| Compound | Name<br>General Method Used<br>Structure | LCMS<br>(M + H)⁺ |
| --- | --- | --- |
| 146 | (S)-2-(tert-butoxy)-2-(4-(4,4-dimethylpiperidin-1-yl)-5-(2-(2-fluoro-4-methoxybenzyl)-1,2,3,4-tetrahydroisoquinolin-6-yl)-2,6-dimethylpyridin-3-yl)acetic acid<br>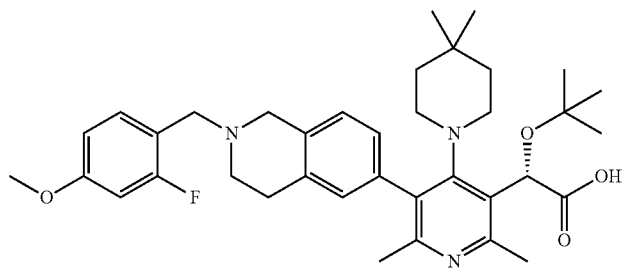 [SMILES: COc1ccc(CN2CCc3cc(-c4c(C)nc(C)c([C@H](OC(C)(C)C)C(=O)O)c4N4CCC(C)(C)CC4)ccc3C2)c(F)c1]<br>Method C: LCMS (M + H) = 618.5 | |
| 147 | (S)-2-(tert-butoxy)-2-(4-(4,4-dimethylpiperidin-1-yl)-5-(2-(4-methoxy-2,3-dimethylbenzyl)-1,2,3,4-tetrahydroisoquinolin-6-yl)-2,6-dimethylpyridin-3-yl)acetic acid<br>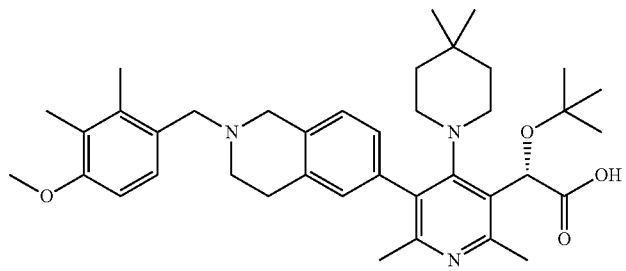 [SMILES: COc1ccc(CN2CCc3cc(-c4c(C)nc(C)c([C@H](OC(C)(C)C)C(=O)O)c4N4CCC(C)(C)CC4)ccc3C2)c(C)c1C]<br>Method C: LCMS (M + H) = 628.2 | |
| 148 | (S)-2-(tert-butoxy)-2-(4-(4,4-dimethylpiperidin-1-yl)-5-(2-(4-methoxy-2,5-dimethylbenzyl)-1,2,3,4-tetrahydroisoquinolin-6-yl)-2,6-dimethylpyridin-3-yl)acetic acid<br>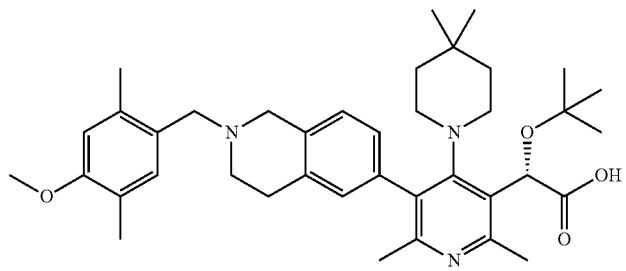 [SMILES: COc1cc(C)c(CN2CCc3cc(-c4c(C)nc(C)c([C@H](OC(C)(C)C)C(=O)O)c4N4CCC(C)(C)CC4)ccc3C2)cc1C]<br>Method C: LCMS (M + H) = 628.4 | |
| 149 | (S)-2-(tert-butoxy)-2-(4-(4,4-dimethylpiperidin-1-yl)-5-(2-(4-ethoxybenzyl)-1,2,3,4-tetrahydroisoquinolin-6-yl)-2,6-dimethylpyridin-3-yl)acetic acid | |

| Compound | Name<br>General Method Used<br>Structure | LCMS<br>(M + H)+ |
|---|---|---|

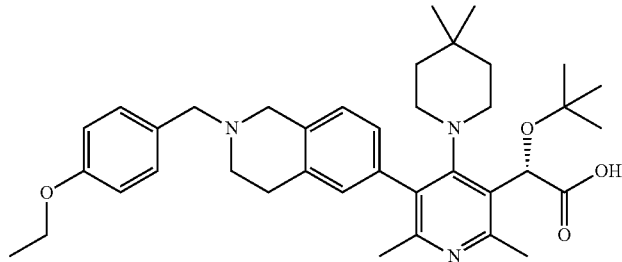 [SMILES: CCOc1ccc(CN2CCc3cc(-c4c(C)nc(C)c([C@H](OC(C)(C)C)C(=O)O)c4N4CCC(C)(C)CC4)ccc3C2)cc1]

Method C: LCMS (M + H) = 614.1

150    (S)-2-(tert-butoxy)-2-(4-(4,4-dimethylpiperidin-1-yl)-5-(2-(4-isopropoxybenzyl)-1,2,3,4-tetrahydroisoquinolin-6-yl)-2,6-dimethylpyridin-3-yl)acetic acid

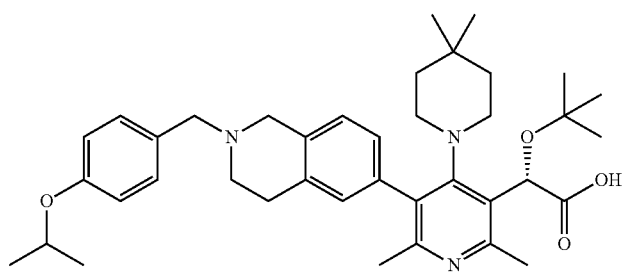 [SMILES: Cc1nc(C)c([C@H](OC(C)(C)C)C(=O)O)c(N2CCC(C)(C)CC2)c1-c1ccc2c(c1)CCN(Cc1ccc(OC(C)C)cc1)C2]

Method C: LCMS (M + H) = 628.2

151    (S)-2-(tert-butoxy)-2-(4-(4,4-dimethylpiperidin-1-yl)-5-(2-(2-methoxy-5-(trifluoromethyl)benzyl)-1,2,3,4-tetrahydroisoquinolin-6-yl)-2,6-dimethylpyridin-3-yl)acetic acid

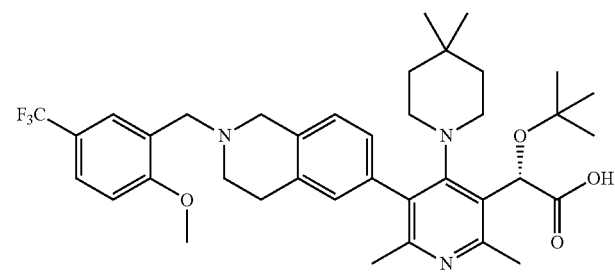 [SMILES: COc1ccc(C(F)(F)F)cc1CN1CCc2cc(-c3c(C)nc(C)c([C@H](OC(C)(C)C)C(=O)O)c3N3CCC(C)(C)CC3)ccc2C1]

Method C: LCMS (M + H) = 668.3

152    (S)-2-(tert-butoxy)-2-(4-(4,4-dimethylpiperidin-1-yl)-5-(2-(2-isopropoxybenzyl)-1,2,3,4-tetrahydroisoquinolin-6-yl)-2,6-dimethylpyridin-3-yl)acetic acid

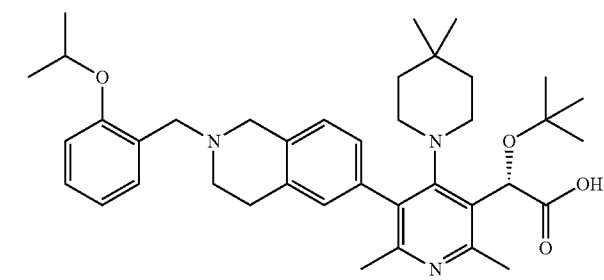 [SMILES: Cc1nc(C)c([C@H](OC(C)(C)C)C(=O)O)c(N2CCC(C)(C)CC2)c1-c1ccc2c(c1)CCN(Cc1ccccc1OC(C)C)C2]

Method C: LCMS (M + H) = 628.4

| Compound | Name<br>General Method Used<br>Structure | LCMS<br>(M + H)+ |
|---|---|---|
| 153 | (S)-2-(tert-butoxy)-2-(4-(4,4-dimethylpiperidin-1-yl)-5-(2-(2-isobutoxybenzyl)-1,2,3,4-tetrahydroisoquinolin-6-yl)-2,6-dimethylpyridin-3-yl)acetic acid<br>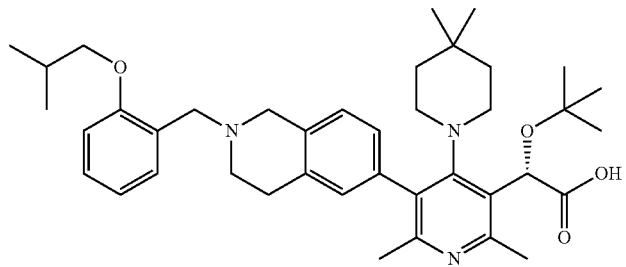 [SMILES: Cc1nc(C)c([C@H](OC(C)(C)C)C(=O)O)c(N2CCC(C)(C)CC2)c1-c1ccc2c(c1)CCN(Cc1ccccc1OCC(C)C)C2]<br>Method C: LCMS (M + H) = 642.4 | |
| 154 | (S)-2-(tert-butoxy)-2-(4-(4,4-dimethylpiperidin-1-yl)-5-(2-(3-isopropoxybenzyl)-1,2,3,4-tetrahydroisoquinolin-6-yl)-2,6-dimethylpyridin-3-yl)acetic acid<br>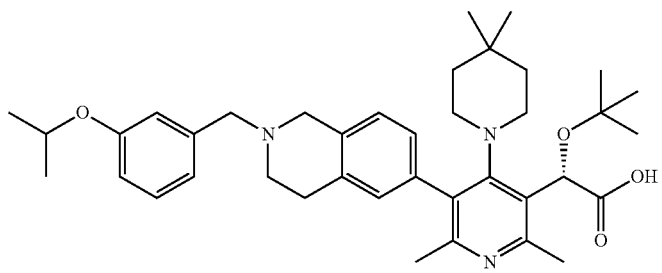 [SMILES: Cc1nc(C)c([C@H](OC(C)(C)C)C(=O)O)c(N2CCC(C)(C)CC2)c1-c1ccc2c(c1)CCN(Cc1cccc(OC(C)C)c1)C2]<br>Method C: LCMS (M + H) = 628.4 | |
| 155 | (S)-2-(tert-butoxy)-2-(5-(2-(chroman-6-ylmethyl)-1,2,3,4-tetrahydroisoquinolin-6-yl)-4-(4,4-dimethylpiperidin-1-yl)-2,6-dimethylpyridin-3-yl)acetic acid<br>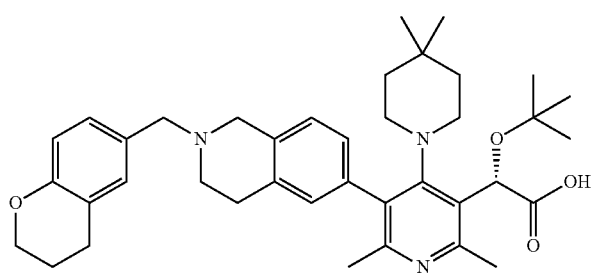 [SMILES: Cc1nc(C)c([C@H](OC(C)(C)C)C(=O)O)c(N2CCC(C)(C)CC2)c1-c1ccc2c(c1)CCN(Cc1ccc3c(c1)CCCO3)C2]<br>Method C: LCMS (M + H) = 626.2 | |
| 156 | (S)-2-(tert-butoxy)-2-(5-(2-((2,3-dihydrobenzo[b][1,4]dioxin-6-yl)methyl)-1,2,3,4-tetrahydroisoquinolin-6-yl)-4-(4,4-dimethylpiperidin-1-yl)-2,6-dimethylpyridin-3-yl)acetic acid | |

| Compound | Name<br>General Method Used<br>Structure | LCMS<br>(M + H)+ |
|---|---|---|

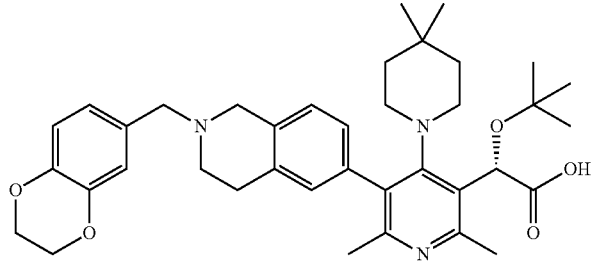

Method C: LCMS (M + H) = 628.2

157    (S)-2-(5-(2-(3,4-bis(difluoromethoxy)benzyl)-1,2,3,4-tetrahydroisoquinolin-6-yl)-4-(4,4-dimethylpiperidin-1-yl)-2,6-dimethylpyridin-3-yl)-2-(tert-butoxy)acetic acid

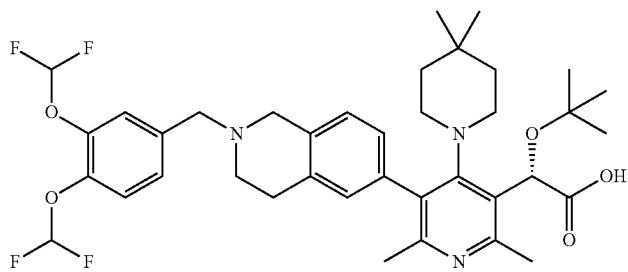 [SMILES: Cc1nc(C)c([C@H](OC(C)(C)C)C(=O)O)c(N2CCC(C)(C)CC2)c1-c1ccc2c(c1)CCN(Cc1ccc(OC(F)F)c(OC(F)F)c1)C2]

Method C: LCMS (M + H) = 702.1

158    (S)-2-(tert-butoxy)-2-(5-(2-((2,3-dihydrobenzo[b][1,4]dioxin-5-yl)methyl)-1,2,3,4-tetrahydroisoquinolin-6-yl)-4-(4,4-dimethylpiperidin-1-yl)-2,6-dimethylpyridin-3-yl)acetic acid

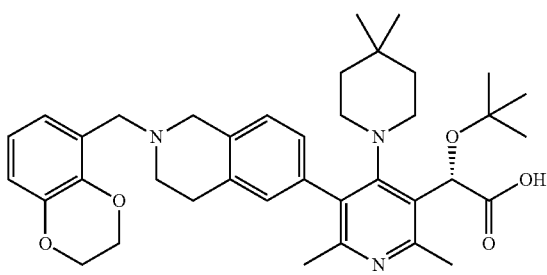 [SMILES: Cc1nc(C)c([C@H](OC(C)(C)C)C(=O)O)c(N2CCC(C)(C)CC2)c1-c1ccc2c(c1)CCN(Cc1cccc3c1OCCO3)C2]

Method C: LCMS (M + H) = 628.2

159    (S)-2-(tert-butoxy)-2-(4-(4,4-dimethylpiperidin-1-yl)-5-(2-(2-fluoro-6-phenoxybenzyl)-1,2,3,4-tetrahydroisoquinolin-6-yl)-2,6-dimethylpyridin-3-yl)acetic acid

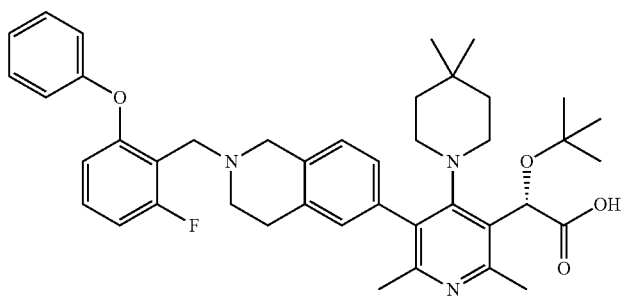 [SMILES: Cc1nc(C)c([C@H](OC(C)(C)C)C(=O)O)c(N2CCC(C)(C)CC2)c1-c1ccc2c(c1)CCN(Cc1c(F)cccc1Oc1ccccc1)C2]

Method C: LCMS (M + H) = 680.2

| Compound | Name<br>General Method Used<br>Structure | LCMS<br>(M + H)⁺ |
|---|---|---|
| 160 | (S)-2-(tert-butoxy)-2-(4-(4,4-dimethylpiperidin-1-yl)-5-(2-(4-isopropoxy-2,6-dimethylbenzyl)-1,2,3,4-tetrahydroisoquinolin-6-yl)-2,6-dimethylpyridin-3-yl)acetic acid | |

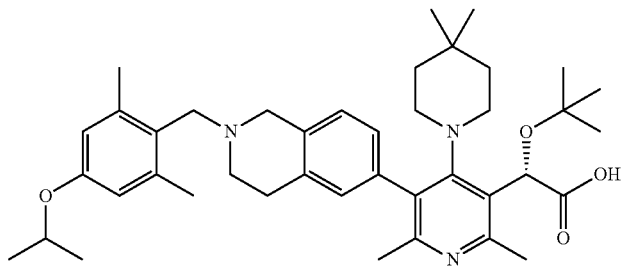 [SMILES: Cc1cc(OC(C)C)cc(C)c1CN1CCc2cc(-c3c(C)nc(C)c([C@H](OC(C)(C)C)C(=O)O)c3N3CCC(C)(C)CC3)ccc2C1]

Method C: LCMS (M + H) = 656.2

| 161 | (S)-2-(tert-butoxy)-2-(5-(2-(3,4-dimethylbenzyl)-1,2,3,4-tetrahydroisoquinolin-6-yl)-4-(4,4-dimethylpiperidin-1-yl)-2,6-dimethylpyridin-3-yl)acetic acid | |

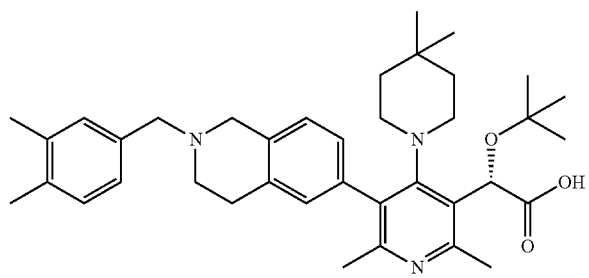

Method A: LCMS (M + H) = 598.4

| 162 | (S)-2-(tert-butoxy)-2-(5-(2-(4-(1-cyanocyclopropyl)benzyl)-1,2,3,4-tetrahydroisoquinolin-6-yl)-4-(4,4-dimethylpiperidin-1-yl)-2,6-dimethylpyridin-3-yl)acetic acid | |

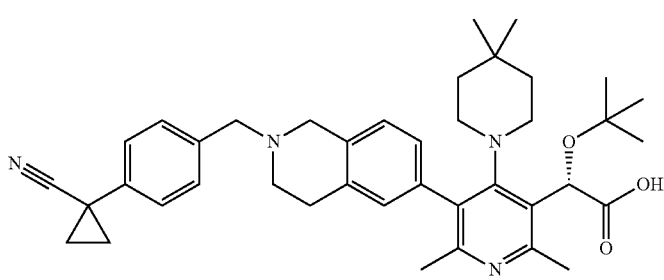 [SMILES: Cc1nc(C)c([C@H](OC(C)(C)C)C(=O)O)c(N2CCC(C)(C)CC2)c1-c1ccc2c(c1)CCN(Cc1ccc(C3(C#N)CC3)cc1)C2]

Method C: LCMS (M + H) = 635.2

| 163 | (S)-2-(tert-butoxy)-2-(4-(4,4-dimethylpiperidin-1-yl)-2,6-dimethyl-5-(2-(4-(nonyloxy)benzyl)-1,2,3,4-tetrahydroisoquinolin-6-yl)pyridin-3-yl)acetic acid | |

| Compound | Name<br>General Method Used<br>Structure | LCMS<br>(M + H)+ |
|---|---|---|
| | 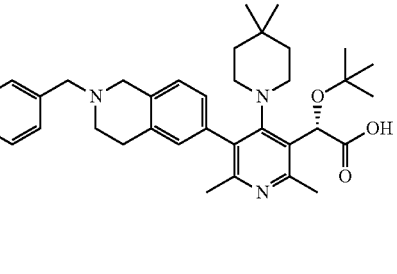<br>Method C: LCMS (M + H) = 712.3 | |

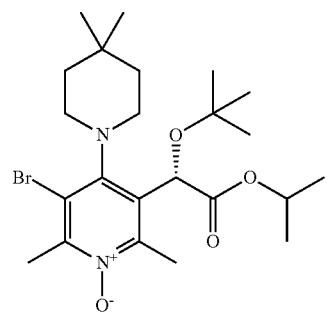 [SMILES: Cc1c(Br)c(N2CCC(C)(C)CC2)c([C@H](OC(C)(C)C)C(=O)OC(C)C)c(C)[n+]1[O-]]

(S)-3-Bromo-5-(1-(tert-butoxy)-2-isopropoxy-2-oxoethyl)-4-(4,4-dimethylpiperidin-1-yl)-2,6-dimethylpyridine 1-oxide: To a stirred solution of (S)-isopropyl 2-(5-bromo-4-(4,4-dimethylpiperidin-1-yl)-2,6-dimethylpyridin-3-yl)-2-(tert-butoxy)acetate (16 g, 34 mmol) in DCM (170 ml) was added mCPBA (77% max) (11.7 g, 51.1 mmol) at rt over 5 min. After 4 h, the reaction mixture was washed with sat aq Na$_2$CO$_3$ (3×50 mL), dried (Na$_2$SO$_4$), filtered and concentrated to give (S)-3-bromo-5-(1-(tert-butoxy)-2-isopropoxy-2-oxoethyl)-4-(4,4-dimethylpiperidin-1-yl)-2,6-dimethylpyridine 1-oxide (14.6 g, 30.1 mmol, 88% yield). $^1$H NMR (500 MHz, chloroform-d) δ 6.28 (br. s., 1H), 5.03 (spt, J=6.3 Hz, 1H), 4.00 (t, J=11.4 Hz, 1H), 3.50 (td, J=12.1, 2.4 Hz, 1H), 2.91-2.79 (m, 1H), 2.76 (s, 3H), 2.67-2.60 (m, 1H), 2.56 (s, 3H), 1.60 (br s, 1H), 1.45 (d, J=12.1 Hz, 1H), 1.38-1.31 (m, 1H), 1.22-1.17 (m, 13H), 1.14 (d, J=6.1 Hz, 3H), 1.10-1.05 (m, 3H), 1.04-1.00 (m, 3H). LCMS (M+)=485.10, 487.10.

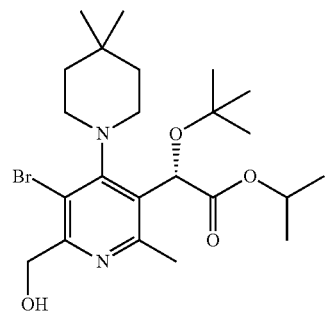 [SMILES: Cc1nc(CO)c(Br)c(N2CCC(C)(C)CC2)c1[C@H](OC(C)(C)C)C(=O)OC(C)C]

Isopropyl (S)-2-(5-bromo-4-(4,4-dimethylpiperidin-1-yl)-6-(hydroxymethyl)-2-methylpyridin-3-yl)-2-(tert-butoxy)acetate: To a stirred solution of (S)-3-bromo-5-(1-(tert-butoxy)-2-isopropoxy-2-oxoethyl)-4-(4,4-dimethylpiperidin-1-yl)-2,6-dimethylpyridine 1-oxide (12.8 g, 26.4 mmol) in anhydrous DCM (132 ml) was added, dropwise, trifluoroacetic anhydride (7.45 ml, 52.7 mmol) over 5 min at rt. After 2 h, sat NaHCO$_3$ (50 mL) was slowly added, stirred for 10 min, aq layer separated, organic layer dried (Na$_2$SO$_4$), filtered, concentrated, adsorbed onto Celite and was purified on silica gel (Biotage, EtOAc/hexanes gradient). The major peak was collected to afford (S)-isopropyl 2-(5-bromo-4-(4,4-dimethylpiperidin-1-yl)-6-(hydroxymethyl)-2-methylpyridin-3-yl)-2-(tert-butoxy)acetate (9.7 g, 20 mmol, 76% yield). $^1$H NMR (500 MHz, chloroform-d) δ 6.24 (br s, 1H), 5.04 (spt, J=6.3 Hz, 1H), 4.75 (br s, 1H), 4.72-4.59 (m, 2H), 4.05 (br s, 1H), 3.48 (t, J=11.0 Hz, 1H), 2.91 (d, J=11.5 Hz, 1H), 2.68-2.62 (m, 1H), 2.60 (s, 3H), 1.63-1.57 (m, 2H), 1.45 (d, J=15.0 Hz, 1H), 1.39-1.32 (m, 1H), 1.22-1.19 (m, 12H), 1.15-1.12 (m, 3H), 1.08 (s, 3H), 1.03 (s, 3H). LCMS (M+H)=485.17, 487.17.

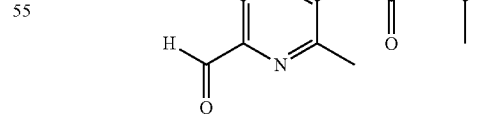

Isopropyl (S)-2-(5-bromo-4-(4,4-dimethylpiperidin-1-yl)-6-formyl-2-methylpyridin-3-yl)-2-(tert-butoxy)acetate: To a stirred solution of (S)-isopropyl 2-(5-bromo-4-(4,4-dimethylpiperidin-1-yl)-6-(hydroxymethyl)-2-methylpyridin-3-yl)-2-(tert-butoxy)acetate (1.0 g, 2.1 mmol) in CH$_2$Cl$_2$ (19 ml) was added Dess-Martin periodinane (1.3 g, 3.1 mmol) at once at rt. After 16 h, the reaction mixture was diluted with ether, washed with 1M NaOH followed by brine. The organic phase was dried over (Na₂SO₄), concentrated and purified on silica gel (Biotage, EtOAc/hexanes gradient, 0-100% over 10 CVs) to afford (S)-isopropyl 2-(5-bromo-4-(4,4-dimethylpiperidin-1-yl)-6-formyl-2-methylpyridin-3-yl)-2-(tert-butoxy)acetate (960 mg, 1.99 mmol, 96% yield). ¹H NMR (500 MHz, chloroform-d) δ 10.29 (s, 1H), 6.26 (br s, 1H), 5.12-4.97 (m, 1H), 4.15-4.05 (m, 1H), 3.54 (t, J=12.1 Hz, 1H), 2.94 (d, J=10.9 Hz, 1H), 2.71 (d, J=11.0 Hz, 1H), 2.66-2.62 (m, 3H), 1.59 (br s, 1H), 1.51 (br s, 1H), 1.41-1.35 (m, 1H), 1.30-1.25 (m, 1H), 1.22-1.18 (m, 12H), 1.16-1.13 (m, 3H), 1.11-1.03 (m, 6H). LCMS (M+H)=483.0, 485.0.

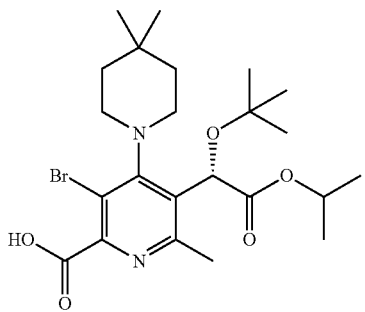 [SMILES: Cc1nc(C(=O)O)c(Br)c(N2CCC(C)(C)CC2)c1[C@H](OC(C)(C)C)C(=O)OC(C)C]

(S)-3-Bromo-5-(1-(tert-butoxy)-2-isopropoxy-2-oxoethyl)-4-(4,4-dimethylpiperidin-1-yl)-6-methylpicolinic acid: To a solution of (S)-isopropyl 2-(5-bromo-4-(4,4-dimethylpiperidin-1-yl)-6-formyl-2-methylpyridin-3-yl)-2-(tert-butoxy)acetate (2.0 g, 4.1 mmol) in DMSO (41 ml) was added potassium phosphate monobasic (1.69 g, 12.4 mmol) in water (10 mL) followed by sodium chlorite (1.12 g, 12.4 mmol) in water (10 mL) and the mixture was stirred overnight. A ppt formed immediately. As the reaction stirred, the precipitated material stuck to the sides of the flask. After stirring overnight, the solution was poured away and the solids were taken up in EtOAc and were then washed with brine, dried (Na₂SO₄), filtered and concentrated to afford the expected product. The DMSO solution also contained some product. It was diluted with EtOAc and washed with Brine. The organic phase was dried over Na₂SO₄, and concentrated and was combined with the material isolated from the ppt. The combined material afforded a quantitative amount of (S)-3-bromo-5-(1-(tert-butoxy)-2-isopropoxy-2-oxoethyl)-4-(4,4-dimethylpiperidin-1-yl)-6-methylpicolinic acid (quantitative). LCMS (M+H)=499.04.

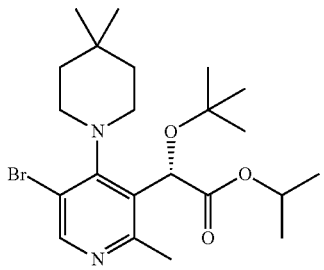 [SMILES: Cc1ncc(Br)c(N2CCC(C)(C)CC2)c1[C@H](OC(C)(C)C)C(=O)OC(C)C]

Isopropyl (S)-2-(5-bromo-4-(4,4-dimethylpiperidin-1-yl)-2-methylpyridin-3-yl)-2-(tert-butoxy)acetate: Water (0.16 ml, 8.8 mmol) followed by diphenylphosphoryl azide (0.76 ml, 3.5 mmol) was added to a stirring solution of (S)-3-bromo-5-(1-(tert-butoxy)-2-isopropoxy-2-oxoethyl)-4-(4,4-dimethylpiperidin-1-yl)-6-methylpicolinic acid (882 mg, 1.77 mmol) in Toluene (18 ml) at rt. The reaction was stirred at 90° C. for 2 h. The mixture was then diluted with EtOAc and washed with sat aq NaHCO₃. The organic phase was dried over Na₂SO₄, filtered and concentrated. The reaction was concentrated, adsorbed onto Celite and purified on silica gel (Biotage, EtOAc/hexanes gradient, 0-100% over 10 CVs) to give the expected product (S)-isopropyl 2-(5-bromo-4-(4,4-dimethylpiperidin-1-yl)-2-methylpyridin-3-yl)-2-(tert-butoxy)acetate in quantitative isolated yield. LCMS (M+H)=455.20, 457.20.

Example 164

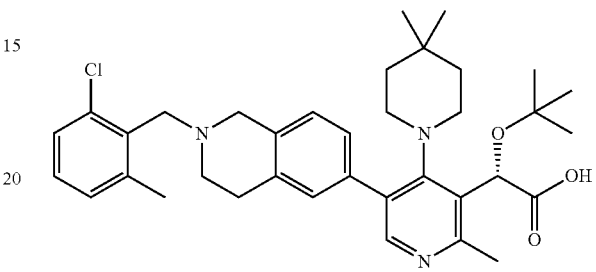

(S)-2-(tert-Butoxy)-2-(5-(2-(2-chloro-6-methylbenzyl)-1,2,3,4-tetrahydroisoquinolin-6-yl)-4-(4,4-dimethylpiperidin-1-yl)-2-methylpyridin-3-yl)acetic acid: (S)-Isopropyl 2-(5-bromo-4-(4,4-dimethylpiperidin-1-yl)-2-methylpyridin-3-yl)-2-(tert-butoxy)acetate (25 mg, 0.055 mmol), 2-(2-chloro-6-methylbenzyl)-6-(4,4,5,5-tetramethyl-1,3,2-dioxaborolan-2-yl)-1,2,3,4-tetrahydroisoquinoline (33 mg, 0.082 mmol), 2-dicyclohexylphosphino-2',6'-dimethoxybiphenyl (4.5 mg, 11 μmol), PdOAc₂ (1.2 mg, 5.5 μmol) and potassium phosphate tribasic (87 mg, 0.41 mmol) were combined under N₂. 1,4-Dioxane (1 ml) and Water (0.2 ml) were added under N₂. The reaction was heated at 80° C. for 1 h. The reaction was concentrated, adsorbed onto celite and was purified on silica gel (Biotage, EtOAc/hexanes gradient, 0-100% over 10 CVs) The isolated residue was subjected to hydrolysis conditions by treating with 0.1 mL of 5N NaOH, in 1.5 mL of EtOH, and was stirred at 80C overnight. The reaction mixture containing the product was submitted to the Single Compound Purification team for purification and analysis. The crude material was purified via preparative LC/MS to give desired product (7.6 mg). ¹H NMR (500 MHz, DMSO-d6) δ 8.01 (s, 1H), 7.29 (d, J=7.3 Hz, 1H), 7.20 (d, J=9.5 Hz, 2H), 7.14-7.08 (m, 1H), 7.06-6.99 (m, 2H), 5.81 (s, 1H), 3.83 (s, 2H), 3.69 (s, 2H), 2.80 (dd, J=14.1, 4.2 Hz, 4H), 2.49 (br. s., 3H), 2.45 (s, 3H), 1.30 (br. s., 3H), 1.25 (s, 3H), 1.12 (s, 10H), 0.88-0.75 (m, 7H). LCMS (M +H)=604.18.

Example 165

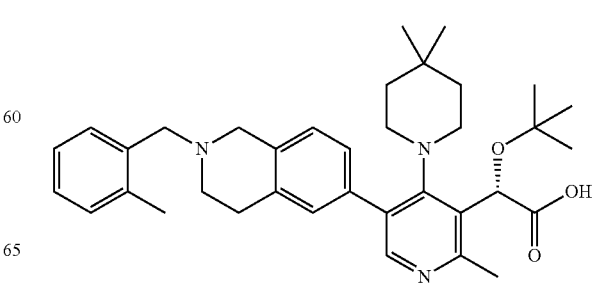

(S)-2-(tert-Butoxy)-2-(4-(4,4-dimethylpiperidin-1-yl)-2-methyl-5-(2-(2-methylbenzyl)-1,2,3,4-tetrahydroisoquinolin-6-yl)pyridin-3-yl)acetic acid: (S)-isopropyl 2-(5-bromo-4-(4,4-dimethylpiperidin-1-yl)-2-methylpyridin-3-yl)-2-(tert-butoxy)acetate (50 mg, 0.11 mmol), 2-(2-chloro-6-methylbenzyl)-6-(4,4,5,5-tetramethyl-1,3,2-dioxaborolan-2-yl)-1,2,3,4-tetrahydroisoquinoline (66 mg, 0.17 mmol), 2-dicyclohexylphosphino-2',6'-dimethoxybiphenyl (9.01 mg, 0.022 mmol), potassium phosphate tribasic (175 mg, 0.823 mmol), PdOAc₂ (2.5 mg, 11 µmol) were combined under N₂. 1,4-Dioxane (1.8 ml) and Water (0.4 ml) was added under N₂. The reaction was stirred at 80° C. for 1 hr. The reaction was concentrated, adsorbed onto celite and was purified on silica gel (Biotage, EtOAc/hexanes gradient 0-100% over 10 CVs). The isolated material was taken up in 1.5 mL of EtOH and treated with 5N aq NaOH (0.20 ml, 1.1 mmol). The reaction was stirred overnight at 80 C. The reaction was purified by preparative reverse phase HPLC on a C18 column using a suitably buffered H₂O/CH₃CN gradient. One of the minor peaks with a M+H matching that of titled compound was re-purified via preparative LC/MS to give desired product (7.1 mg). ¹H NMR (500 MHz, DMSO-d6) δ 8.02 (s, 1H), 7.36-7.32 (m, 1H), 7.30 (d, J=5.5 Hz, 2H), 7.18 (s, 2H), 7.13-7.08 (m, 1H), 7.04 (br. s., 1H), 5.80 (br. s., 1H), 3.64-3.59 (m, 2H), 2.84 (br. s., 1H), 2.74-2.67 (m, 1H), 2.46 (s, 3H), 2.38-2.32 (m, 3H), 1.90 (s, 2H), 1.55 (br. s., 3H), 1.29 (br. s., 3H), 1.10 (s, 13H), 0.87 (br. s., 3H), 0.73 (br. s., 3H). LCMS (M+H)=570.25.

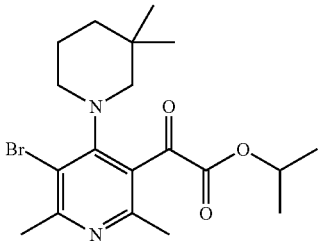 [SMILES: Cc1nc(C)c(C(=O)C(=O)OC(C)C)c(N2CCCC(C)(C)C2)c1Br]

Isopropyl 2-(5-bromo-4-(3,3-dimethylpiperidin-1-yl)-2,6-dimethylpyridin-3-yl)-2-oxoacetate: To a stirred solution of isopropyl 2-(5-bromo-4-chloro-2,6-dimethylpyridin-3-yl)-2-oxoacetate (0.8 g, 2.391 mmol) and DIPEA (0.501 ml, 2.87 mmol) in anhydrous CH₃CN (2.4 mL) was added 3,3-dimethylpiperidine (0.325 g, 2.87 mmol) and the resulting solution was placed in a pre-heated heating block at 90° C. overnight. The reaction mixture was combined with diluted with ethyl acetate (80 mL), washed with water (50 mL), brine (50 mL), dried (MgSO₄), filtered, and concentrated. The residue was purified on ISCO 80 g cartridge (0-25%EtOAC/Hex) to give a isopropyl 2-(5-bromo-4-(3,3-dimethylpiperidin-1-yl)-2,6-dimethylpyridin-3-yl)-2-oxoacetate as a bright yellow viscous oil (0.74 g, 75%). LCMS (M+H)=413.0.

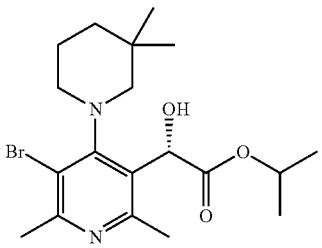 [SMILES: Cc1nc(C)c([C@H](O)C(=O)OC(C)C)c(N2CCCC(C)(C)C2)c1Br]

(S)-Isopropyl 2-(5-bromo-4-(3,3-dimethylpiperidin-1-yl)-2,6-dimethylpyridin-3-yl)-2-hydroxyacetate: To a solution of isopropyl 2-(5-bromo-4-(3,3-dimethylpiperidin-1-yl)-2,6-dimethylpyridin-3-yl)-2-oxoacetate (0.92 g, 2.237 mmol) and (R)-1-methyl-3,3-diphenylhexahydropyrrolo[1,2-c][1,3,2]oxazaborole (0.447 ml, 0.447 mmol) in Toluene at −50° C. was added catecholborane (0.718 ml, 3.35 mmol) slowly. The reaction mixture was slowly warmed up to −15° C. over 5 h and stirred at −10° C. overnight in a chiller. The reaction mixture was diluted with ethyl acetate and washed with 1M Na₂CO₃ (50 mL). The organic layer was isolated, washed with 1M Na₂CO₃, dried over Na₂SO₄ and concentrated. The residue was purified on silica (120 g isco column) using 10-50% ethyl acetate in hexanes. The desired fractions were concentrated to give isopropyl (S)-2-(5-bromo-4-(3,3-dimethylpiperidin-1-yl)-2,6-dimethylpyridin-3-yl)-2-hydroxyacetate as a yellow viscous oil (0.81 g, 1.95 mmol, 87% yield). LCMS (M+H)=415.2.

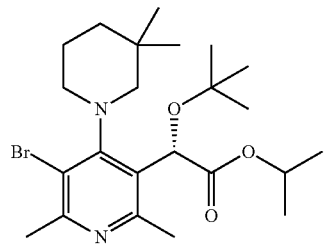 [SMILES: Cc1nc(C)c([C@H](OC(C)(C)C)C(=O)OC(C)C)c(N2CCCC(C)(C)C2)c1Br]

(S)-Isopropyl 2-(5-bromo-4-(3,3-dimethylpiperidin-1-yl)-2,6-dimethylpyridin-3-yl)-2-(tert-butoxy)acetate: In a 100 ml round bottom flask fitted with a shlenk adaptor with rubber septum (with empty balloon attached), Isobutylene gas was vigorously bubbled for 20 minutes into a cooled (0° C.) solution of (S)-isopropyl 2-(5-bromo-4-(3,3-dimethylpiperidin-1-yl)-2,6-dimethylpyridin-3-yl)-2-hydroxyacetate (0.81 g, 1.960 mmol) and perchloric acid (0.168 ml, 1.960 mmol) in DCM (39 mL) until the volume doubled and the balloon filled to firmness. After 2 hrs, the isobutylene line was disconnected and needle pulled to just above the solution line then connected to a bubbler to monitor isobutylene gas exit. The reaction mixture was stirred at 0° C. for 1 h, the ice bath was removed and warmed up to rt while monitoring for conversion. After 2 hrs the reaction appeared to go to full conversion according to LCMS. The reaction mixture was poured into a 500 mL Erlenmeyer flask and made basic with 2M sodium carbonate while vigorously stirring. The organic layer was separated and washed with water, followed by brine, collected, dried (MgSO₄), filtered and volatiles evaporated to give a yellow oil as the crude product. The crude product was purified on silica gel (80 g column, 10-50% EtOAc/Hex) to give the product (S)-isopropyl 2-(5-bromo-4-(3,3-dimethylpiperidin-1-yl)-2,6-dimethylpyridin-3-yl)-2-(tert-butoxy)acetate (0.704 g, 1.50 mmol, 77% yield) as a yellow viscous oil. ¹H NMR (500 MHz, CDCl₃) δ 6.40 (br. s., 1H), 5.14-4.97 (m, 1H), 3.89 (t, J=10.3 Hz, 1H), 3.24 (d, J=11.2 Hz, 1H), 2.91-2.40 (m, 9H), 1.85 (d, J=11.7 Hz, 1H), 1.68 (d, J=11.5 Hz, 1H), 1.51 (d, J=12.9 Hz, 1H), 1.42-0.86 (m, 22H). LCMS (M+H)=470.1.

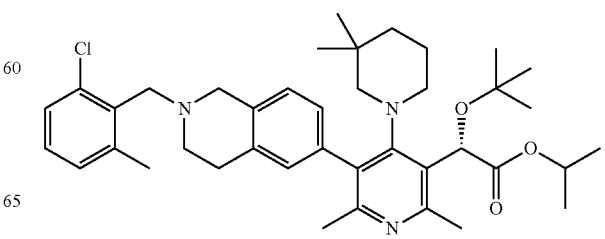

(S)-Isopropyl 2-(tert-butoxy)-2-(5-(2-(2-chloro-6-methylbenzyl)-1,2,3,4-tetrahydroisoquinolin-6-yl)-4-(3,3-dimethylpiperidin-1-yl)-2,6-dimethylpyridin-3-yl)acetate: A mixture of (S)-isopropyl 2-(5-bromo-4-(3,3-dimethylpiperidin-1-yl)-2,6-dimethylpyridin-3-yl)-2-(tert-butoxy)acetate (0.07 g, 0.149 mmol), 2-(2-chloro-6-methylbenzyl)-6-(4,4,5,5-tetramethyl-1,3,2-dioxaborolan-2-yl)-1,2,3,4-tetrahydroisoquinoline (0.089 g, 0.224 mmol), 2-dicyclohexylphosphino-2',6'-dimethoxybiphenyl (0.012 g, 0.030 mmol), palladium(II) acetate (3.35 mg, 0.015 mmol) and 2M $K_3PO_4$ (0.559 mL, 1.118 mmol) in 1,4-dioxane (1772 µl) under $N_2$. The reaction mixture was degassed for 5 min and heated at 80° C. for 1 h. The organic layer was isolated and purified on silica gel (24 g, isco column) using 0-85% ethyl acetate in hexanes. The desired fractions were concentrated to give (S)-isopropyl 2-(tert-butoxy)-2-(5-(2-(2-chloro-6-methylbenzyl)-1,2,3,4-tetrahydroisoquinolin-6-yl)-4-(3,3-dimethylpiperidin-1-yl)-2,6-dimethylpyridin-3-yl)acetate as a light brown foamy solid (57 mg, 0.086 mmol, 58%). LCMS (M+H)=661.5.

Example 166

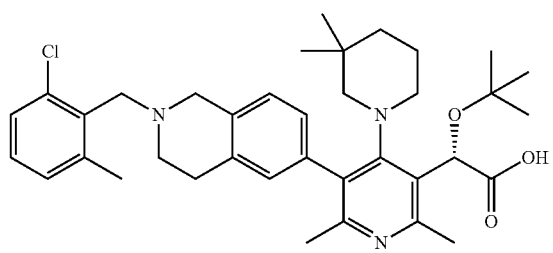 [SMILES: Cc1cccc(Cl)c1CN1CCc2cc(-c3c(C)nc(C)c([C@H](OC(C)(C)C)C(=O)O)c3N3CCCC(C)(C)C3)ccc2C1]

(S)-2-(tert-butoxy)-2-(5-(2-(2-chloro-6-methylbenzyl)-1,2,3,4-tetrahydroisoquinolin-6-yl)-4-(3,3-dimethylpiperidin-1-yl)-2,6-dimethylpyridin-3-yl)acetic acid: NaOH (0.173 mL, 0.863 mmol) was added to a solution of (S)-isopropyl 2-(tert-butoxy)-2-(5-(2-(2-chloro-6-methylbenzyl)-1,2,3,4-tetrahydroisoquinolin-6-yl)-4-(3,3-dimethylpiperidin-1-yl)-2,6-dimethylpyridin-3-yl)acetate (0.057 g, 0.086 mmol) in ethanol (1.5 mL) and the mixture was heated at 80° C. for 4 h. Additional NaOH (0.173 mL, 0.863 mmol) was added and the mixture was heated for 6 h, cooled purified by preparative LC/MS to give desired product (32.0 mg, 0.052 mmol, 60%). LCMS (M+H)=619.3.

Biological Methods

Inhibition of HIV replication: A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press.1990). Results are shown in Table 1. Activity equal to A refers to a compound having an $EC_{50} \leq 100$ nM, while B and C denote compounds having an $EC_{50}$ between 100 nM and 1 uM (B) or >1 uM (C).

TABLE 1

| Compound | Activity | $EC_{50}$ µM |
|---|---|---|
| 1 | A | 0.006 |
| 2 | A | |
| 3 | A | |
| 4 | A | |
| 5 | A | |
| 6 | A | |
| 7 | A | 0.004 |
| 8 | A | |
| 9 | A | |
| 10 | C | 1.475 |
| 11 | A | |
| 12 | A | |
| 13 | A | |
| 14 | A | 0.034 |
| 15 | A | |
| 16 | A | |
| 17 | A | |
| 18 | A | |
| 19 | A | |
| 20 | A | |
| 21 | A | |
| 22 | A | |
| 23 | A | 0.003 |
| 24 | A | |
| 25 | A | |
| 26 | A | |
| 27 | A | |
| 28 | A | |
| 29 | A | |
| 30 | A | |
| 31 | A | 0.011 |
| 32 | A | |
| 33 | A | |
| 34 | A | |
| 35 | A | |
| 36 | A | |
| 37 | A | |
| 38 | A | 0.006 |
| 39 | A | |
| 40 | A | |
| 41 | A | |
| 42 | A | |
| 43 | A | |
| 44 | A | |
| 45 | A | 0.003 |
| 46 | A | |
| 47 | A | |
| 48 | A | |
| 49 | A | |
| 50 | A | |
| 51 | A | 0.003 |
| 52 | A | |
| 53 | A | |

TABLE 1-continued

| Compound | Activity | EC$_{50}$ μM |
|---|---|---|
| 54 | A | |
| 55 | A | |
| 56 | A | |
| 57 | A | |
| 58 | A | |
| 59 | A | 0.058 |
| 60 | A | |
| 61 | A | |
| 62 | A | |
| 63 | A | |
| 64 | A | |
| 65 | A | |
| 66 | A | 0.013 |
| 67 | A | |
| 68 | A | |
| 69 | A | |
| 70 | A | |
| 71 | A | |
| 72 | A | |
| 73 | A | 0.007 |
| 74 | A | |
| 75 | A | |
| 76 | A | |
| 77 | A | |
| 78 | A | |
| 79 | A | |
| 80 | A | 0.003 |
| 81 | A | |
| 82 | A | |
| 83 | A | |
| 84 | A | |
| 85 | A | |
| 86 | A | |
| 87 | A | |
| 88 | A | 0.012 |
| 89 | A | |
| 90 | A | |
| 91 | A | |
| 92 | A | |
| 93 | A | |
| 94 | A | |
| 95 | A | |
| 96 | A | 0.003 |
| 97 | A | |
| 98 | A | |
| 99 | A | |
| 100 | A | |
| 101 | A | |
| 102 | A | |
| 103 | A | 0.012 |
| 104 | A | |
| 105 | A | |
| 106 | A | |
| 107 | A | |
| 108 | A | |
| 109 | A | |
| 110 | A | 0.008 |
| 111 | A | |
| 112 | A | |
| 113 | A | |
| 114 | A | |
| 115 | A | |
| 116 | A | 0.002 |
| 117 | A | |
| 118 | A | |
| 119 | A | |
| 120 | A | |
| 121 | A | |
| 122 | A | |
| 123 | A | 0.011 |
| 124 | A | |
| 125 | A | |
| 126 | A | |
| 127 | A | |
| 128 | A | |
| 129 | A | 0.003 |
| 130 | A | |
| 131 | A | |
| 132 | A | |
| 133 | A | |
| 134 | A | 0.012 |
| 135 | A | |
| 136 | A | |
| 137 | A | |
| 138 | A | |
| 139 | A | 0.03 |
| 140 | A | |
| 141 | A | |
| 142 | A | |
| 143 | A | |
| 144 | A | 0.008 |
| 145 | A | |
| 146 | A | |
| 147 | A | |
| 148 | A | |
| 149 | A | |
| 150 | A | 0.021 |
| 151 | A | |
| 152 | A | |
| 153 | A | |
| 154 | A | |
| 155 | A | |
| 156 | A | 0.008 |
| 157 | A | |
| 158 | A | |
| 159 | A | |
| 160 | A | |
| 161 | A | |
| 162 | A | |
| 163 | A | 0.076 |
| 164 | A | 0.003 |
| 165 | A | |
| 166 | A | 0.023 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I:

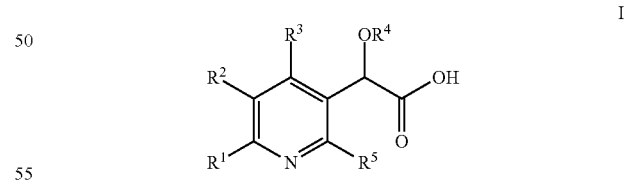

or a pharmaceutically acceptable salt thereof, wherein:

$R^1$ is hydrogen, $C_{1-6}$alkyl or $C_{3-7}$cycloalkyl;

$R^2$ is tetrahydroisoquinolinyl, substituted with 1 $R^6$ substituent and optionally substituted with 1, 2 or 3 substituents independently selected from the group consisting of halo and $C_{1-6}$alkyl;

$R^3$ is piperidinyl, optionally substituted with 1, 2 or 3 substituents independently selected from the group consisting of cyano, halo, $C_{1-6}$alkyl, $C_{1-6}$haloalkyl, $C_{1-6}$alkoxy and $C_{1-6}$haloalkoxy;

R⁴ is $C_{1-6}$alkyl or $C_{1-6}$haloalkyl;
R⁵ is $C_{1-6}$alkyl;
R⁶ is (Ar¹)$C_{1-6}$alkyl; and
Ar¹ is phenyl, optionally substituted with 1, 2, 3, 4 or 5 substituents independently selected from the group consisting of cyano, hydroxy, halo, $C_{1-6}$alkyl, $C_{1-6}$haloalkyl, $C_{1-6}$alkoxy, $C_{1-6}$haloalkoxy, (hydroxy)$C_{1-6}$alkoxy, ($C_{1-6}$alkoxy)$C_{1-6}$alkoxy, phenoxy, benzyloxy, carboxy, $C_{3-7}$cycloalkyl, (cyano)$C_{3-7}$cycloalkyl and phenyl.

2. A compound of claim 1, wherein the compound is:

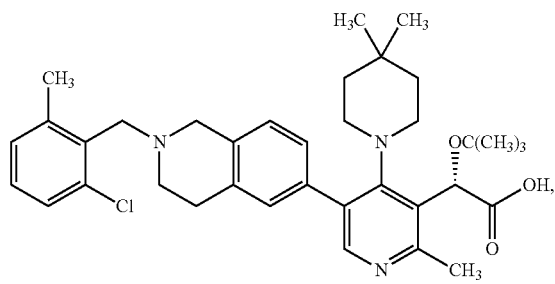

or a pharmaceutically acceptable salt thereof.

3. A pharmaceutical composition comprising a compound of claim 2, or a pharmaceutically acceptable salt thereof.

4. The pharmaceutical composition of claim 3, wherein the pharmaceutical composition further comprises at least one additional therapeutic agent selected from the group consisting of a nucleoside human immunodeficiency virus reverse transcriptase inhibitor, a non-nucleoside human immunodeficiency virus reverse transcriptase inhibitor, a human immunodeficiency virus protease inhibitor, a human immunodeficiency virus integrase inhibitor, a human immunodeficiency virus fusion inhibitor, a human immunodeficiency virus attachment inhibitor, a human immunodeficiency virus budding inhibitor, a human immunodeficiency virus maturation inhibitor, a C—C chemokine receptor type 5 inhibitor and a C—X—C chemokine receptor type 4 inhibitor.

5. The pharmaceutical composition of claim 4, wherein the at least one additional therapeutic agent is dolutegravir.

6. A method for treating a human immunodeficiency virus infection in a patient, comprising administering to a patient in need thereof, a compound of claim 2, or a pharmaceutically acceptable salt thereof.

7. The method of claim 6, wherein the method further comprises administering at least one additional therapeutic agent selected from the group consisting of a nucleoside human immunodeficiency virus reverse transcriptase inhibitor, a non-nucleoside human immunodeficiency virus reverse transcriptase inhibitor, a human immunodeficiency virus protease inhibitor, a human immunodeficiency virus integrase inhibitor, a human immunodeficiency virus fusion inhibitor, a human immunodeficiency virus attachment inhibitor, a human immunodeficiency virus budding inhibitor, a human immunodeficiency virus maturation inhibitor, a C—C chemokine receptor type 5 inhibitor and a C—X—C chemokine receptor type 4 inhibitor.

8. The method of claim 7, wherein the at least one additional therapeutic agent is dolutegravir.

* * * * *